United States Patent
Glunz

(10) Patent No.: US 7,094,783 B2
(45) Date of Patent: Aug. 22, 2006

(54) BICYCLIC PYRIMIDINONES AS COAGULATION CASCADE INHIBITORS

(75) Inventor: Peter W. Glunz, Wilmingtonq, DE (US)

(73) Assignee: Bristol-Myers Squibb Company, Princeton, NJ (US)

( * ) Notice: Subject to any disclaimer, the term of this patent is extended or adjusted under 35 U.S.C. 154(b) by 229 days.

(21) Appl. No.: 10/465,426

(22) Filed: Jun. 19, 2003

(65) Prior Publication Data

US 2004/0006065 A1    Jan. 8, 2004

Related U.S. Application Data

(60) Provisional application No. 60/391,784, filed on Jun. 26, 2002.

(51) Int. Cl.
C07D 239/02    (2006.01)
A01N 43/58    (2006.01)
A61K 31/50    (2006.01)

(52) U.S. Cl. ........... 514/247; 514/247; 514/252.14; 514/252.19; 544/224; 544/242; 544/245

(58) Field of Classification Search ........... 544/224, 544/242, 245; 514/247, 252.14, 252.19
See application file for complete search history.

(56) References Cited

U.S. PATENT DOCUMENTS

| | | | |
|---|---|---|---|
| 4,252,807 A | 2/1981 | Hermecz et al. | |
| 5,023,236 A | 6/1991 | Edgington et al. | |
| 5,656,627 A | 8/1997 | Bemis et al. | |
| 5,716,929 A | 2/1998 | Bemis et al. | |
| 5,756,466 A | 5/1998 | Bemis et al. | |
| 5,843,442 A | 12/1998 | Soule et al. | |
| 5,847,135 A | 12/1998 | Bemis et al. | |
| 5,859,010 A | 1/1999 | Petersen et al. | |
| 5,962,487 A | 10/1999 | Webber et al. | |
| 5,973,111 A | 10/1999 | Bemis et al. | |
| 6,103,711 A | 8/2000 | Bemis et al. | |
| 6,653,295 B1 * | 11/2003 | Glunz et al. ........... | 514/64 |

FOREIGN PATENT DOCUMENTS

| | | |
|---|---|---|
| WO | WO 99/31122 | 6/1999 |
| WO | WO 01/87851 | 11/2001 |

* cited by examiner

*Primary Examiner*—James O. Wilson
*Assistant Examiner*—Paul V. Ward
(74) *Attorney, Agent, or Firm*—Jing G. Sun

(57) ABSTRACT

The present invention relates generally to compounds that inhibit serine proteases. In particular it is directed to novel amino-bicyclic pyrimidinone compounds of Formula (I):

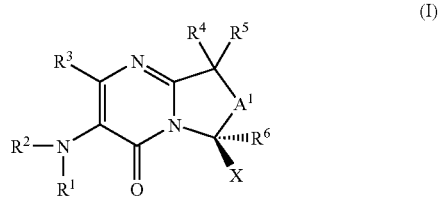

or a stereoisomer or pharmaceutically acceptable salt form thereof, which are useful as selective inhibitors of serine protease enzymes of the coagulation cascade; for example thrombin, factor Xa, factor XIa, factor IXa, and/or factor VIIa. In particular, it relates to compounds that are factor VIIa inhibitors. This invention also relates to pharmaceutical compositions comprising these compounds and methods of using the same.

12 Claims, No Drawings

BICYCLIC PYRIMIDINONES AS COAGULATION CASCADE INHIBITORS

CROSS-REFERENCE TO RELATED APPLICATIONS

The present application claims the priority benefit of U.S. Provisional Application No. 60/391,784, filed Jun. 26, 2002, which is expressly incorporated fully herein by reference.

FIELD OF THE INVENTION

The present invention relates generally to compounds that inhibit serine proteases. In particular it is directed to novel amino-bicyclic pyrimidinone compounds of Formula (I):

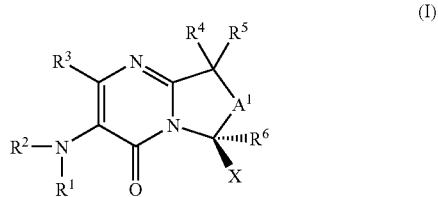

or a stereoisomer or pharmaceutically acceptable salt form thereof, which are useful as selective inhibitors of serine protease enzymes of the coagulation cascade; for example thrombin, factor Xa, factor XIa, factor IXa, and/or factor VIIa. In particular, it relates to compounds that are factor VIIa inhibitors. This invention also relates to pharmaceutical compositions comprising these compounds and methods of using the same.

BACKGROUND OF THE INVENTION

Factor VIIa is a plasma serine protease involved in the regulation of hemostasis. It binds with high affinity to Tissue Factor in the presence of calcium ions to form a complex. The complex exhibits enhanced proteolytic activity and is the primary initiator of the extrinsic pathway of blood coagulation. See Carson, S. D. and Brozna, J. P. *Blood Coag. Fibrinol.* 1993, 4, 281–292. The complex initiates blood coagulation by activating factor X to factor Xa, factor IX to factor IXa and additional factor VII to factor VIIa. Ultimately, the activity of factor VIIa induces the conversion of prothrombin to thrombin. Thrombin functions to convert fibrinogen to fibrin, which forms a clot through polymerization.

While blood coagulation is a necessary and important part in the regulation of an organism's hemostasis, blood coagulation can also have deleterious effects. For instance, thrombosis is the formation or presence of a blood clot inside a blood vessel or cavity of the heart. Such a blood clot can lodge in a blood vessel, blocking circulation and inducing a heart attack.

Because of the role of serine proteases in blood coagulation, researchers have postulated that the inhibition of factor VIIa could be used to treat or prevent disease states involving thrombosis. Work has accordingly been performed to identify and optimize factor VIIa inhibitors. For example, U.S. Pat. No. 5,859,010 discusses factor VIIa/Tissue Factor inhibitors that are dihydroxamates having a spacing from 0.37 nm to about 0.77 nm; U.S. Pat. No. 5,843,442 reports monoclonal-type antibodies or antibody fragments possessing inhibitory activity; and, U.S. Pat. No. 5,023,236 presents peptides and peptide derivatives that specifically inhibit the proteolytic active site of serine protease coagulation factor VII/VIIa.

In addition to the above, bicyclic pyrimidinones are known in the art. For example, PCT International publication WO 01/87851 describes substituted polycyclic aryl and heteroaryl pyrimidinones useful as inhibitors of the coagulation cascade. U.S. Pat. No. 5,962,487 and related PCT International publication WO 99/31122 describe a generic scope of peptidyl compounds including, but not limited to, bicyclic pyrimidinones, useful as picornaviral 3C inhibitors. U.S. Pat. Nos. 5,847,135; 5,756,466; 5,656,627; 5,716,929; 6,103,711; and 5,973,111 describe a generic scope of compounds including, but not limited to, substituted bicyclic pyrimidinone compounds as peptide inhibitors of interleukin-1β converting enzyme. U.S. Pat. No. 4,252,807 describes bicyclic pyrimidinones useful as anti-atherosclerotic agents. The scope of the present invention is considered not to be exemplified nor suggested by the above references.

While a number of factor VIIa inhibitors have been discussed in the art, improved inhibitors, especially non-peptide inhibitors, of serine proteases for the treatment of thromboembolic disorders are always desirable. The present invention discloses non-peptide serine protease inhibitors which are bicyclic pyrimidinones useful in the treatment of thromboembolic disorders.

In addition, it is also desirable to find new compounds with improved pharmacological characteristics compared with known serine protease inhibitors. For example, it is preferred to find new compounds with improved factor XIa inhibitory activity and selectivity for factor XIa versus other serine proteases. It is also desirable and preferable to find compounds with advantageous and improved characteristics in one or more of the following categories, but are not limited to: (a) pharmaceutical properties; (b) dosage requirements; (c) factors which decrease blood concentration peak-to-trough characteristics; (d) factors that increase the concentration of active drug at the receptor; (e) factors that decrease the liability for clinical drug-drug interactions; (f) factors that decrease the potential for adverse side-effects; and, (g) factors that improve manufacturing costs or feasibility.

SUMMARY OF THE INVENTION

Accordingly, the present invention provides novel bicyclic pyrimidinone compounds of Formula (I), which are useful as selective inhibitors of serine protease enzymes, especially factor VIIa, and pharmaceutically acceptable salts or prodrugs thereof.

The present invention also provides pharmaceutical compositions comprising a pharmaceutically acceptable carrier and a therapeutically effective amount of at least one of the compounds of the present invention or a pharmaceutically acceptable salt or prodrug form thereof.

The present invention also provides a method for modulation of the coagulation cascade comprising administering to a host in need of such treatment a therapeutically effective amount of at least one of the compounds of the present invention or a pharmaceutically acceptable salt or prodrug form thereof.

The present invention also provides a method for treating thromboembolic disorders comprising administering to a host in need of such treatment a therapeutically effective amount of at least one of the compounds of the present invention or a pharmaceutically acceptable salt or prodrug form thereof.

The present invention also provides novel bicyclic pyrimidinone compounds for use in therapy.

The present invention also provides the use of novel bicyclic pyrimidinone compounds for the manufacture of a medicament for the treatment of a thromboembolic disorder.

These and other embodiments, which will become apparent during the following detailed description, have been achieved by the inventors' discovery that the presently claimed novel bicyclic pyrimidinone compounds, or pharmaceutically acceptable salt or prodrug forms thereof, are effective factor VIIa inhibitors.

DETAILED DESCRIPTION OF THE INVENTION

In a first aspect, the present invention provides, inter alia, compounds of Formula (I):

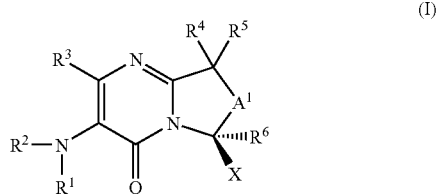

or a stereoisomer or pharmaceutically acceptable salt form thereof, wherein:

$A^1$ is —$CH_2$—, —$CH_2CH_2$—, —O—$CH_2$—, —NH—$CH_2$—, or —$CH_2CH_2CH_2$—;

wherein $A^1$ is optionally substituted with 0–2 $R^{14}$;

X is —C(O)NH—$(CR^{16}R^{16})_n$—$R^8$, —S(O)$_2$NH—$(CR^{16}R^{16})_n$—$R^8$, —$CR^{15}R^{15}$—NHC(=O)—$(CR^{16}R^{16})_n$—$R^8$, —$CR^{15}R^{15}$—NHS(=O)$_2$—$(CR^{16}R^{16})_n$—$R^8$, or —$CR^{16}R^{16}$—NH—$R^8$;

n is 0, 1, or 2;

$R^1$ is H, $C_1$–$C_6$ alkyl substituted with 0–3 $R^{2b}$, $C_2$–$C_6$ alkenyl substituted with 0–3 $R^{2b}$, $C_2$–$C_6$ alkynyl substituted with 0–3 $R^{2b}$, $C_3$–$C_{10}$ carbocycle substituted with 0–3 $R^{2c}$, aryl substituted with 0–3 $R^{2c}$, or 5–10 membered heterocycle consisting of carbon atoms and 1–4 heteroatoms selected from the group: O, S, and N, and substituted with 0–3 $R^{2c}$;

$R^2$ is H, C(=O)$R^{2a}$, C(=O)O$R^{2a}$, —C(=O)N$R^{2a}R^{2a}$, —S(=O)$R^{2a}$, —S(=O)$_2R^{2a}$, —S(=O)$_2$N$R^{2a}R^{2a}$, $C_1$–$C_6$ alkyl substituted with 0–3 $R^{2b}$, $C_2$–$C_6$ alkenyl substituted with 0–3 $R^{2b}$, $C_2$–$C_6$ alkynyl substituted with 0–3 $R^{2b}$, $C_3$–$C_{10}$ carbocycle substituted with 0–3 $R^{2c}$, aryl substituted with 0–3 $R^{2c}$, or 5–10 membered heterocycle consisting of carbon atoms and 1–4 heteroatoms selected from the group: O, S, and N, and substituted with 0–3 $R^{2c}$;

each $R^{2a}$ is, independently at each occurrence, H, $C_1$–$C_6$ alkyl substituted with 0–3 $R^{2b}$, $C_2$–$C_6$ alkenyl substituted with 0–3 $R^{2b}$, $C_2$–$C_6$ alkynyl substituted with 0–3 $R^{2b}$, $C_3$–$C_{10}$ carbocycle substituted with 0–3 $R^{2c}$, aryl substituted with 0–3 $R^{2c}$, or 5–10 membered heterocycle consisting of carbon atoms and 1–4 heteroatoms selected from the group: O, S, and N, and substituted with 0–3 $R^{2c}$;

provided when $R^2$ is —S(=O)$R^{2a}$ or —S(=O)$_2R^{2a}$, then $R^{2a}$ is not H;

each $R^{2b}$ is, independently at each occurrence, H, F, Cl, Br, I, $NO_2$, CN, —NCS, —$CF_3$, —$OCF_3$, —$CH_3$, —$CH_2CH_3$, —$CH(CH_3)_2$, —$OCH_3$, =O, OH, $CO_2H$, $NH_2$, $NH(CH_3)$, $N(CH_3)_2$, $CO_2R^{21}$, —C(=O)N$R^{21}R^{21}$, —NHC(=O)$R^{21}$, $NR^{21}R^{21}$, —NHSO$_2R^{21}$, —SO$_2R^{21}$, —SO$_2$N$R^{21}R^{21}$, O$R^{2a}$, —S$R^{21a}$, —C(=O)$R^{21a}$, —S(=O)$R^{21a}$, $C_1$–$C_4$ haloalkyl, $C_1$–$C_4$ haloalkoxy, $C_3$–$C_{10}$ carbocycle substituted with 0–3 $R^{2c}$, aryl substituted with 0–3 $R^{2c}$, or 5–10 membered heterocycle consisting of carbon atoms and 1–4 heteroatoms selected from the group: O, S, and N, and substituted with 0–3 $R^{2c}$;

each $R^{2c}$ is, independently at each occurrence, H, F, Cl, Br, I, $NO_2$, CN, —NCS, —$CF_3$, —$OCF_3$, —$CH_3$, —$OCH_3$, =O, OH, $CO_2H$, $NH_2$, $NH(CH_3)$, $N(CH_3)_2$, $CO_2R^{21}$, —C(=O)N$R^{21}R^{21}$, —NHC(=O)$R^{21}$, —$NR^{21}R^{21}$, —NHSO$_2R^{21}$, —SO$_2R^{21}$, —SO$_2$N$R^{21}R^{21}$, —O$R^{21a}$, —S$R^{21a}$, —C(=O)$R^{21a}$, —S(=O)$R^{21a}$, $C_1$–$C_4$ haloalkyl, $C_1$–$C_4$ haloalkoxy, $C_1$–$C_4$ alkyl substituted with 0–3 $R^{2d}$, $C_2$–$C_4$ alkenyl substituted with 0–3 $R^{2d}$, $C_2$–$C_4$ alkynyl substituted with 0–3 $R^{2d}$, $C_3$–$C_6$ carbocycle substituted with 0–3 $R^{2d}$, ($C_3$–$C_6$ carbocycle)$C_1$–$C_4$ alkyl- substituted with 0–3 $R^{2d}$, (aryl)$C_1$–$C_4$ alkyl-substituted with 0–5 $R^{2d}$, or 5–6 membered heterocycle consisting of carbon atoms and 1–4 heteroatoms selected from the group: O, S, and N, and substituted with 0–4 $R^{2d}$;

each $R^{2d}$ is, independently at each occurrence, H, F, Cl, Br, I, $NO_2$, CN, —NCS, —$CF_3$, —$OCF_3$, —$CH_3$, —$OCH_3$, =O, OH, $CO_2H$, $NH_2$, $NH(CH_3)$, $N(CH_3)_2$, $CO_2R^{21}$, —C(=O)N$R^{21}R^{21}$, —NHC(=O)$R^{21}$, —$NR^{21}$ $R^{21}$, —NHSO$_2R^{21}$, —SOR$^{21}$, —SO$_2$N$R^{21}$ $R^{21}$, —O$R^{21a}$, —S$R^{21a}$, —C(=O)$R^{21a}$, —S(=O)$R^{21a}$, $C_1$–$C_4$ alkyl, $C_1$–$C_4$ alkoxy, $C_1$–$C_4$ haloalkyl, or $C_1$–$C_4$ haloalkoxy;

$R^3$ is H, F, Cl, Br, I, $C_1$–$C_6$ alkyl substituted with 0–3 $R^{3a}$, $C_2$–$C_6$ alkenyl substituted with 0–3 $R^{3a}$, $C_2$–$C_6$ alkynyl substituted with 0–3 $R^{3a}$, $C_3$–$C_{10}$ carbocycle substituted with 0–3 $R^{3b}$, aryl substituted with 0–3 $R^{3b}$, or 5–10 membered heterocycle consisting of carbon atoms and 1–4 heteroatoms selected from the group: O, S, and N, and substituted with 0–3 $R^{3b}$;

each $R^{3a}$ is, independently at each occurrence, H, F, Cl, Br, I, $NO_2$, CN, —NCS, —$CF_3$, —$OCF_3$, —$CH_3$, —$OCH_3$, =O, OH, $CO_2H$, $NH_2$, $NH(CH_3)$, $N(CH_3)_2$, $CO_2R^{21}$, —C(=O)N$R^{21}R^{21}$, —NHC(=O)$R^{21}$, —$NR^{21}R^{21}$, —NHSO$_2R^{21}$, —SO$_2R^{21}$, —SO$_2$N$R^{21}R^{21}$, —O$R^{21a}$, —S$R^{21a}$, —C(=O)$R^{21a}$, —S(=O)$R^{21a}$, $C_1$–$C_4$ haloalkyl, $C_1$–$C_4$ haloalkoxy, $C_3$–$C_{10}$ carbocycle substituted with 0–3 $R^{3b}$, aryl substituted with 0–3 $R^{3b}$, or 5–10 membered heterocycle consisting of carbon atoms and 1–4 heteroatoms selected from the group: O, S, and N, and substituted with 0–3 $R^{3b}$;

each $R^{3b}$ is, independently at each occurrence, H, F, Cl, Br, I, $NO_2$, CN, —NCS, —$CF_3$, —$OCF_3$, —$CH_3$, —$OCH_3$, =O, OH, $CO_2H$, $NH_2$, $NH(CH_3)$, $N(CH_3)_2$, $CO_2R^{21}$, —C(=O)N$R^{21}R^{21}$, —NHC(=O)$R^{21}$, —$NR^{21}R^{21}$, —NHSO$_2R^{21}$, —SO$_2R^{21}$, —SO$_2$N$R^{21}R^{21}$, —O$R^{21a}$, S$R^{21a}$, —C(=O)$R^{21a}$, —S(=O)$R^{21a}$, $C_1$–$C_6$ alkyl, $C_2$–$C_6$ alkenyl, $C_2$–$C_6$ alkynyl, $C_1$–$C_4$ haloalkyl, $C_1$–$C_4$ haloalkoxy, $C_3$–$C_{10}$ carbocycle substituted with 0–3 $R^{3c}$, aryl substituted with 0–3 $R^{3c}$, or 5–10 membered heterocycle consisting of carbon atoms and 1–4 heteroatoms selected from the group: O, S, and N, and substituted with 0–3 $R^{3c}$;

each $R^{3c}$ is, independently at each occurrence, H, F, Cl, Br, I, $NO_2$, CN, —NCS, —$CF_3$, —$OCF_3$, —$CH_3$, —$OCH_3$, =O, OH, $CO_2H$, $NH_2$, $NH(CH_3)$, $N(CH_3)_2$, $CO_2R^{21}$, —C(=O)N$R^{21}$ $R^{21}$, —NHC(=O)$R^{21}$, —$NR^{21}R^{21}$, —NHSO$_2R^{21}$, —SO$_2R^{21}$, —SO$_2$N$R^{21}$ $R^{21}$, —O$R^{21a}$, —$SR^{21a}$, —$C(=O)R^{21a}$, —$S(=O)R^{21a}$, $C_1$–$C_4$ alkyl, $C_1$–$C_4$ alkoxy, $C_1$–$C_4$ haloalkyl, or $C_1$–$C_4$ haloalkoxy;

$R^4$ is H, halo, —$CF_3$, —$OCF_3$, OH, CN, $NO_2$, —$OR^{22}$, —$SR^{22}$, —$NR^{22}R^{23}$, —$C(=O)R^{22}$, —$C(=O)NR^{22}R^{23}$, —$NR^{24}C(=O)R^{22}$, —$NR^{24}C(=O)NR^{22}R^{23}$, —$NR^{24}C(=O)NR^{24}C(=O)R^{22}$, —$C(=O)OR^{22}$, —$OC(=O)R^{22}$, —$OC(=O)OR^{22}$, —$NR^{24}C(=O)OR^{22}$, —$OC(=O)NR^{22}R^{23}$, —$S(=O)R^{22}$, —$S(=O)_2R^{22}$, —$S(=O)NR^{22}R^{23}$, —$S(=O)_2NR^{22}R^{23}$, —$NR^{24}S(=O)_2NR^{22}R^{23}$, —$NR^{24}S(=O)R^{22}$, —$NR^{24}S(=O)_2R^{22}$, $C_1$–$C_4$ haloalkyl, $C_1$–$C_8$ alkoxy, ($C_1$–$C_4$ haloalkyl)oxy, $C_1$–$C_8$ alkyl substituted with 0–3 $R^{4a}$, $C_2$–$C_8$ alkenyl substituted with 0–3 $R^{4a}$, $C_2$–$C_8$ alkynyl substituted with 0–3 $R^{4a}$, $C_3$–$C_{10}$ carbocycle substituted with 0–3 $R^{26}$, aryl substituted with 0–5 $R^{26}$, or 5–10 membered heterocycle containing from 1–4 heteroatoms selected from the group consisting of N, O, and S, and substituted with 0–3 $R^{27}$;

each $R^{4a}$ is, independently at each occurrence, H, halo, —$CF_3$, —$OCF_3$, OH, CN, $NO_2$, —$OR^{22}$, —$SR^{22}$, —$NR^{22}R^{23}$, —$C(=O)R^{22}$, —$C(=O)NR^{22}R^{23}$, —$NR^{24}C(=O)R^{22}$, —$NR^{24}C(=O)NR^{22}R^{23}$, —$NR^{24}C(=O)NR^{24}C(=O)R^{22}$, —$C(=O)OR^{22}$, —$OC(=O)R^{22}$, —$OC(=O)OR^{22}$, —$NR^{24}C(=O)OR^{22}$, —$OC(=O)NR^{22}R^{23}$, —$S(=O)R^{22}$, —$S(=O)_2R^{22}$, —$S(=O)NR^{22}R^{23}$, —$S(=O)_2NR^{22}R^{23}$, —$NR^{24}S(=O)_2NR^{22}R^{23}$, —$NR^{24}S(=O)R^{22}$, —$NR^{24}S(=O)_2R^{22}$, $C_1$–$C_4$ haloalkyl, $C_1$–$C_8$ alkoxy, ($C_1$–$C_4$ haloalkyl)oxy, $C_3$–$C_{10}$ carbocycle substituted with 0–3 $R^{26}$, aryl substituted with 0–5 $R^{26}$, or 5–10 membered heterocycle containing from 1–4 heteroatoms selected from the group consisting of N, O, and S, and substituted with 0–3 $R^{27}$;

$R^5$ is H, halo, $C_{1–4}$ haloalkyl, $C_1$–$C_8$ alkyl substituted with 0–3 $R^{4a}$, $C_2$–$C_8$ alkenyl substituted with 0–3 $R^{4a}$, $C_2$–$C_8$ alkynyl substituted with 0–3 $R^{4a}$, $C_3$–$C_{10}$ carbocycle substituted with 0–3 $R^{26}$, aryl substituted with 0–5 $R^{26}$, or 5–10 membered heterocycle containing from 1–4 heteroatoms selected from the group consisting of N, O, and S, and substituted with 0–3 $R^{27}$;

alternatively, $R^4$ and $R^5$ may be joined together with the carbon atom to which they are attached to form: $C_3$–$C_{10}$ carbocycle substituted with 0–3 $R^{26}$, or 5–10 membered heterocycle containing from 1–4 heteroatoms selected from the group consisting of N, O, and S, and substituted with 0–3 $R^{27}$;

$R^6$ is H, $C_1$–$C_4$ alkyl, $C_2$–$C_4$ alkenyl, aryl($C_1$–$C_3$ alkyl)-, or $C_1$–$C_4$ alkoxyalkyl;

$R^8$ is phenyl substituted with one $R^{8a}$ and 0–2 $R^{8b}$, 5–6 membered heteroaryl group comprising carbon atoms and 1, 2, or 3 heteroatoms selected from N, O, S, SO, and $SO_2$, wherein said 5–6 membered heteroaryl is substituted with one $R^{8a}$ and 0–2 $R^{8b}$, 9–10 membered bicyclic carbocycle, wherein said 9–10 membered bicyclic carbocycle contains at least one aromatic ring, and is substituted with one $R^{8a}$ and 0–2 $R^{8b}$, or 9–10 membered bicyclic heterocycle comprising carbon atoms and 1, 2, or 3 heteroatoms selected from N, O, S, SO, and $SO_2$, wherein said 9–10 membered bicyclic heterocycle contains at least one aromatic ring, and substituted with one $R^{8a}$ and 0–2 $R^{8b}$;

each $R^{8a}$ is, independently at each occurrence, $C_1$–$C_6$ alkyl, F, Cl, Br, I, OH, —$CF_3$, —$OCF_3$, —$OCH_3$, —$OCH_2CH_3$, —$OCH(CH_3)_2$, —$OCH_2CH_2CH_3$, CN, $NO_2$, $NH_2$, $NH(C_1$–$C_3$ alkyl), $N(C_1$–$C_3$ alkyl$)_2$, —$C(=NH)NH_2$, —$C(=O)NH_2$, —$CH_2NH_2$, —$CH_2NH(C_1$–$C_3$ alkyl), —$CH_2N(C_1$–$C_3$ alkyl$)_2$, —$CH_2CH_2NH_2$, —$CH_2CH_2NH(C_1$–$C_3$ alkyl), —$CH_2CH_2N(C_{1-3}$ alkyl$)_2$, —$(CR^{18}R^{19})_tC(=NR^{18})NR^{17}R^{19}$, —$(CR^{18}R^{19})_tC(=NR^{17})NR^{18}R^{19}$, —$(CR^{18}R^{19})_tNHC(=NR^{18})NR^{17}R^{19}$, —$(CR^{18}R^{19})_tNHC(=NR^{17})NR^{18}R^{19}$, —$(CR^{18}R^{19})_tNR^{17}C(=NR^{18})NR^{18}R^{19}$, —$(CR^{18}R^{19})_tNR^{18}CH(=NR^{17})$, —$(CR^{18}R^{19})_tNR^{17}CH(=NR^{18})$, —$(CR^{18}R^{19})_tC(=O)H$, —$(CR^{18}R^{19})_tC(=O)R^{20}$, —$(CR^{18}R^{19})_tNR^{18}R^{19}$, —$(CR^{18}R^{19})_tC(=O)NR^{18}R^{19}$, —$(CR^{18}R^{19})_tNR^{19}C(=O)R^{20}$, —$(CR^{18}R^{19})_tOR^{20}$, —$(CR^{18}R^{19})_tS(=O)NR^{18}R^{19}$, —$(CR^{18}R^{19})_tS(=O)_2NR^{18}R^{19}$, —$(CR^{18}R^{19})_tNR^{19}S(=O)R^{20}$, —$(CR^{18}R^{19})_tNR^{19}S(=O)_2R^{20}$, —$(CR^{18}R^{19})_tSR^{20}$, —$(CR^{18}R^{19})_tS(=O)R^{20}$, or —$(CR^{18}R^{19})_tS(=O)_2R^{20}$;

provided that the moiety $S(=O)R^{20}$ forms other than $S(=O)H$, and the moiety $S(=O)_2R^{20}$ forms other than $S(=O)_2H$;

each $R^{8b}$ is, independently at each occurrence, H, halogen, $C_1$–$C_4$ alkyl, $C_1$–$C_4$ alkoxy, OH, —$CF_3$, —$OCF_3$, CN, $NO_2$, —$C(=O)NH_2$, $NH_2$, $NH(C_1$–$C_3$ alkyl), or —$N(C_1$–$C_3$ alkyl$)_2$;

each $R^{14}$ is, independently at each occurrence, H, $C_1$–$C_6$ alkyl, $C_2$–$C_6$ alkenyl, $C_2$–$C_6$ alkynyl, OH, $C_1$–$C_6$ alkoxy, $NH_2$, $NH(C_1$–$C_3$ alkyl), $N(C_1$–$C_3$ alkyl$)_2$, $C_2$–$C_6$ alkoxyalkyl-, $C_2$–$C_6$ alkylaminoalkyl-, or $C_3$–$C_6$ dialkylaminoalkyl-;

each $R^{15}$ is, independently at each occurrence, H, F, methyl, ethyl, or propyl;

alternatively, —$CR^{15}R^{15}$— forms a gem disubstituted cyclopropyl, cyclobutyl, cyclopentyl, or cyclohexyl group;

each $R^{16}$ is, independently at each occurrence, H, methyl, ethyl, propyl, butyl, phenyl, or benzyl;

each $R^{17}$ is, independently at each occurrence, H, OH, $C_1$–$C_6$ alkyl, —$OR^{17a}$, —$C(=O)OR^{17a}$, —$OC(=O)R^{17a}$, —$OC(=O)OR^{17a}$, —$C(=O)R^{17a}$, —$CH_2OC(=O)R^{17a}$, —$C(=O)SR^{17a}$, —$C(=S)OR^{17a}$, —$C(=S)SR^{17a}$, phenyl, phenyl-($C_1$–$C_3$ alkyl)-, $C_1$–$C_4$ alkyl-$C(=O)O$—($C_1$–$C_4$ alkyl)-$OC(=O)$—, aryl-$C(=O)O$—($C_1$–$C_4$ alkyl)-$OC(=O)$—, $C_1$–$C_6$ alkyl-$NH_2$—$C(=O)$—, or phenyl-$NH_2$—$C(=O)$—;

each $R^{17a}$ is, independently at each occurrence, $C_1$–$C_6$ alkyl substituted with 0–3 $R^{17b}$, $C_2$–$C_6$ alkenyl substituted with 0–3 $R^{17b}$, $C_3$–$C_6$ alkynyl substituted with 0–3 $R^{17b}$, $C_3$–$C_8$ carbocycle substituted with 0–3 $R^{17b}$, $C_3$–$C_8$ carbocycle($C_1$–$C_3$ alkyl)-substituted with 0–3 $R^{17b}$, aryl substituted with 0–3 $R^{17b}$, aryl($C_1$–$C_3$ alkyl)- substituted with 0–3 $R^{17b}$, 5–6 membered heterocycle consisting of carbon atoms and 1–4 heteroatoms selected from the group: O, S, and N, and substituted with 0–3 $R^{17b}$; or 5–6 membered heterocycle-($C_1$–$C_3$ alkyl)- group consisting of carbon atoms and 1–4 heteroatoms selected from the group: O, S, and N, and substituted with 0–3 $R^{17b}$;

each $R^{17b}$ is, independently at each occurrence, H, halogen, —$CF_3$, —$OCF_3$, $C_1$–$C_6$ alkyl, OH, $C_1$–$C_6$ alkoxy, CN, $NO_2$, $NH_2$, $N(CH_3)_2$, $CO_2H$, —$C(=O)O(C_1$–$C_6$ alkyl), or —$OC(=O)$aryl;

each $R^{18}$ is, independently at each occurrence, H or $C_1$–$C_4$ alkyl;

alternatively, $R^{17}$ and $R^{18}$ combine to form —$C(=O)OC(=O)$—, —$C(=O)O$—, —$C(=O)S$—, or —$C(=S)O$—;

each $R^{19}$ is, independently at each occurrence, H or $C_1$–$C_4$ alkyl;

alternatively, $R^{18}$ and $R^{19}$, when attached to the same nitrogen, combine to form a 5–10 membered heterocycle consisting of one nitrogen atom, carbon atoms and 0–2 additional heteroatoms selected from the group consisting of N, O, and S;

each $R^{20}$ is, independently at each occurrence, H or $C_1$–$C_6$ alkyl;

each $R^{21}$ is, independently at each occurrence, H, $C_1$–$C_4$ alkyl, aryl, or aryl($C_1$–$C_3$ alkyl)-;

each $R^{21a}$ is, independently at each occurrence, H, $C_1$–$C_4$ alkyl, aryl, aryl($C_1$–$C_3$ alkyl)-, or $C_1$–$C_4$ haloalkyl;

each $R^{22}$ is, independently at each occurrence, H, $C_1$–$C_8$ alkyl substituted with 0–3 $R^{25}$, $C_2$–$C_8$ alkenyl substituted with 0–3 $R^{25}$, $C_2$–$C_8$ alkynyl substituted with 0–3 $R^{25}$, $C_3$–$C_{10}$ carbocycle substituted with 0–3 $R^{26}$, aryl substituted with 0–5 $R^{26}$, or 5–10 membered heterocycle containing from 1–4 heteroatoms selected from the group consisting of N, O, and S, and substituted with 0–3 $R^{27}$;

provided when $R^4$ or $R^{4a}$ are —OC(=O)OR$^{22}$, —S(=O) R$^{22}$, —S(=O)$_2$R$^{22}$, —NR$^{24}$S(=O)R$^{22}$, or —NR$^{24}$S(=O)$_2$ R$^{22}$, then R$^{22}$ is not H;

each $R^{23}$ is, independently at each occurrence, H, $C_1$–$C_4$ alkyl, $C_2$–$C_4$ alkenyl, or $C_2$–$C_4$ alkynyl;

alternatively, $R^{22}$ and $R^{23}$, when attached to the same nitrogen, combine to form a 5–6 membered heterocycle consisting of one nitrogen atom, carbon atoms and 0–1 additional heteroatoms selected from the group consisting of —N(R$^{24}$)—, O, and S;

each $R^{24}$ is, independently at each occurrence, H or $C_1$–$C_4$ alkyl;

each $R^{25}$ is, independently at each occurrence, H, halo, —CF$_3$, —OCF$_3$, OH, CN, NO$_2$, $C_1$–$C_4$ haloalkyl, $C_{1-8}$ alkoxy, ($C_{1-4}$ haloalkyl)oxy, $C_3$–$C_{10}$ carbocycle substituted with 0–3 $R^{26}$, aryl substituted with 0–5 $R^{26}$, or 5–10 membered heterocycle containing from 1–4 heteroatoms selected from the group consisting of N, O, and S, and substituted with 0–3 $R^{27}$;

each $R^{26}$ is, independently at each occurrence, H, OH, halo, CN, NO$_2$, —CF$_3$, —SO$_2$R$^{28}$, NR$^{29}$R$^{30}$, $C_1$–$C_6$ alkyl, $C_2$–$C_6$ alkenyl, $C_2$–$C_6$ alkynyl, $C_3$–$C_6$ cycloalkyl, $C_1$–$C_4$ haloalkyl, $C_1$–$C_4$ haloalkyl-oxy-, $C_1$–$C_4$ alkyloxy-, $C_1$–$C_4$ alkylthio-, $C_1$–$C_4$ alkyl-C(=O)—, or $C_1$–$C_4$ alkyl-C(=O)NH—;

each $R^{27}$ is, independently at each occurrence, H, OH, halo, —CF$_3$, —SO$_2$R$^{28}$, NR$^{29}$R$^{30}$, or $C_1$–$C_4$ alkyl;

each $R^{28}$ is, independently at each occurrence, $C_1$–$C_4$ alkyl, phenyl, or benzyl;

each $R^{29}$ is, independently at each occurrence, H, —SO$_2$R$^{28}$, —C(=O)R$^{28}$, $C_1$–$C_4$ alkyl, phenyl, or benzyl;

each $R^{30}$ is, independently at each occurrence, H or $C_1$–$C_4$ alkyl; and t, at each occurrence, is selected from 0, 1, 2, and 3.

In a second aspect, the present invention includes compounds of Formula (I) or a stereoisomer or pharmaceutically acceptable salt form thereof, wherein:

$A^1$ is —CH$_2$— or —CH$_2$CH$_2$—; wherein $A^1$ is optionally substituted with 0–2 $R^{14}$;

$R^1$ is H or $C_1$–$C_6$ alkyl;

$R^3$ is H, F, Cl, Br, or $C_1$–$C_6$ alkyl;

$R^5$ is H, halo, $C_1$–$C_4$ haloalkyl, $C_1$–$C_4$ alkyl, $C_2$–$C_4$ alkenyl, or $C_2$–$C_4$ alkynyl;

each $R^{17}$ is, independently at each occurrence, H, OH, $C_1$–$C_6$ alkyl, $C_1$–$C_6$ alkyl-O—, $C_1$–$C_6$ alkyl-C(=O)—, $C_1$–$C_4$ alkyl-OC(=O)—, aryl-O—, aryl-OC(=O)—, aryl-CH$_2$—C(=O)—, phenyl, phenyl-($C_1$–$C_3$ alkyl)-, $C_1$–$C_4$ alkyl-C(=O)O—($C_1$–$C_4$ alkyl)-OC(=O)—, aryl-C(=O)O—($C_1$–$C_4$ alkyl)-OC(=O)—, $C_1$–$C_6$ alkyl-NH$_2$—C(=O)—, or phenyl-NH$_2$—C(=O)—;

each $R^{18}$ is, independently at each occurrence, H or $C_1$–$C_4$ alkyl;

each $R^{19}$ is, independently at each occurrence, H or $C_1$–$C_4$ alkyl; and alternatively, $R^{18}$ and $R^{19}$, when attached to the same nitrogen, combine to form a 5–10 membered heterocyclic ring consisting of one nitrogen atom, carbon atoms and 0–2 additional heteroatoms selected from the group consisting of N, O, and S.

In a third aspect, the present invention includes compounds of Formula (Ia):

(Ia)

or a stereoisomer or pharmaceutically acceptable salt form thereof, wherein:

X is —C(=O)NH—CH$_2$—R$^8$, —S(=O)$_2$NH—CH$_2$—R$^8$, —CR$^{15}$R$^{15}$—NHC(=O)—CH$_2$—R$^8$, or —CR$^{15}$R$^{15}$—NHS(=O)$_2$—CH$_2$—R$^8$;

$R^2$ is H, —C(=O)R$^{2a}$, —C(=O)OR$^{2a}$, —C(=O) NHR$^{2a}$, —S(=O)R$^{2a}$, —S(=O)$_2$R$^{2a}$, —S(=O)$_2$NHR$^{2a}$, $C_1$–$C_6$ alkyl substituted with 0–3 $R^{2b}$, $C_2$–$C_6$ alkenyl substituted with 0–3 $R^{2b}$, $C_2$–$C_6$ alkynyl substituted with 0–3 $R^{2b}$, $C_3$–$C_6$ carbocycle substituted with 0–3 $R^{2c}$, aryl substituted with 0–3 $R^{2c}$, or 5–6 membered heterocycle consisting of carbon atoms and 1–4 heteroatoms selected from the group: O, S, and N, and substituted with 0–3 $R^{2c}$;

each $R^{2b}$ is, independently at each occurrence, H, F, Cl, Br, I, NO$_2$, CN, —NCS, —CF$_3$, —OCF$_3$, —CH$_3$, —CH$_2$CH$_3$, —CH(CH$_3$)$_2$, —OCH$_3$, =O, OH, CO$_2$H, NH$_2$, —NH(CH$_3$), N(CH$_3$)$_2$, CO$_2$R$^{21}$, —C(=O)NR$^{21}$ R$^{21}$, —NHC(=O)R$^{21}$, —NR$^{21}$R$^{21}$, —NHSO$_2$R$^{21}$, —SO$_2$R$^{21}$, —SO$_2$NR$^{21}$ R$^{21}$, —OR$^{21a}$, —SR$^{21a}$, —C(=O)R$^{21a}$, —S(=O)R$^{21a}$, $C_1$–$C_4$ haloalkyl, $C_1$–$C_4$ haloalkoxy, $C_3$–$C_6$ carbocycle substituted with 0–3 $R^{2c}$, aryl substituted with 0–3 $R^{2c}$, or 5–6 membered heterocycle consisting of carbon atoms and 1–4 heteroatoms selected from the group: O, S, and N, and substituted with 0–3 $R^{2c}$;

each $R^{2c}$ is, independently at each occurrence, H, F, Cl, Br, I, NO$_2$, CN, —NCS, —CF$_3$, —OCF$_3$, —CH$_3$, —OCH$_3$, =O, OH, CO$_2$H, NH$_2$, NH(CH$_3$), N(CH$_3$)$_2$, CO$_2$R$^{21}$, —C(=O)NR$^{21}$R$^{21}$, —NHC(=O)R$^{21}$, —NR$^{21}$ R$^{21}$, —NHSO$_2$R$^{21}$, —SO$_2$R$^{21}$, —SO$_2$NR$^{21}$ R$^{21}$, —OR$^{21a}$, —SR$^{21a}$, —C(=O)R$^{21a}$, —S(=O)R$^{21a}$, $C_1$–$C_4$ haloalkyl, $C_1$–$C_4$ haloalkoxy, or $C_1$–$C_4$ alkyl;

$R^3$ is H, F, Cl, Br, methyl, ethyl, propyl, or butyl;

$R^4$ is H, halo, —CF$_3$, —OCF$_3$, OH, CN, NO$_2$, —OR$^{22}$, —SR$^{22}$, —NR$^{22}$R$^{23}$, —C(=O)R$^{22}$, —C(=O)NR$^{22}$R$^{23}$, —NR$^{24}$C(=O)R$^{22}$, —NR$^{24}$C(=O)NR$^{22}$R$^{23}$, —NR$^{24}$C (=O)NR$^{24}$C(=O)R$^{22}$, —C(=O)OR$^{22}$, —OC(=O)R$^{22}$, —OC(=O)OR$^{22}$, —NR$^{24}$C(=O)OR$^{22}$, —OC(=O) NR$^{22}$R$^{23}$, —S(=O)R$^{22}$, —S(=O)$_2$R$^{22}$, —S(=O)NR$^{22}$R$^{23}$, —S(=O)$_2$NR$^{22}$R$^{23}$, —NR$^{24}$S(=O)$_2$NR$^{22}$R$^{23}$, —NR$^{24}$S (=O)R$^{22}$, —NR$^{24}$S(=O)$_2$R$^{22}$, $C_1$–$C_4$ haloalkyl, $C_1$ $C_6$ alkoxy, ($C_1$–$C_4$ haloalkyl)oxy, $C_1$–$C_6$ alkyl, $C_2$–$C_6$ alkenyl, $C_2$–$C_6$ alkynyl, or $C_1$–$C_3$ alkyl substituted with $R^{4a}$;

$R^{4a}$ is —NR$^{22}$R$^{23}$, —C(=O)NR$^{22}$R$^{23}$, —NR$^{24}$C(=O) R$^{22}$, —NR$^{24}$C(=O)NR$^{22}$R$^{23}$, —NR$^{24}$C(=O)NR$^{24}$C(=O) R$^{22}$, —C(=O)OR$^{22}$, —NR$^{24}$C(=O)OR$^{22}$, —NR$^{24}$S(=O)$_2$ NR$^{22}$R$^{23}$, or —NR$^{24}$S(=O)$_2$R$^{22}$;

$R^8$ is phenyl substituted with one $R^{8a}$ and 0–1 $R^{8b}$, pyridyl substituted with one $R^{8a}$ and 0–1 $R^{8b}$, naphthyl substituted with one $R^{8a}$ and 0–1 $R^{8b}$, quinolinyl substituted with one $R^{8a}$ and 0–1 $R^{8b}$, isoquinolinyl substituted with one $R^{8a}$ and 0–1 $R^{8b}$, phthalazinyl substituted with one $R^{8a}$ and 0–1 $R^{8b}$, quinazolinyl substituted with one $R^{8a}$ and 0–1 $R^{8b}$, indolyl substituted with one $R^{8a}$ and 0–1 $R^{8b}$, isoindolyl substituted with one $R^{8a}$ and 0–1 $R^{8b}$, indolinyl substituted with one $R^{8a}$ and 0–1 $R^{8b}$, 1H-indazolyl substituted with one $R^{8a}$ and 0–1 $R^{8b}$, or benzimidazolyl substituted with one $R^{8a}$ and 0–1 $R^{8b}$;

each $R^{8a}$ is, independently at each occurrence, —C(=NH)NH$_2$, —C(=O)NH$_2$, —NHC(=NH)NH$_2$, —NHCH(=NH), —NH$_2$, —CH$_2$C(=NH)NH$_2$, —CH$_2$NHC(=NH)NH$_2$, —CH$_2$NHCH(=NH), —CH$_2$NH$_2$, or —CH$_2$C(=O)NH$_2$;

each $R^{15}$ is, independently at each occurrence, H, F, or methyl;

alternatively, —CR$^{15}$R$^{15}$— forms a gem disubstituted cyclopropyl group;

each $R^{17}$ is, independently at each occurrence, H, OH, or $C_1$–$C_4$ alkyl;

each $R^{18}$ is, independently at each occurrence, H or $C_1$–$C_4$ alkyl;

each $R^{19}$ is, independently at each occurrence, H or $C_1$–$C_4$ alkyl;

each $R^{22}$ is, independently at each occurrence, H, $C_1$–$C_4$ alkyl, $C_2$–$C_4$ alkenyl, $C_3$–$C_6$ cycloalkyl, phenyl substituted with 0–5 $R^{26}$, or 5–6 membered heterocycle containing from 1–4 heteroatoms selected from the group consisting of N, O, and S, and substituted with 0–3 $R^{27}$;

provided when $R^4$ or $R^{4a}$ are —OC(=O)OR$^{22}$, —S(=O)R$^{22}$, —S(=O)$_2$R$^{22}$, —NR$^{24}$S(—O)R$^{22}$, or —NR$^{24}$S(=O)$_2$R$^{22}$, then $R^{22}$ is not H;

each $R^{23}$ is, independently at each occurrence, H or $C_1$–$C_4$ alkyl;

alternatively, $R^{22}$ and $R^{23}$, when attached to the same nitrogen, combine to form a 5–6 membered heterocycle consisting of one nitrogen atom, carbon atoms and 0–1 additional heteroatoms selected from the group consisting of —N(R$^{24}$)— and O;

each $R^{26}$ is, independently at each occurrence, H, OH, F, Cl, CN, NO$_2$, CF$_3$, —SO$_2$CH$_3$, —SO$_2$CH$_2$CH$_3$, NH$_2$, NH(CH$_3$), N(CH$_3$)$_2$, methyl, ethyl, propyl, allyl, —OCF$_3$, methoxy, ethoxy, —SCH$_3$, —SCH$_2$CH$_3$, —C(=O)CH$_3$, —C(=O)CH$_2$CH$_3$, —NHC(=O)CH$_3$, or —NHC(=O)CH$_2$CH$_3$; and t is 0 or 1.

In a fourth aspect, the present invention includes compounds of Formula (Ib):

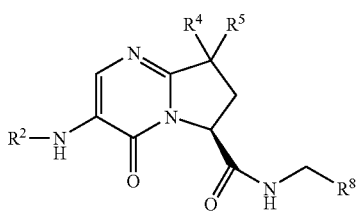

(Ib)

or a stereoisomer or pharmaceutically acceptable salt form thereof, wherein:

$R^2$ is H, —C(=O)R$^{2a}$, —C(=O)OR$^{2a}$, —S(=O)$_2$R$^{2a}$, $C_1$–$C_6$ alkyl substituted with 0–3 $R^{2b}$, $C_2$–$C_6$ alkenyl substituted with 0–3 $R^{2b}$, $C_2$–$C_6$ alkynyl substituted with 0–3 $R^{2b}$, $C_3$–$C_6$ carbocycle substituted with 0–3 $R^{2c}$, aryl substituted with 0–3 $R^{2c}$, or 5–6 membered heterocycle consisting of carbon atoms and 1–4 heteroatoms selected from the group: O, S, and N, and substituted with 0–3 $R^{2c}$;

each $R^{2a}$ is, independently at each occurrence, H, $C_1$–$C_6$ alkyl substituted with 0–3 $R^{2b}$, $C_2$–$C_6$ alkenyl substituted with 0–3 $R^{2b}$, $C_2$–$C_6$ alkynyl substituted with 0–3 $R^{2b}$, $C_3$–$C_6$ carbocycle substituted with 0–3 $R^{2c}$, aryl substituted with 0–3 $R^{2c}$, or 5–6 membered heterocycle consisting of carbon atoms and 1–4 heteroatoms selected from the group: O, S, and N, and substituted with 0–3 $R^{2c}$;

provided when $R^2$ is —S(=O)R$^{2a}$ or —S(=O)$_2$R$^{2a}$, then $R^{2a}$ is not H;

each $R^{2b}$ is, independently at each occurrence, H, F, Cl, Br, I, NO$_2$, CN, —NCS, —CF$_3$, —OCF$_3$, —CH$_3$, —CH$_2$CH$_3$, —CH(CH$_3$)$_2$, —OCH$_3$, =O, OH, CO$_2$H, NH$_2$, NH(CH$_3$), N(CH$_3$)$_2$, CO$_2$R$^{21}$, —C(=O)NR$^{21}$R$^{21}$, —NHC(=O)R$^{21}$, —NR$^{21}$R$^{21}$, —NHSO$_2$R$^{21}$, —SO$_2$R$^{21}$, —SO$_2$NR$^{21}$R$^{21}$, OR$^{21a}$, —SR$^{21a}$, —C(=O)R$^{21a}$, —S(=O)R$^{21a}$, $C_1$–$C_4$ haloalkyl, $C_1$–$C_4$ haloalkoxy, $C_3$–$C_6$ carbocycle substituted with 0–3 $R^{2c}$, aryl substituted with 0–3 $R^{2c}$, or 5–6 membered heterocycle consisting of carbon atoms and 1–4 heteroatoms selected from the group: O, S, and N, and is substituted with 0–3 $R^{2c}$;

each $R^{2c}$ is, independently at each occurrence, H, F, Cl, Br, I, NO$_2$, CN, —NCS, —CF$_3$, —OCF$_3$, —CH$_3$, —OCH$_3$, =O, OH, CO$_2$H, NH$_2$, NH(CH$_3$), N(CH$_3$)$_2$, CO$_2$R$^{21}$, —C(=O)NR$^{21}$R$^{21}$, —NHC(=O)R$^{21}$, —NR$^{21}$R$^{21}$, —NHSO$_2$R$^{21}$, —SO$_2$R$^{21}$, —SO$_2$NR$^{21}$R$^{21}$, —OR$^{21a}$, —SR$^{21a}$, —C(=O)R$^{21a}$, —S(=O)R$^{21a}$, $C_1$–$C_4$ haloalkyl, $C_1$–$C_4$ haloalkoxy, or $C_1$–$C_4$ alkyl;

$R^4$ is H, F, Cl, Br, —CF$_3$, $C_2$–$C_4$ haloalkyl, $C_1$–$C_6$ alkyl, $C_2$–$C_6$ alkenyl, $C_2$–$C_6$ alkynyl, —NR$^{22}$R$^{23}$, —NR$^{24}$C(=O)R$^{22}$, —CH$_2$NR$^{22}$R$^{23}$, —CH$_2$C(=O)NR$^{22}$R$^{23}$, —CH$_2$NR$^{24}$C(=O)R$^{22}$, —CH$_2$NR$^{24}$C(=O)NR$^{22}$R$^{23}$, —CH$_2$C(=O)OR$^{22}$, —CH$_2$NR$^{24}$C(=O)OR$^{22}$, —CH$_2$NR$^{24}$S(=O)$_2$NR$^{22}$R$^{23}$, or —CH$_2$NR$^{24}$S(=O)$_2$R$^{22}$;

$R^5$ is H, methyl, ethyl, propyl, butyl, or allyl;

$R^8$ is phenyl substituted with —C(=NH)NH$_2$ and 0–1 $R^{8b}$;

$R^{8b}$ is H, F, Cl, Br, —CH$_3$, —OCH$_3$, —OH, —CF$_3$, —OCF$_3$, —CN, —NO$_2$, —C(=O)NH$_2$, —NH$_2$, —NH(CH$_3$), or —N(CH$_3$)$_2$;

each $R^{21}$ is, independently at each occurrence, H, methyl, ethyl, propyl, butyl, aryl, (aryl)methyl-, (aryl)ethyl-, or (aryl)propyl-;

each $R^{21a}$ is, independently at each occurrence, H, methyl, ethyl, propyl, butyl, aryl, (aryl)methyl-, (aryl)ethyl-, (aryl)propyl-, or $C_1$–$C_4$ haloalkyl;

each $R^{22}$ is, independently at each occurrence, H, methyl, ethyl, propyl, butyl, allyl, cyclopropyl, cyclobutyl, cyclopentyl, cyclohexyl, phenyl, pyridinyl, furanyl, thienyl, pyrrolyl, pyrazolyl, pyrazinyl, piperazinyl, piperidinyl, imidazolyl, imidazolidinyl, isoxazolyl, morpholinyl, oxazolyl, oxazolidinyl, or tetrahydrofuranyl;

provided when $R^4$ is —CH$_2$NR$^{24}$S(=O)$_2$R$^{22}$, then $R^{22}$ is not H;

each $R^{23}$ is, independently at each occurrence, H, methyl, ethyl, propyl, and butyl;

alternatively, $R^{22}$ and $R^{23}$, when attached to the same nitrogen, combine to form pyrrolidinyl, piperidinyl, morpholinyl, piperazinyl, or N-methylpiperazinyl; and each $R^{24}$ is, independently at each occurrence, H, methyl, ethyl, propyl, or butyl.

In a fifth aspect, the present invention includes compounds of Formula (Ic):

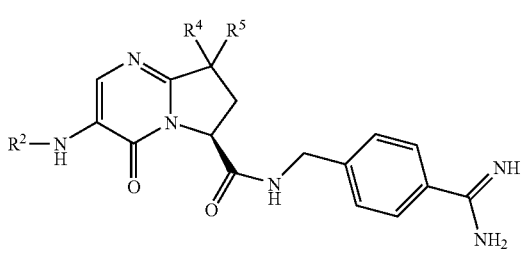

(Ic)

or a stereoisomer or pharmaceutically acceptable salt form thereof, wherein:

$R^2$ is H, —C(=O)$R^{2a}$, —C(=O)O$R^{2a}$, —S(=O)$_2R^{2a}$, methyl, ethyl, propyl, butyl, pentyl, hexyl, propenyl, butenyl, pentenyl, cyclopropyl, cyclobutyl, cyclopentyl, cyclohexyl, methyl substituted with $R^{2b}$, ethyl substituted with $R^{2b}$, propyl substituted with $R^{2b}$, butyl substituted with $R^{2b}$, pentyl substituted with $R^{2b}$, or phenyl substituted with 0–3 $R^{2c}$;

each $R^{2a}$ is, independently at each occurrence, methyl, ethyl, propyl, butyl, pentyl, hexyl, propenyl, butenyl, pentenyl, cyclopropyl, cyclobutyl, cyclopentyl, cyclohexyl, methyl substituted with $R^{2b}$, ethyl substituted with $R^{2b}$, propyl substituted with $R^{2b}$, butyl substituted with $R^{2b}$, pentyl substituted with $R^{2b}$, phenyl substituted with 0–3 $R^{2c}$, or naphthyl substituted with 0–3 $R^{2c}$;

each $R^{2b}$ is, independently at each occurrence, H, F, Cl, Br, I, NO$_2$, CN, —NCS, —CF$_3$, —OCF$_3$, —CH$_3$, —CH$_2$CH$_3$, —CH(CH$_3$)$_2$, —OCH$_3$, =O, OH, CO$_2$H, NH$_2$, NH(CH$_3$), N(CH$_3$)$_2$, CO$_2R^{21}$, —C(=O)NH$R^{21}$, —NHC(=O)$R^{21}$, —NH$R^{21}$, —NHSO$_2R^{21}$, —SO$_2R^{21}$, —SO$_2$NH$R^{21}$, —O$R^{21a}$, —S$R^{21a}$, —C(=O)$R^{21a}$, —S(=O)$R^{21a}$, or phenyl substituted with 0–3 $R^{2c}$;

each $R^{2c}$ is, independently at each occurrence, H, F, Cl, Br, I, NO$_2$, CN, —NCS, —CF$_3$, —OCF$_3$, —CH$_3$, —OCH$_3$, =O, OH, CO$_2$H, NH$_2$, NH(CH$_3$), N(CH$_3$)$_2$, CO$_2R^{21}$, —C(=O)NH$R^{21}$, —NHC(=O)$R^{21}$, —NH$R^{21}$, —NHSO$_2R^{21}$, —SO$_2R^{21}$, —SO$_2$NH$R^{21}$, —O$R^{21a}$, S$R^{21a}$, C(=O)$R^{21a}$, S(=O)$R^{21a}$, methyl, ethyl, propyl, or butyl;

$R^4$ is H, F, methyl, ethyl, propyl, allyl, piperidinyl, —N$R^{22}R^{23}$, —NHC(=O)$R^{22}$, —CH$_2$N$R^{22}R^{23}$, —CH$_2$C(=O)N$R^{22}R^{23}$, —CH$_2$NHC(=O)$R^{22}$, —CH$_2$NHC(=O)N$R^{22}R^{23}$, —CH$_2$C(=O)O$R^{22}$, or —CH$_2$NHS(=O)$_2R^{22}$;

$R^5$ is H, methyl, ethyl, propyl, or allyl;

each $R^{21}$ is, independently at each occurrence, H, methyl, ethyl, propyl, butyl, phenyl, benzyl, or phenethyl;

each $R^{21a}$ is, independently at each occurrence, H, methyl, ethyl, propyl, butyl, phenyl, benzyl, phenethyl, or —CF$_3$;

each $R^{22}$ is, independently at each occurrence, H, methyl, ethyl, propyl, allyl, cyclopropyl, cyclobutyl, cyclopentyl, cyclohexyl, or phenyl;

provided when $R^4$ is —CH$_2$NHS(=O)$_2R^{22}$, then $R^{22}$ is not H; and $R^{23}$ is H, methyl, ethyl, propyl, or butyl.

In a sixth aspect, the present invention provides a compound selected from Examples 1–43 or a stereoisomer or pharmaceutically acceptable salt form thereof.

In another embodiment of the present invention, when Z is =CH—, $R^8$ is phenyl or 5–6 membered heteroaryl, $R^{8a}$ is OH, F, Cl, Br, I, or —CF$_3$; and $R^{8b}$ is OH, F, Cl, Br, I, or —CF$_3$; then $R^{16}$ is H.

In a preferred embodiment $R^8$ is —C(=NH)NH$_2$ or —CH$_2$NH$_2$.

In a preferred embodiment $R^8$ is —C(=NH)NH$_2$.

In another embodiment the present invention provides a pharmaceutical composition comprising a pharmaceutically acceptable carrier and a therapeutically effective amount of at least one of the compounds of the present invention or a pharmaceutically acceptable salt or prodrug form thereof.

In another embodiment the present invention provides a method for modulation of the coagulation cascade comprising administering to a patient in need of such treatment a therapeutically effective amount of at least one of the compounds of the present invention or a pharmaceutically acceptable salt or prodrug form thereof.

In another embodiment the present invention provides a method for treating thromboembolic disorders comprising: administering to a patient in need of such treatment a therapeutically effective amount of at least one of the compounds of the present invention or a pharmaceutically acceptable salt or prodrug form thereof.

In another embodiment, the thromboembolic disorder is selected from the group consisting of arterial cardiovascular thromboembolic disorders, venous cardiovascular thromboembolic disorders, arterial cerebrovascular thromboembolic disorders, and venous cerebrovascular thromboembolic disorders.

In another embodiment, the thromboembolic disorder is selected unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, and (f) other procedures in which blood is exposed to an artificial surface that promotes thrombosis.

In another embodiment, the present invention provides a novel method of treating a patient in need of thromboembolic disorder treatment, comprising: administering a compound of the present invention or a pharmaceutically acceptable salt form thereof in an amount effective to treat a thromboembolic disorder.

In another embodiment, the present invention provides a method for treating a thromboembolic disorder, comprising: administering to a patient in need thereof a therapeutically effective amount of a first and additional therapeutic agent(s), wherein the first therapeutic agent is compound of Formula (I) or a pharmaceutically acceptable salt thereof and the additional therapeutic agent(s) are selected from an anti-coagulant agent, an anti-platelet agent, a thrombin inhibiting agent, a thrombolytic agent, and a fibrinolytic agent or a combination thereof.

In a preferred embodiment, the present invention provides a method for treating a thromboembolic disorder, wherein the second therapeutic agent is selected from warfarin, unfractionated heparin, low molecular weight heparin, synthetic pentasaccharide, hirudin, argatrobanas, aspirin, ibuprofen, naproxen, sulindac, indomethacin, mefenamate, droxicam, diclofenac, sulfinpyrazone, piroxicam, ticlopidine, clopidogrel, tirofiban, eptifibatide, abciximab, melagatran, disulfatohirudin, tissue plasminogen activator, modified tissue plasminogen activator, anistreplase, urokinase, and streptokinase.

In a preferred embodiment, the present invention provides a method for treating a thromboembolic disorder, wherein the additional therapeutic agent(s) are an anti-platelet agent or a combination thereof.

In a preferred embodiment, the present invention provides a method for treating a thromboembolic disorder, wherein the additional therapeutic agent(s) is the anti-platelet agent clopidogrel.

In another embodiment, the present invention provides a novel method, comprising: administering a compound of the present invention or a pharmaceutically acceptable salt form thereof in an amount effective to treat a thromboembolic disorder.

In another embodiment, the present invention provides a compound of the present invention for use in therapy.

In another embodiment, the present invention also provides the use of a compound of the present invention for the manufacture of a medicament for the treatment of a thromboembolic disorder.

In another embodiment, the present invention provides a novel method for treating a thromboembolic disorder, comprising: administering to a patient in need thereof a therapeutically effective amount of a first and second therapeutic agent, wherein the first therapeutic agent is compound of the present invention or a pharmaceutically acceptable salt thereof and the second therapeutic agent is at least one agent selected from a second factor Xa inhibitor, an anti-coagulant agent, an anti-platelet agent, a thrombin inhibiting agent, a thrombolytic agent, and a fibrinolytic agent.

In another preferred embodiment, the present invention provides a novel method, wherein the second therapeutic agent is at least one agent selected from warfarin, unfractionated heparin, low molecular weight heparin, synthetic pentasaccharide, hirudin, argatrobanas, aspirin, ibuprofen, naproxen, sulindac, indomethacin, mefenamate, droxicam, diclofenac, sulfinpyrazone, piroxicam, ticlopidine, clopidogrel, tirofiban, eptifibatide, abciximab, melagatran, disulfatohirudin, tissue plasminogen activator, modified tissue plasminogen activator, anistreplase, urokinase, and streptokinase.

In another preferred embodiment, the present invention provides a novel method, wherein the second therapeutic agent is at least one anti-platelet agent.

In another preferred embodiment, the present invention provides a novel method, wherein the anti-platelet agent is aspirin and clopidogrel.

In another preferred embodiment, the present invention provides a novel method, wherein the anti-platelet agent is clopidogrel.

In another embodiment, the present invention provides a novel article of manufacture, comprising:
(a) a first container;
(b) a pharmaceutical composition located within the first container, wherein the composition, comprises: a first therapeutic agent, comprising: a compound of the present invention or a pharmaceutically acceptable salt form thereof; and,
(c) a package insert stating that the pharmaceutical composition can be used for the treatment of a thromboembolic disorder.

In another preferred embodiment, the present invention provides a novel article of manufacture, further comprising:
(d) a second container;

wherein components (a) and (b) are located within the second container and component (c) is located within or outside of the second container.

In another embodiment, the present invention provides a novel article of manufacture, comprising:
(a) a first container;
(b) a pharmaceutical composition located within the first container, wherein the composition, comprises: a first therapeutic agent, comprising: a compound of the present invention or a pharmaceutically acceptable salt form thereof; and,
(c) a package insert stating that the pharmaceutical composition can be used in combination with a second therapeutic agent to treat a thromboembolic disorder.

In another preferred embodiment, the present invention provides a novel article of manufacture, further comprising:
(d) a second container;

wherein components (a) and (b) are located within the second container and component (c) is located within or outside of the second container.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

Definitions

The compounds herein described have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Geometric isomers of double bonds such as olefins and C=N double bonds can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention. All tautomers of shown or described compounds are also considered to be part of the present invention.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^{2b}$, $R^{8b}$, etc.) occurs more than one time in any constituent or formula for a compound, its definition at each occurrence is independent of its definition at every other occurrence. Thus, for example, if a group is shown to be substituted with 0–3 $R^{2b}$, then said group may optionally be substituted with up to three $R^{2b}$ groups and $R^{2b}$ at each occurrence is selected independently from the definition of $R^{2b}$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" or "alkylene" is intended to include both branched and straight-chain saturated aliphatic hydrocarbon groups having the specified number of carbon atoms. For example, "$C_1$–$C_{10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$–$C_6$ alkyl" denotes alkyl having 1 to 6 carbon atoms. Examples of alkyl include, but are not limited to, methyl, ethyl, n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl.

"Alkenyl" or "alkenylene" is intended to include hydrocarbon chains of either a straight or branched configuration having the specified number of carbon atoms and one or more unsaturated carbon-carbon bonds which may occur in any stable point along the chain. For example, "$C_2$–$C_6$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either a straight or branched configuration and one or more carbon-carbon triple bonds which may occur in any stable point along the chain. For example, "$C_2$–$C_6$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

"Cycloalkyl" is intended to include saturated ring groups, having the specified number of carbon atoms. For example, "$C_3$–$C_6$ cycloalkyl" denotes such as cyclopropyl, cyclobutyl, cyclopentyl, or cyclohexyl.

"Alkoxy" or "alkyloxy" represents an alkyl group as defined above with the indicated number of carbon atoms attached through an oxygen bridge. For example, "$C_1$–$C_6$ alkoxy" (or alkyloxy), is intended to include $C_1$, $C_2$, $C_3$, $C_4$, $C_5$, and $C_6$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. Similarly, "alkylthio" or "thioalkoxy" represents an alkyl group as defined above with the indicated number of carbon atoms attached through a sulphur bridge; for example methyl-S—, ethyl-S—, and the like.

"Halo" or "halogen" as used herein refers to fluoro, chloro, bromo, and iodo; and "counterion" is used to represent a small, negatively charged species such as chloride, bromide, hydroxide, acetate, sulfate, and the like.

"Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" which is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$–$C_6$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, pentafluorothoxy, and the like. Similarly, "haloalkylthio" or "thiohaloalkoxy" represents a haloalkyl group as defined above with the indicated number of carbon atoms attached through a sulphur bridge; for example trifluoromethyl-S—, pentafluoroethyl-S—, and the like.

As used herein, "carbocycle" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin). Preferred carbocycles, unless otherwise specified, are cyclopropyl, cyclobutyl, cyclopentyl, cyclohexyl, phenyl, and indanyl.

As used herein, the term "heterocycle" or "heterocyclic group" is intended to mean a stable 5, 6, or 7-membered monocyclic or bicyclic or 7, 8, 9, 10, 11, 12, 13, or 14-membered bicyclic heterocyclic ring which is saturated, partially unsaturated or fully unsaturated, and which consists of carbon atoms and 1, 2, 3 or 4 heteroatoms independently selected from the group consisting of N, O and S; and including any bicyclic group in which any of the above-defined heterocyclic rings is fused to a benzene ring. The nitrogen and sulfur heteroatoms may optionally be oxidized to —NO—, —SO—, or —$SO_2$—. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" or "heteroaryl" is intended to mean a stable 5, 6, or 7-membered monocyclic or bicyclic or 7, 8, 9, or 10-membered bicyclic heterocyclic aromatic ring which consists of carbon atoms and 1, 2, 3, or 4 heteroatoms independently selected from the group consisting of N, NH, O and S. It is to be noted that total number of S and O atoms in the aromatic heterocycle is not more than 1.

Examples of heterocycles include, but are not limited to, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, imidazolopyridinyl, 1H-indazolyl, indolenyl, indolinyl, indolizinyl, indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolopyridinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thiazolopyridinyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Preferred 5 to 10 membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazolyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Preferred 5 to 6 membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazolyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9 or 10-membered heterocyclic ring system which contains two fused rings and consists of carbon atoms and 1, 2, 3, or 4 heteroatoms independently selected from the group consisting of N, O and S. Of the two fused rings, one ring is a 5 or 6-membered monocyclic aromatic ring comprising a 5 membered heteroaryl ring, a 6-membered heteroaryl ring or a benzo ring, each fused to a second ring. The second ring is a 5 or 6 membered monocyclic ring which is saturated, partially unsaturated, or unsaturated, and comprises a 5 membered heterocycle, a 6 membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinoline, 2,3-dihydrobenzofuranyl, chromanyl, 1,2,3,4-tetrahydro-quinoxaline, and 1,2,3,4-tetrahydro-quinazoline.

As used herein, the term "bicyclic carbocycle" or "bicyclic carbocyclic group" is intended to mean a stable 9 or 10-membered carbocyclic ring system which contains two fused rings and consists of carbon atoms. Of the two fused rings, one ring is a benzo ring fused to a second ring; and the second ring is a 5 or 6 membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

As used herein, the term "aryl", "$C_6$–$C_{10}$ aryl" or "aromatic residue", is intended to mean an aromatic moiety containing, if specified, the specified number of carbon atoms; for example phenyl or naphthyl. Unless otherwise specified, "aryl", "$C_{6–C10}$ aryl" or "aromatic residue" may be unsubstituted or substituted with 0 to 3 groups selected from H, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs of the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Synthesis

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley and Sons, 1991). All references cited herein are hereby incorporated in their entirety herein by reference.

Synthesis of Compounds 1.13, 2.3, 2.6, 2.9, 2.12, 2.14, 3.2, 3.5, 3.7, 4.5, and 4.6

Schemes 1 to 4 illustrate the synthesis of compounds of structure 1.13, 2.3, 2.6, 2.9, 2.12, 2.14, 3.2, 3.5, 3.7, 4.5, and 4.6. In Schemes 1 to 4, P is a nitrogen protecting group, and R is a standard leaving group for carboxylic acids, wherein such protecting and leaving groups are known to one skilled in the art.

The synthesis of inhibitor 1.13 is depicted in Scheme 1. An intermediate in this synthesis, bicyclic pyrimidinone 1.9 (n=1), is prepared as previously described by Webber et al. (Webber, S. E.; Dragovich, P. S.; Littlefield, E. S.; Marakovits, J. T.; Babine, R. E. WO 99/31122) and is described in the scheme. Lactam 1.1 (n=0-3) is protected as ester 1.2, which is subsequently converted to thiolactam 1.3 by treatment with Lawesson's reagent. Thiolactam 1.3 is alkylated with MeI to afford 1.4, which is displaced with ammonium chloride providing amidine 1.5. Compound 1.5 is condensed with dimethyl methoxymethylenemalonate to afford bicyclic pyrimidinone 1.6. The methyl ester functionality of ester 1.6 is cleaved with aqueous base to afford acid 1.7, which is then subjected to a Curtius rearrangement using diphenylphosphoryl azide and a suitable alcohol to afford carbamate 1.8. At this point, an $R^1$ substituent may be introduced via NaH-promoted alkylation of the carbamate nitrogen and the R substituent of the ester may be modified or converted to the corresponding amide via standard (EDCI/HOAT) amide coupling of the corresponding acid. This compound can then be deprotonated with strong base (such as LiHMDS or LDA), and the resultant anion reacted with suitable electrophiles. In this way, one or two electrophiles (reaction with $R^3$—X and $R^4$—X) may be introduced to give substituted bicyclic pyrimidinone 1.7. At this point, substituents $R^3$ and $R^4$ of compound 1.8 may optionally be modified, followed by deprotection to reveal carboxylic acid 1.9. Peptide coupling of acid 1.10 with various amines (1.11) affords amide 1.12. At this point, the R-derived carbamate functionality is cleaved. Optionally, $R^1$, $R^3$, and $R^4$ functionality may be modified and $R^2$ may be introduced to afford inhibitor 1.13.

Inhibitor 2.3 is prepared by deprotonation of lactam 2.1 (n=0–3) and reaction with a suitable electrophile(s) to provide compound 2.2, either monosubstituted or disubstituted, followed by a reaction sequence similar to the preparation of inhibitor 1.13. Similarly, inhibitor 2.6 is prepared beginning with cyclic amine 2.4 (N=0–3), which is made according to the chemistry described by Sardina et al. (Blanco, M. et al., *J. Org. Chem.* 1999, 64, 8786–8793). Cyclic amine 2.4 (n=0–3) is oxidized with ruthenium oxide in a two-phase system (Yoshifuji, S. et al., *Chem. Pharma. Bull.* 1986, 34, 3873–3878.) to the corresponding lactam 2.5. Lactam 2.5 (n=1) may also be prepared according to chemistry developed by Hruby, V. J. et al. (Soloshonok, V. A., Cai, C., Hruby, V. J. *Org. Lett.* 2000, 2, 747–750). Following chemistry described above, lactam 2.5 is converted into inhibitor 2.6.

Inhibitor 2.9 is prepared analogously to inhibitor 1.13 from piperazinone 2.8. Compound 2.8 is prepared via reductive amination of piperazinone 2.7, which is prepared according to the chemistry developed by Aebischer, B. et al. (*Helv. Chim. Acta* 1989, 72, 1043–51). Inhibitor 2.12 is prepared from bicyclic pyrimidinone 2.11 via chemistry analogous to the preparation of inhibitor 1.13. Intermediate 2.11 in turn is prepared via a condensation of amidine 1–5 and methylene malonate 2.10 followed by N-bromosuccinimide-promoted unsaturation. Compound 2.11 is prepared following chemistry described by Veale, C. A. et al. (*J. Org. Chem.* 1993, 58, 4490–4493.). Inhibitor 2.14 is prepared from morpholinone 2.13 via chemistry analogous to the preparation of inhibitor 1.13. Intermediate 2.13 is prepared via a condensation of CbzSerOtBu and methyl bromoacetate.

Syntheses of inhibitors 3.2, 3.5, and 3.7 are depicted in Scheme 3. Inhibitor 3.2 is prepared from bicyclic pyrimidinone 3.1 via chemistry analogous to the preparation of inhibitor 1.13. Intermediate 3.1 in turn is prepared via deprotonation of intermediate 1.8 with a base such as LiHMDS, followed by electrophilic quench with $R^{12}$—X. Inhibitor 3.5 (where n=0, 1, or 2) is prepared from bicyclic pyrimidinone 3.4 via chemistry analogous to the preparation of inhibitor 1.13. Intermediate 3.4 is prepared by deprotonation of intermediate 3.3 with strong base followed by electrophilic quench with $R^{13}$—X and $R^4$—X. Keto intermediate 3.3 is prepared from intermediate 1.8 via strong base deprotonation followed by treatment with an electrophilic oxygen source such as $O_2$, MoOPH, or Davis' oxaziridine. The resulting alcohol is oxidized to afford 3.3. Inhibitor 3.7 is prepared from intermediate 3.6 via chemistry analogous to the preparation of inhibitor 1.13. Intermediate 3.6 is prepared via deoxygenation of intermediate 3.4 by treatment with reagents such as trifluoroacetic acid and triethylsilane.

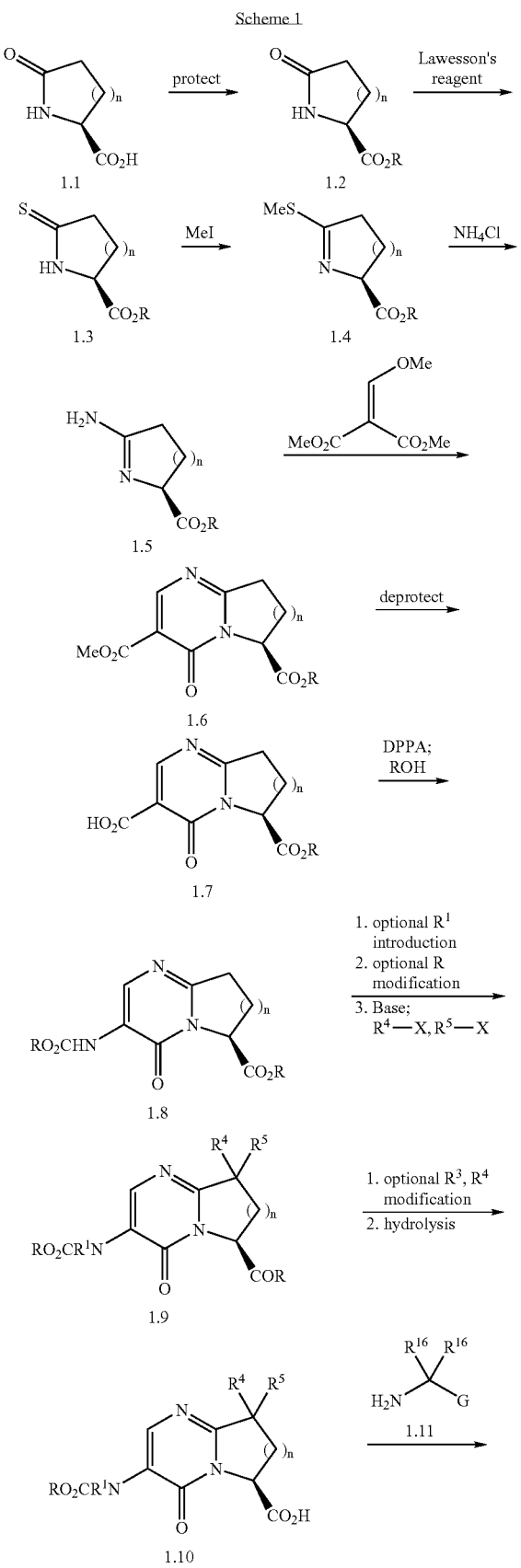

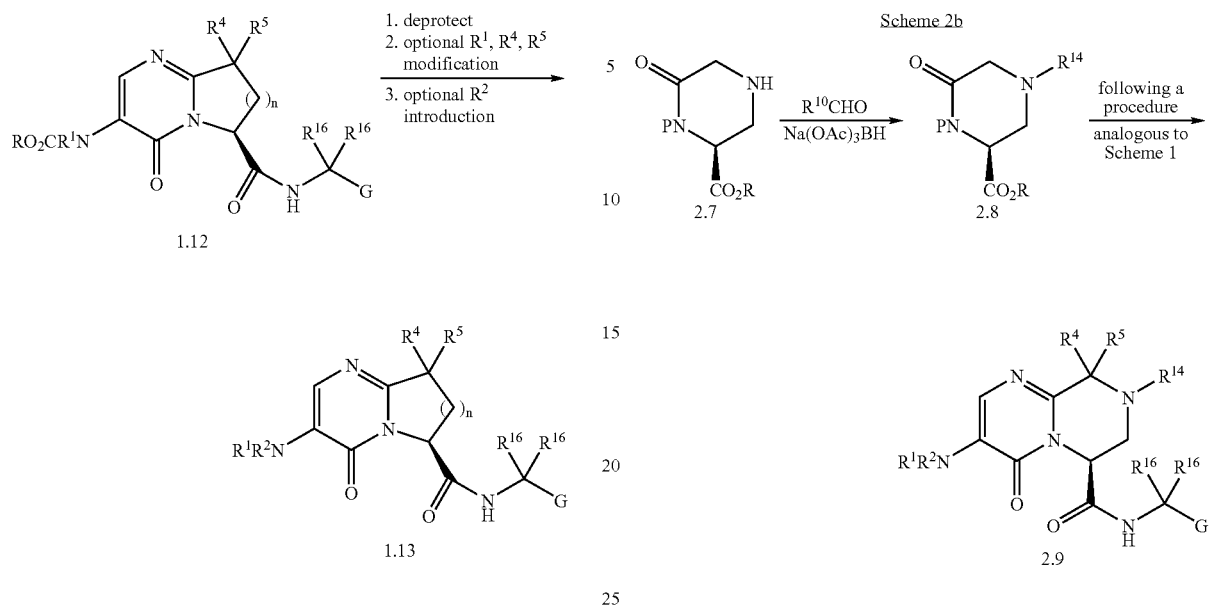
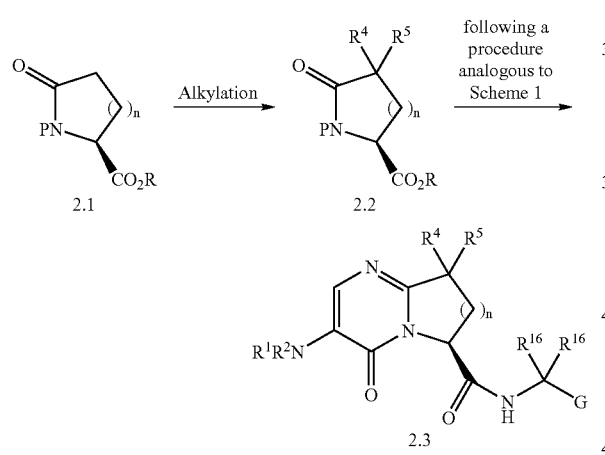
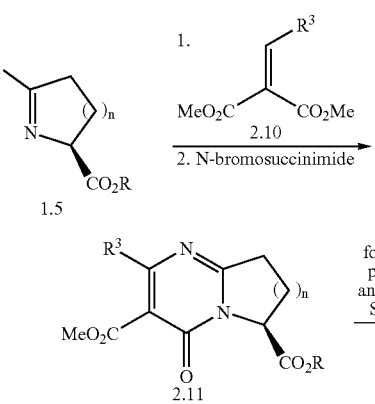
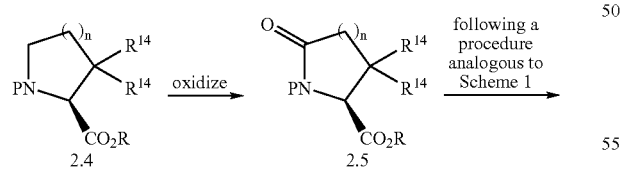
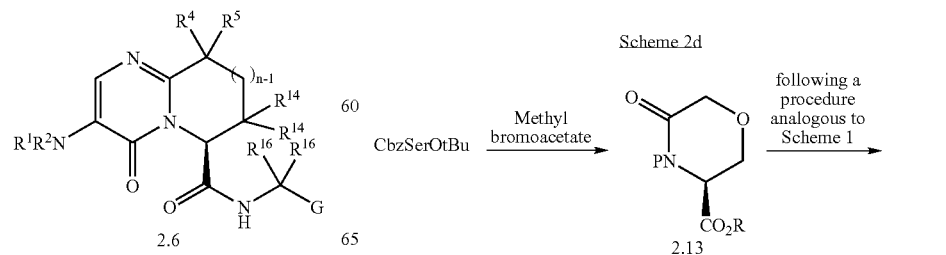

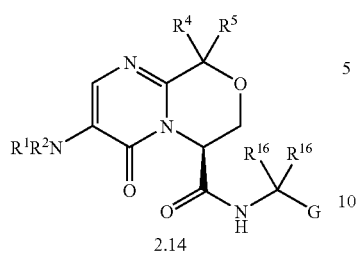

2.14

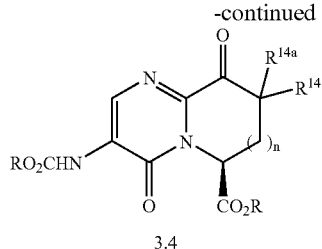

3.4

Scheme 3

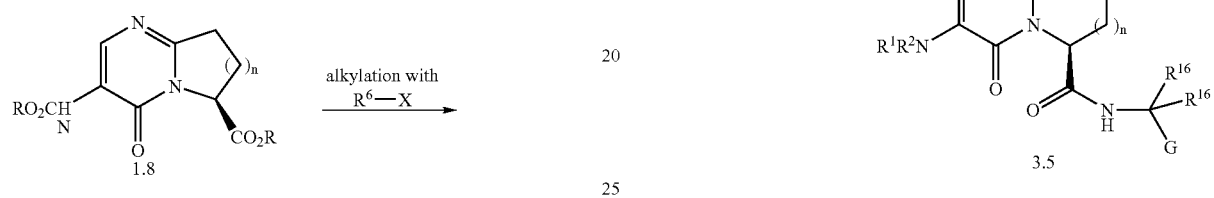

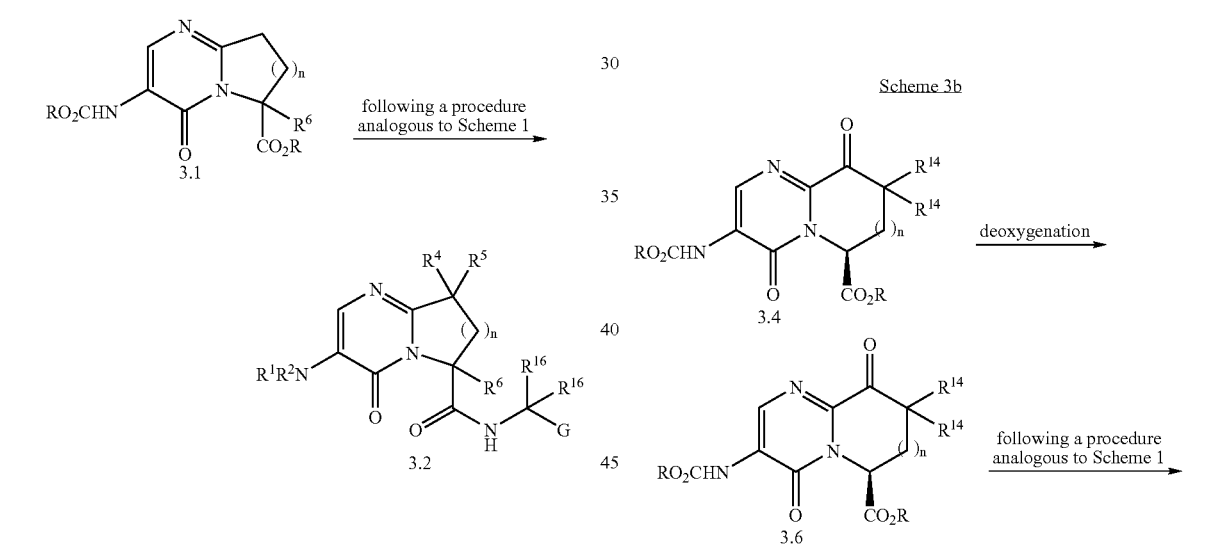

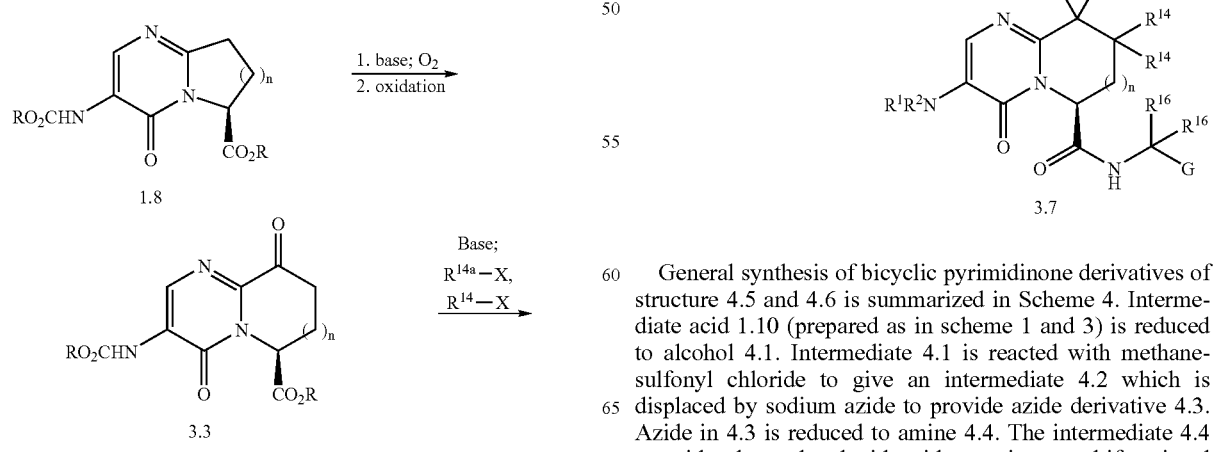

General synthesis of bicyclic pyrimidinone derivatives of structure 4.5 and 4.6 is summarized in Scheme 4. Intermediate acid 1.10 (prepared as in scheme 1 and 3) is reduced to alcohol 4.1. Intermediate 4.1 is reacted with methanesulfonyl chloride to give an intermediate 4.2 which is displaced by sodium azide to provide azide derivative 4.3. Azide in 4.3 is reduced to amine 4.4. The intermediate 4.4 can either be acylated with acids carrying a multifunctional group G, or reductively aminated with aldehydes carrying a multifunctional group G, to provide 4.5. Alternatively, 4.4 is reacted with sulfonyl chlorides carrying a multifunctional group G to give 4.6. This general synthesis can also be applied to prepare bicyclic pyrimidinones of the types described in Schemes 2 and 3.

directly synthesized using a chiral catalyst or a chiral ligand (e.g., Jacobsen, E. *Acc. Cheli. Res.* 2000, 33, 421–431).

Other features of the invention will become apparent in the course of the following descriptions of exemplary embodiments which are given for illustration of the invention and are not intended to be limiting thereof.

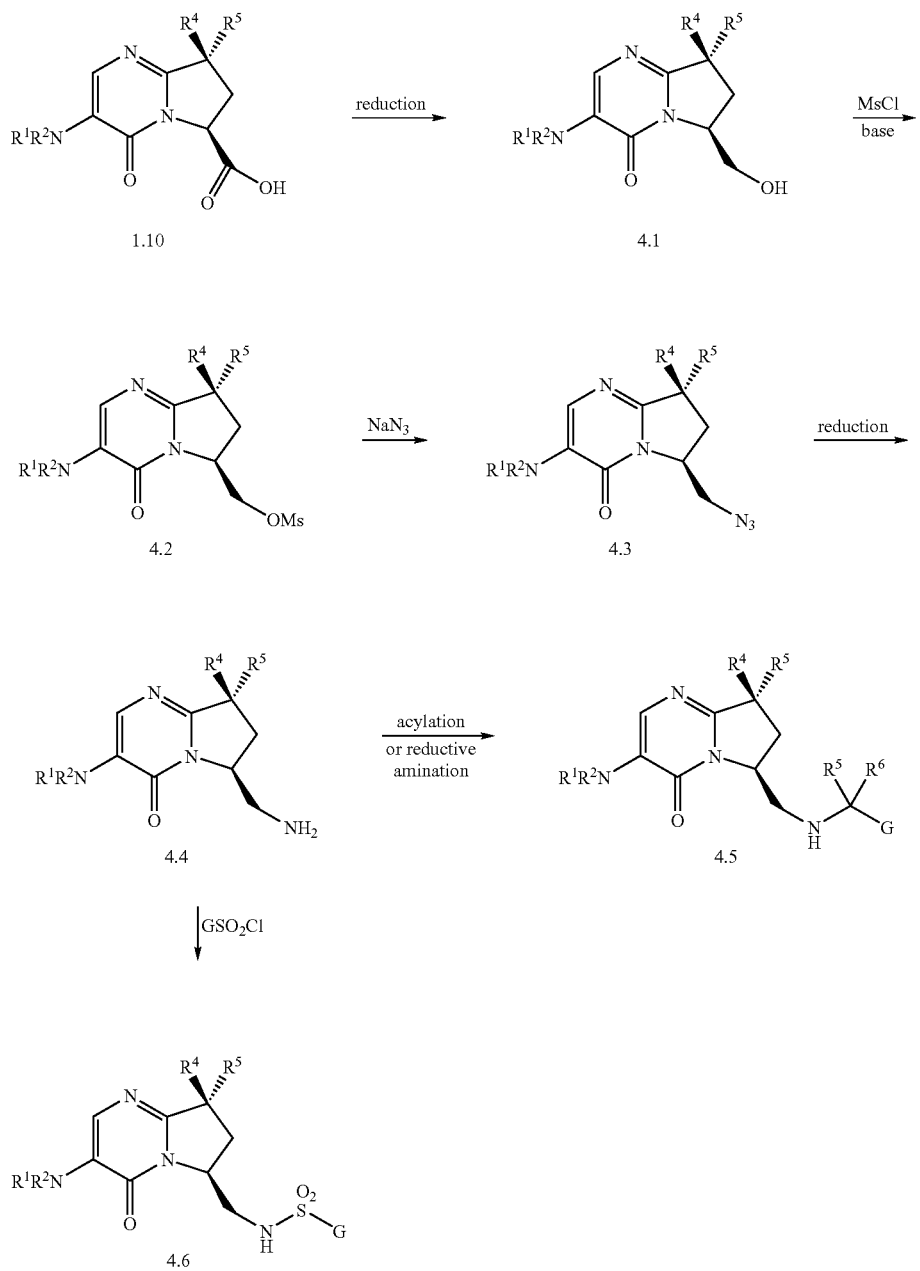

When required, separation of the racemic material can be achieved by HPLC using a chiral column and methods generally known to one skilled in the art or by a resolution using a resolving agent, for example camphonic chloride (Wilen, S. H. *Tables of Resolving Agents and Optical Resolutions* 1972, 308 pp). A chiral compound may also be

EXAMPLES

Solution ratio express a volume relationship, unless stated otherwise. NMR chemical shifts (δ) are reported in parts per million. Flash chromatography was carried out on silica gel according to Still's method (Still, W. C. et al. *J. Org. Chem.*

1978, 43, 2923). Abbreviations used in the Examples are defined as follows: "° C." for degrees Celsius, "MS" for mass spectrometry, "ESI" for electrospray ionization mass spectroscopy, "HR" for high resolution, "LC-MS" for liquid chromatography mass spectrometry, "eq" for equivalent or equivalents, "g" for gram or grams, "h" for hour or hours, "mg" for milligram or milligrams, "mL" for milliliter or milliliters, "mmol" for millimolar, "M" for molar, "min" for minute or minutes, "HPLC" for high pressure liquid chromatography, "rt" for room temperature, "NMR" for nuclear magnetic resonance spectroscopy, "tlc" for thin layer chromatography, "atm" for atmosphere, and "α", "β", "R", "S", "E", and "Z" are stereochemical designations familiar to one skilled in the art.

As used throughout the specification, the following abbreviations for chemical reagents apply:

Boc is tert-butyl oxycarbonyl,

BOP is benzotriazol-1-yloxy-tris(dimethylamino)phosphonium hexafluorophosphate,

Cbz is carbonylbenzyloxy,

CbzSerOtBu is (S)-2-tert-butoxycarbonylamino-3-hydroxy-propionic acid tert-butyl ester, Davis oxaziridine is 2-benzenesulfonyl-3-phenyl-oxaziridine, DCE is 1,2-dichloroethane, DIEA is diethylpropyl amine, DMAP is dimethylaminopyridine, DMSO is dimethyl sulfoxide, DMF is dimethylformamide, DPPA is diphenylphosphoryl azide, EDCI is 1-(3-dimethylaminopropyl)-3-ethylcarbodiimide hydrochloride, Et is ethyl, EtOAc is ethyl acetate, HATU is O-(7-azabenzotriazol-1-yl)-N,N,N',N'-tetramethyluronium, HOAc or AcOH is acetic acid, HOAT is 1-hydroxy-7-azabenzotriazole, LDA is lithium diisopropylamide, LiHMDS is bis(trimethylsilyl)amide, Me is methyl, MoOPH is oxodiperoxymolybdenum(pyridine)(hexamethylphosphoric triamide), MsCl is methanesulfonyl chloride, NaOAc is sodium actetate, OAc is acetate, Pr is propyl, TBAI is tetrabutylammonium iodide, TEA is triethylamine, TFA is trifluoroacetic acid, and THF is tetrahydrofuran.

The following Examples have been prepared, isolated and characterized using the methods disclosed herein. The following Examples demonstrate a partial scope of the invention and are not meant to be limiting of the scope of the invention.

Example 1

(S)-3-Benzylamino-4-oxo-4,6,7,8-tetrahydro-pyrrolo[1,2-a]pyrimidine-6-carboxylic acid 4-carbamimidoyl-benzylamide -continued

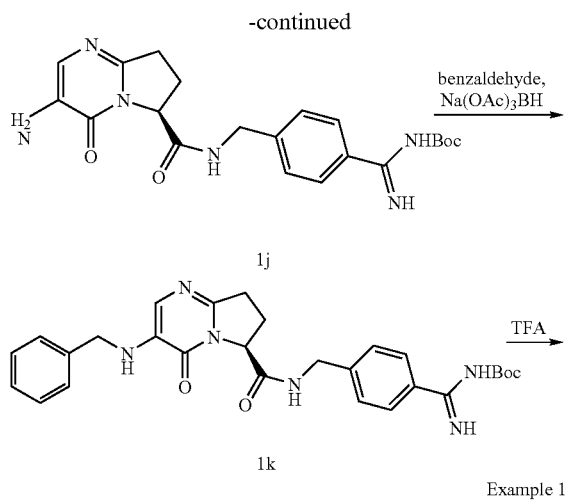

Example 1

Step A: tert-butyl (S)-5-oxo-2-pyrrolidinecarboxylate (1a).

To a suspension of L-pyroglutamic acid (13.2 g, 102 mmol) in t-butyl acetate (200 mL), was added perchloric acid (70%, 9.7 mL, 113 mmol). The mixture was stirred at rt for 20 h, then poured into sat. NaHCO$_3$. NaHCO$_3$ (s) was added until neutral. The aqueous phase was extracted with EtOAc (6×). The combined organic extract was dried (Na$_2$SO$_4$) and concentrated to afford 13.68 g (72%) of the title compound, 1a. $^1$H NMR (300 MHz, CDCl$_3$) δ 6.17 (br s, 1H), 4.13 (dd, J=7.4, 5.2, 1H), 2.44–2.31 (m, 3H), 2.22–2.15 (m, 1H), 1.47 (s, 9H).

Step B: tert-butyl (S)-5-thioxo-2-pyrrolidinecarboxylate (1b).

To a solution of t-butyl pyroglutamate (1a) (10.12 g, 54.6 mmol) in benzene (250 mL), was added Lawesson's reagent (11.05 g, 27.3 mmol). The mixture was refluxed for 15.5 h, then concentrated. The resultant residue was purified by flash chromatography (0 to 2 to 3 to 4% MeOH/CHCl$_3$) to afford 10.50 g (95%) of the title compound, 1b. $^1$H NMR (300 MHz, CDCl$_3$) δ 7.27 (br s, 1H), 4.46–4.39 (m, 1H), 3.03–2.84 (m, 2H), 2.58–2.46 (m, 1H), 2.37–2.23 (m, 2H), 1.49 (s, 9H).

Step C: tert-butyl (S)-5-(methylsulfanyl)-3,4-dihydro-2H-pyrrole-2-carboxylate (1c).

To a solution of thiolactam 1b (10.50 g, 52.2 mmol) in 200 mL THF at rt, was added MeI (13.0 mL, 208.7 mmol). The mixture was stirred for 3.5 h, then concentrated. The residue was partitioned between CH$_2$Cl$_2$ and sat. NaHCO$_3$ and the aqueous phase was extracted with CH$_2$Cl$_2$ (3×). The combined organic extract was dried (Na$_2$SO$_4$) and concentrated to afford 10.17 g (91%) of the title compound, 1c, as a brown oil. $^1$H NMR (300 MHz, CDCl$_3$) δ 4.60 (dd, J=6.2, 7.3, 1H), 2.83–2.58 (m, 2H), 2.49 (s, 3H), 2.37–2.22 (m, 1H), 2.17–2.03 (m, 1H), 1.48 (s, 9H).

Step D: tert-butyl (S)-5-amino-3,4-dihydro-2H-pyrrole-2-carboxylate (1d).

To a solution of 1c (10.17 g, 47.2 mmol) in 100 mL MeOH, was added NH$_4$Cl (2.65 g, 49.6 mmol). The mixture was refluxed for 2 h, then concentrated. The residue was taken up in 200 mL CHCl$_3$ and stirred for 20 min until only a fine suspension persisted. The mixture was filtered and the filtrate concentrated. The solid was suspended in hexanes, sonicated, and then filtered and dried to afford 8.30 g (80%) of the amidine hydrochlordie salt as an off-white solid. $^1$H NMR (300 MHz, CDCl$_3$) δ 4.44 (dd, J=8.8, 5.1, 1H), 3.11–3.05 (m, 2H), 2.58–2.45 (m, 1H), 2.28–2.15 (m, 1H), 1.48 (s, 9H). The amidine hydrochloride (11.0 g, 49.8 mmol) was partitioned between CHCl$_3$ and sat. K$_2$CO$_3$. The layers were separated and the aqueous layer was extracted with CHCl$_3$ (2×). The combined organic phase was dried (Na$_2$SO$_4$) and concentrated to afford 8.50 g (93%) of free base 1d. $^1$H NMR (300 MHz, CDCl$_3$) δ 4.44 (br s, 2H), 4.38 (dd, J=8.0, 5.5, 1H), 2.65–2.42 (m, 2H), 2.32–2.18 (m, 11H), 2.12–2.00 (m, 1H), 1.47 (s, 9H).

Step E: 6-tert-butyl 3-methyl (S)-4-oxo-4,6,7,8-tetrahydropyrrolo[1,2-a]pyrimidine-3,6-dicarboxylate (1e).

To a solution of dimethyl methoxymethylene malonate (8.68 g, 49.8 mmol) in 100 mL MeOH at −10° C., was added a solution of Ed (8.50 g, 46.1 mmol) in 100 mL MeOH over 1 h. The mixture was stirred at rt for 2 h, then was allowed to warm to rt overnight. The mixture was concentrated in vacuo and the resultant residue was purified by flash chromatography (50 to 100% EtOAc/hexanes) to afford 6.32 g (46%) of pyrimidinone 1e, as a colorless solid. $^1$H NMR (300 MHz, CDCl$_3$) δ 8.69 (s, 1H), 5.03 (dd, J=9.7, 2.8, 1H), 3.90 (s, 3H), 3.38–3.09 (m, 2H), 2.64–2.49 (m, 1H), 2.34–2.23 (m, 1H), 1.49 (s, 9H).

Step F: (S)-6-(tert-butoxycarbonyl)-4-oxo-4,6,7,8-tetrahydropyrrolo[1,2-a]pyrimidine-3-carboxylic acid (1f).

To a solution of 1e (14.15 g, 48.1 mmol) in 250 mL MeOH at 0° C. was slowly added aqueous LiOH (1M, 48 mL, 48 mmol) over 15 min. The reaction was allowed to warm to rt overnight with stirring. The organic solvent was removed in vacuo. The residual aqueous solution was partitioned with Et$_2$O, then the organic phase was extracted with H$_2$O (2×). The combined aqueous extract was acidified to pH 2 with 1N HCl. The aqueous phase was extracted with CHCl$_3$ (3×). The combined organic extract was dried (MgSO$_4$) and concentrated to afford 11.4 g (85%) of the acid, if, as a tan crystalline solid.

Step G: tert-butyl (S)-3-{[(benzyloxy)carbonyl]amino}-4-oxo-4,6,7,8-tetrahydropyrrolo[1,2-a]pyrimidine-6-carboxylate (1g).

A solution of carboxylic acid 1f (11.4 g, 40.7 mmol), triethylamine (5.67 mL, 40.7 mmol), and DPPA (8.86 mL, 40.7 mmol) in 180 mL 1,4-dioxane was heated at reflux for 2 h. Benzyl alcohol (4.67 mL, 45 mmol) was added and the mixture was heated at reflux for an additional 3 h. The mixture was concentrated in vacuo and the oil obtained was purified by flash chromatography (50 to 100% EtOAc/hexanes) to provide 11.13 g (73%) of the benzyl carbamate (1 g) as a tan solid. $^1$H NMR (300 MHz, CDCl$_3$) δ 8.67 (br s, 1H), 7.39–7.34 (m, 5H), 5.21 (s, 2H), 4.98 (dd, J=9.6, 3.0, 1H), 3.23–2.98 (m, 2H), 2.63–2.49 (m, 1H), 2.37–2.23 (m, 1H), 1.48 (s, 9H).

Step H: (S)-3-{[(benzyloxy)carbonyl]amino}-4-oxo-4,6,7,8-tetrahydropyrrolo[1,2-a]pyrimidine-6-carboxylic acid (1 h).

tert-Butyl ester 1 g (11.13 g, 28.9 mmol) was dissolved in 1:1 CH$_2$Cl$_2$/TFA. 1 mL H$_2$O was added and the mixture was stirred overnight at rt. The mixture was concentrated and the resultant residue was co-evaporated with CCl$_4$ (3×). The residual oil was triturated with 1:1 Et$_2$O/hexanes (100 mL) and the solid (9.0 g, 95%) was collected and dried, to provide 1 h. $^1$H NMR (300 MHz, CDCl$_3$) δ 8.69 (br s, 1H), MS (ESI) 330.3 (M+H$^+$); 328.3 (M−H+).

Step I: (S) {6-[4-(tert-butoxycarbonylamino-imino-methyl)-benzylcarbamoyl]-4-oxo-4,6,7,8-tetrahydro-pyrrolo[1,2-a]pyrimidin-3-yl}-carbamic acid benzyl ester (1i).

To a solution of intermediate 1h (150 mg, 0.60 mmol) and [(4-aminomethyl-phenyl)-imino-methyl]-carbamic acid tert-butyl ester (181.1 mg, 0.55 mmol) in 3 mL $CH_3CN$ was added DIEA (156.4 mg, 1.21 mmol), and HATU (250.9 mg, 0.66 mmol). The solution was stirred at rt for two nights. The mixture was diluted with EtOAc, then washed with 1N HCl, $H_2O$, saturated $NaHCO_3$ and brine. It was dried ($Na_2SO_4$), concentrated and purified by $SiO_2$ chromatography (2–8% $MeOH/CH_2Cl_2$) to afford 119.1 mg (38.6%) of intermediate 1i. MS (ESI) 561.2 (M+H$^+$).

Step J: (S)-[(4-{[(3-amino-4-oxo-4,6,7,8-tetrahydro-pyrrolo[1,2-a]pyrimidine-6-carbonyl)-amino]-methyl}-phenyl)-imino-methyl]-carbamic acid tert-butyl ester (1j).

To a solution of intermediate 1i (74.8 mg, 0.134 mmol) in 3 mL MeOH, was added 80 mg 10% Pd/C. The mixture was evacuated and flushed with $H_2$ (3×), then it was stirred under an atmosphere of $H_2$ for 24 h. The mixture was filtered and concentrated to afford 48 mg (84%) of intermediate 1j. MS (ESI) 427.08 (M+H$^+$).

Step K: (6S)-[(4-{[(3-benzylamino-4-oxo-4,6,7,8-tetrahydro-pyrrolo[1,2-a]pyrimidine-6-carbonyl)-amino]-methyl}-phenyl)-imino-methyl]-carbamic acid tert-butyl ester (1k).

To a solution of intermediate 1j (60 mg, 0.14 mmol) and benzaldehyde (29.7 mg, 0.28 mmol) in 2 mL dichloroethane was added acetic acid (83.1 mg, 0.84 mmol), and NaBH(OAc)$_3$ (267.0 mg, 1.26 mmol). The solution was stirred at rt for 2 h. The mixture was diluted with saturated $NaHCO_3$ solution and extracted with EtOAc (3×). The combined organics were washed with brine, dried ($Na_2SO_4$) and concentrated to afford 71.2 mg (98%) of benzyl amine intermediate 1k. MS (ESI) 517.0 (M+H$^+$).

Step L:

Example 1

To intermediate 1k was added 1 mL TFA+1% $H_2O$+1.5% triisopropyl silane. The mixture was stirred at rt for 2 h. The reaction mixture was evaporated and purified by semi-prep HPLC (gradient elution: 0–50% $CH_3CN/H_2O$+0.1% TFA) to afford 11.1 mg (19%) of benzyl amine Example 1. MS (HR-ESI) calc'd for $C_{23}H_{25}N_6O_2$ (M+H$^+$), found 417.2053; $^1$H NMR (300 MHz, $CD_3OD$) δ 9.19–9.13 (m, 1H), 7.65 (d, J=8.4, 2H), 7.56 (d, J=8.8, 2H), 7.34–7.18 (m, 5H), 6.86 (s, 1H), 5.17 (dd, J=3.3, 9.5, 1H), 4.67–4.35 (m, 2H), 4.33 (s, 2H), 3.31–3.04 (m, 2H), 2.71–2.55 (m, 1H), 2.35–2.23 (m, 1H).

Example 2

(S)-4-Oxo-3-phenethylamino-4,6,7,8-tetrahydro-pyrrolo[1,2-a]pyrimidine-6-carboxylic acid 4-carbamimidoyl-benzylamide Step A: (S)-[imino-(4-{[(4-oxo-3-phenethylamino-4,6,7,8-tetrahydro-pyrrolo[1,2-a]pyrimidine-6-carbonyl)-amino]-methyl}-phenyl)-methyl]-carbamic acid tert-butyl ester (2a).

Following a procedure similar to that for the preparation of 1k, intermediate 1j (60 mg, 0.14 mmol), phenylacetyladehyde (67.3 mg, 0.56 mmol) and NaBH(OAc)$_3$ (326.4 mg, 1.54 mmol) yielded 40 mg (54%) of intermediate 2a. MS (ESI) 531.1 (M+H$^+$).

Step B:

Example 2

According to the procedure for the preparation of Example 1, intermediate 2a (40 mg, 0.08 mmol) was deprotected and purified to afford 5.2 mg (15%) of Example 2. MS (HR-ESI) calc'd for $C_{24}H_{27}N_6O_2$ (M+H$^+$), found 431.2203; $^1$H NMR (300 MHz, $CD_3OD$) δ 9.20–9.18 (m, 1H), 7.74 (d, J=8.4, 2H), 7.54 (d, J=8.4, 2H), 7.25–7.20 (m, 5H), 7.02 (s, 1H), 5.17 (dd, J=3.4, 9.3, 11H), 4.61 (d, J=16.1, 1H), 4.40 (d, J=16.1, 1H), 3.39–3.10 (m, 4H), 2.90 (t, J=7.2, 2H), 2.74–2.59 (m, 1H), 2.35–2.15 (m, 1H).

Example 3

(S)-3-Diethylamino-4-oxo-4,6,7,8-tetrahydro-pyrrolo[1,2-a]pyrimidine-6-carboxylic acid 4-carbamimidoyl-benzylamide Step A: (S)-[(4-{[(3-diethylamino-4-oxo-4,6,7,8-tetrahydro-pyrrolo[1,2-a]pyrimidine-6-carbonyl)-amino]-methyl}-phenyl)-imino-methyl]-carbamic acid tert-butyl ester (3a).

Following a procedure similar to that for the preparation of 1k, intermediate 1j (48 mg, 0.113 mmol), acetaldehyde (39.6 mg, 0.90 mmol) and NaBH(OAc)$_3$ (216.2 mg, 1.02 mmol) yielded 56 mg (100%) of intermediate 3a. MS (ESI) 483.1 (M+H$^+$).

Step B:

Example 3

According to the procedure for the preparation of Example 1, intermediate 3a (56 mg, 0.113 mmol) was deprotected and purified to afford 3.3 mg (7.6%) of Example 3. MS (HR-ESI) calc'd for $C_{20}H_{27}N_6O_2$ (M+H$^+$), found 383.2211; $^1$H NMR (300 MHz, $CD_3OD$) δ 9.20–9.10 (m, 1H), 7.75 (d, J=8.7, 2H), 7.54 (d, J=8.4, 2H), 7.39 (s, 1H), 5.19–5.11 (m, 1H), 4.63–4.40 (m, 2H), 3.58–3.47 (m, 4H), 3.27–3.18 (m, 2H), 2.72–2.58 (m, 1H), 2.35–2.20 (m, 1H), 1.17–1.07 (t, J=7.2, 6H).

Example 4

(S)-3-Isopropylamino-4-oxo-4,6,7,8-tetrahydro-pyrrolo[1,2-a]pyrimidine-6-carboxylic acid 4-carbamimidoyl-benzylamide Step A: (S)-[(4-{[(3-isopropylamino-4-oxo-4,6,7,8-tetrahydro-pyrrolo[1,2-a]pyrimidine-6-carbonyl)-amino]-methyl}-phenyl)-imino-methyl]-carbamic acid tert-butyl ester (4a).

Following a procedure similar to that for the preparation of intermediate 1k, intermediate 1j (60 mg, 0.14 mmol), acetone (97.6 mg, 1.68 mmol) and NaBH(OAc)$_3$ (385.7 mg, 1.82 mmol) yielded 43 mg (65%) of intermediate 4a. MS (ESI) 469.1 (M+H$^+$).

Step B:

Example 4

According to the procedure for the preparation of Example 1, 4a (43 mg, 0.092 mmol) was deprotected and purified to afford 3.8 mg (11%) of Example 4. MS (ESI)

369.4 (M+H⁺); ¹H NMR (300 MHz, CD₃OD) δ 8.50–5.42 (m, 11H), 7.61 (d, J=8.4. 2H), 7.38 (d, J=8.5, 2H), 6.90 (s, 11H), 5.03–4.97 (m, 1H), 4.56–4.35 (m, 2H), 3.48–3.30 (m, 1H), 3.24–3.13 (m, 1H), 3.00–2.87 (m, 1H), 2.89–2.31 (m, 11H), 1.97–1.91 (m, 1H), 1.16 (d, J=6.2, 6H).

Example 5

(S)-3-Ethylamino-4-oxo-4,6,7,8-tetrahydro-pyrrolo[1,2-a]pyrimidine-6-carboxylic acid 4-carbamimidoyl-benzylamide Step A: (S)-[(4-{[(3-ethylamino-4-oxo-4,6,7,8-tetrahydro-pyrrolo[1,2-a]pyrimidine-6-carbonyl)-amino]-methyl}-phenyl)-imino-methyl]-carbamic acid tert-butyl ester (5a).

Following a procedure similar to that for the preparation of intermediate 1k, intermediate 1j (101 mg, 0.24 mmol), acetaldehyde (21.1 mg, 0.48 mmol) and NaBH(OAc)₃ (141.99 mg, 0.67 mmol) yielded 66 mg (60.5%) of intermediate 5a. MS (ESI) 455.1 (M+H⁺).

Step B:

Example 5

According to the procedure for the preparation of Example 1, 5a (66 mg, 0.15 mmol) was deprotected and purified to afford 10.6 mg (20%) of Example 5. MS (HR-ESI) calc'd for C₁₈H₂₃N₆O₂ (M+H⁺), found 355.1887; ¹H NMR (300 MHz, CD₃OD) δ 9.25–9.15 (m, 1H), 7.74 (d, J=8.4, 2H), 7.56 (d, J=8.4, 2H), 7.03 (s, 1H), 5.24–5.16 (m, 11H), 4.68–4.34 (m, 2H), 3.30 (q, J=7.2, 2H), 2.75–2.60 (m, 11H), 1.24 (t, J=7.1, 3H).

Example 6

(S)-3-Cyclopentylamino-4-oxo-4,6,7,8-tetrahydro-pyrrolo[1,2-a]pyrimidine-6-carboxylic acid 4-carbamimidoyl-benzylamide Step A: (S)-[(4-{[(3-cyclopentylamino-4-oxo-4,6,7,8-tetrahydro-pyrrolo[1,2-a]pyrimidine-6-carbonyl)-amino]-methyl}-phenyl)-imino-methyl]-carbamic acid tert-butyl ester (6a)

Following a procedure similar to that for the preparation of intermediate 1k, intermediate 1j (115.2 mg, 0.27 mmol), cyclopentanone (68.1 mg, 0.81 mmol) and NaBH(OAc)₃ (217.5 mg, 1.03 mmol) yielded 76.5 mg (57.3%) of intermediate 6a. MS (ESI) 496.1 (M+H⁺).

Step B:

Example 6

According to the procedure for the preparation of Example 1, 6a (76.5 mg, 0.15 mmol) was deprotected and half was purified to afford 15.3 mg (52% for fraction purified) of Example 6. MS (HR-ESI) calc'd for C₂₁H₂₇N₆O₂ (M+H⁺), found 395.2200; ¹H NMR (300 MHz, CD₃OD) δ 9.15–9.09 (m, 1H), 7.74 (d, J=8.4, 2H), 7.54 (d, J=8.0, 2H), 7.03 (s, 1H), 5.12 (dd, J=3.3, 9.2, 1H), 4.68–4.57 (m, 1H), 4.40 (dd, J=3.7, 16.1, 1H), 3.72–3.63 (m, 1H), 3.28–3.02 (m, 2H), 2.70–5.54 (m, 1H), 2.32–2.20 (m, 1H), 2.09–1.94 (m, 2H), 1.76–1.47 (m, 6H).

Example 7

(S)-3-Isobutylamino-4-oxo-4,6,7,8-tetrahydro-pyrrolo[1,2-a]pyrimidine-6-carboxylic acid 4-carbamimidoyl-benzylamide Step A: (S)-[(4-{[(3-isobutylamino-4-oxo-4,6,7,8-tetrahydro-pyrrolo[1,2-a]pyrimidine-6-carbonyl)-amino]-methyl}-phenyl)-imino-methyl]-carbamic acid tert-butyl ester (7a)

Following a procedure similar to that for the preparation of intermediate 1k, intermediate 1j (97.1 mg, 0.228 mmol), isobutyraldehyde (32.8 mg, 0.455 mmol) and NaBH(OAc)₃ (135.1 mg, 0.638 mmol) yielded 87.4 mg (79%) of intermediate 7a. MS (ESI) 483.1 (M+H⁺).

Step B:

Example 7

According to the procedure for the preparation of Example 1, intermediate 7a (87.4 mg, 0.18 mmol) was deprotected and half was purified to afford 15.2 mg (44% for fraction purified) of isobutyl amine Example 7. MS (HR-ESI) calc'd for C₂₀H₂₇N₆O₂ (M+H⁺), found 383.2208; ¹H NMR (300 MHz, CD₃OD) δ 9.20–9.15 (m, 1H), 7.75 (dd, J=1.8, 8.4, 2H), 7.57 (d, J=8.4, 2H), 7.03 (s, 1H), 5.19–5.14 (m, 1H), 4.76–4.38 (m, 2H), 2.91 (d, J=6.9, 1H), 2.70–2.59 (m, 1H), 2.37–2.24 (m, 1H), 1.98–1.87 (m, 1H), 0.97 (d, J=6.6, 6H).

Example 8

(S)-3-Propylamino-4-oxo-4,6,7,8-tetrahydro-pyrrolo[1,2-a]pyrimidine-6-carboxylic acid 4-carbamimidoyl-benzylamide Step A: (S)-[(4-{[(3-propylamino-4-oxo-4,6,7,8-tetrahydro-pyrrolo[1,2-a]pyrimidine-6-carbonyl)-amino]-methyl}-phenyl)-imino-methyl]-carbamic acid tert-butyl ester (8a).

Following a procedure similar to that for the preparation of intermediate 1k, intermediate 1j (100 mg, 0.234 mmol), propionaldehyde (15 mg, 0.258 mmol) and NaBH(OAc)₃ (74.5 mg, 0.352 mmol) yielded 50.9 mg (46%) of intermediate 8a. MS (ESI) 469.1 (M+H⁺).

Step B:

Example 8

According to the procedure for the preparation of Example 1, intermediate 8a (50.9 mg, 0.11 mmol) was deprotected and half was purified to afford 13.4 mg (15% for fraction purified) of Example 8. MS (HR-ESI) calc'd for C₁₉H₂₅N₆O₂ (M+H⁺), found 369.2036; ¹H NMR (300 MHz, CD₃OD) δ 9.17–9.07 (m, 1H), 7.74 (d, J=8.4, 2H), 7.55 (d, J=8.4, 2H), 7.00 (s, 1H), 4.65–4.56 (m, 1H), 4.45–4.35 (m, 1H), 3.20–2.96 (m, 3H), 2.65–2.54 (m, 1H), 2.30–2.19 (m, 1H), 1.70–1.55 (m, 2H), 0.96 (t, J=7.5, 3H).

Example 9

(S)-3-Diisobutylamino-4-oxo-4,6,7,8-tetrahydro-pyrrolo[1,2-a]pyrimidine-6-carboxylic acid 4-carbamimidoyl-benzylamide Step A: (S)-[(4-{[(3-diisobutylamino-4-oxo-4,6,7,8-tetrahydro-pyrrolo[1,2-a]pyrimidine-6-carbonyl)-amino]-methyl}-phenyl)-imino-methyl]-carbamic acid tert-butyl ester (9a).

Following a procedure similar to that for the preparation of intermediate 1j (97.1 mg, 0.228 mmol), isobutyraldehyde (32.8 mg, 0.455 mmol) and NaBH(OAc)$_3$ (135.1 mg, 0.638 mmol) yielded 87.4 mg (79.5%) of intermediate 9a. MS (ESI) 539.2 (M+H$^+$).

Step B:

Example 9

According to the procedure for the preparation of Example 1, intermediate 9a (87.4 mg, 0.18 mmol) was deprotected and half was purified to afford 8.2 mg (23.8% for fraction purified) of Example 9. MS (HR-ESI) calc'd for C$_{24}$H$_{35}$N$_6$O$_2$ (M+H$^+$), found 439.2833; $^1$H NMR (300 MHz, CD$_3$OD) δ 7.74 (d, J=8.4, 2H), 7.57 (d, J=8.4, 2H), 7.31 (s, 11H), 5.16–5.09 (m, 1H), 4.52 (dd, J=16.1, 63.7, 2H), 3.32–3.03 (m, 6H), 2.70–2.56 (m, 1H), 2.30–2.19 (m, 1H), 1.88–1.75 (m, 2H), 0.83 (dd, J=2.2, 6.6, 12H).

Example 10

(S)-3-sec-Butylamino-4-oxo-4,6,7,8-tetrahydro-pyrrolo[1,2-a]pyrimidine-6-carboxylic acid 4-carbamimidoyl-benzylamide Step A: (S)-[(4-{[(3-sec-butylamino-4-oxo-4,6,7,8-tetrahydro-pyrrolo[1,2-a]pyrimidine-6-carbonyl)-amino]-methyl}-phenyl)-imino-methyl]-carbamic acid tert-butyl ester (10a).

Following a procedure similar to that for the preparation of intermediate 1k, intermediate 1j (100 mg, 0.234 mmol), 2-butanone (33.8 mg, 0.469 mmol) and NaBH(OAc)$_3$ (139.1 mg, 0.657 mmol) yielded 38.4 mg (35%) of intermediate 10a. MS (ESI) 483.1 (M+H$^+$).

Step B:

Example 10

According to the procedure for the preparation of Example 1, intermediate 10a (38.4 mg, 0.08 mmol) was deprotected and half was purified to afford 12.3 mg (80.4% for fraction purified) of Example 10. MS (HR-ESI) calc'd for C$_{20}$H$_{27}$N$_6$O$_2$ (M+H$^+$), found 383.2201; $^1$H NMR (300 MHz, CD$_3$OD) δ 9.25–9.18 (m, 1H), 7.78 (d, J=8.4, 2H), 7.59 (d, J=8.4, 2H), 7.08 (s, 1H), 5.18 (dd, J=3.3, 9.1, 1H), 4.70–4.62 (m, 1H), 4.50–4.39 (m, 1H), 3.37–3.12 (m, 3H), 2.5–2.60 (m, 1H), 2.38–2.25 (m, 1H), 1.70–1.50 (m, 1H), 1.19 (d, J=6.2, 3H), 0.96 (t, J=7.3, 3H).

Example 11

(S)-3-(1-Ethyl-propylamino)-4-oxo-4,6,7,8-tetrahydro-pyrrolo[1,2-a]pyrimidine-6-carboxylic acid 4-carbamimidoyl-benzylamide Step A: (S)-{[4-({[3-(1-ethyl-propylamino)-4-oxo-4,6,7,8-tetrahydro-pyrrolo[1,2-a]pyrimidine-6-carbonyl]-amino}-methyl)-phenyl]-imino-methyl}-carbamic acid tert-butyl ester (11a).

Following a procedure similar to that for the preparation of intermediate 1k, intermediate 1j (100 mg, 0.234 mmol), 3-pentanone (33.8 mg, 0.469 mmol) and NaBH(OAc)$_3$ (139.1 mg, 0.657 mmol) yielded 27.8 mg (24%) of intermediate 11a. MS (ESI) 497.1 (M+H$^+$).

Step B:

Example 11

According to the procedure for the preparation of Example 1, intermediate 11a (27.8 mg, 0.06 mmol) was deprotected and half was purified to afford 10.8 mg (91% for fraction purified) of Example 11. MS (HR-ESI) calc'd for C$_{21}$H$_{29}$N$_6$O$_2$ (M+H$^+$), found 397.2367; $^1$H NMR (300 MHz, CD$_3$OD) δ 9.18–9.13 (m, 1H), 7.78 (d, J=8.4, 2H), 7.59 (d, J=8.4, 2H), 7.07 (s, 1H), 5.17 (dd, J=3.3, 9.2, 11H), 4.71–4.62 (m, 1H), 4.49–4.40 (m, 1H), 3.32–3.03 (m, 5H), 2.73–2.59 (m, 1H), 2.35–2.24 (m, 1H), 1.70–1.47 (m, 4H), 0.93 (t, J=7.4, 6H).

Example 12

(S)-4-[6-(4-Carbamimidoyl-benzylcarbamoyl)-4-oxo-4,6,7,8-tetrahydro-pyrrolo[1,2-a]pyrimidin-3-ylamino]-pentanoic acid benzyl ester Step A: (S)-4-{6-[4-(tert-butoxycarbonylamino-imino-methyl)-benzylcarbamoyl]-4-oxo-4,6,7,8-tetrahydro-pyrrolo[1,2-a]pyrimidin-3-ylamino}-pentanoic acid benzyl ester (12a).

Following a procedure similar to that for the preparation of intermediate 1k, intermediate 1j (100.0 mg, 0.234 mmol), benzyl levulinate (96.7 mg, 0.469 mmol) and NaBH(OAc)$_3$ (139.1 mg, 0.657 mmol) yielded 51 mg (35%) of benzyl ester amine intermediate 12a. MS (ESI) 617.1 (M+H$^+$).

Step B:

Example 12

According to the procedure for the preparation of Example 1, intermediate 12a (51 mg, 0.08 mmol) was deprotected and one quarter was purified to afford 4.8 mg (17.4% for fraction purified) of Example 12. MS (HR-ESI) calc'd for C$_{28}$H$_{33}$N$_6$O$_4$ (M+H$^+$), found 517.2584; $^1$H NMR (300 MHz, CD$_3$OD) δ 9.22–9.18 (m, 1H), 7.76 (d, J=8.5, 2H), 7.58 (d, J=8.5, 2H), 7.35–7.28 (m, 5H), 7.11 (s, 1H), 5.24–5.17 (m, 1H), 5.13–5.03 (m, 2H), 4.70–4.41 (m, 2H), 3.49–3.12 (m, 3H), 2.77–2.63 (m, 1H), 2.47 (t, J=7.2, 2H), 1.20 (d, J=7.0, 3H).

Example 13

(S)-4-[6-(4-Carbamimidoyl-benzylcarbamoyl)-4-oxo-4,6,7,8-tetrahydro-pyrrolo[1,2-a]pyrimidin-3-ylamino]-pentanoic acid To a solution of Example 12 (2.8 mg, 0.0054 mmol) in 1.5 mL MeOH/H$_2$O (2:1), was added 10 mg 10% Pd-C. The mixture was evacuated and flushed with H$_2$ (3×), then it was stirred under an atmosphere of H$_2$ for 24 h. The mixture was filtered and concentrated to afford 1.8 mg (78%) of Example 13. MS (ESI) 427.3 (M+H$^+$). $^1$H NMR (300 MHz, CD$_3$OD) δ 7.57 (d, J=8.5, 2H), 7.33 (d, J=8.1, 2H), 7.09 (s, 1H), 5.02–4.97 (m, 1H), 4.60–4.34 (m, 1H), 3.35–3.22 (m, 1H), 3.08–2.90 (m, 2H), 2.60–2.45 (m, 1H), 2.35–2.11 (m, 3H), 1.75–1.61 (m, 2H), 1.02–0.99 (m, 3H).

Example 14

(S)-[6-(4-Carbamimidoyl-benzylcarbamoyl)-4-oxo-4,6,7,8-tetrahydro-pyrrolo[1,2-a]pyrimidin-3-yl]-carbamic acid benzyl ester To intermediate 1i (38.1 mg, 0.068 mmol) was added 1 mL TFA. The mixture was stirred at RT for 1 h then rotovaped to give 20.2 mg (52%) of Example 14. MS (HR-ESI) calc'd for $C_{24}H_{25}N_6O_4$ (M+H$^+$), found 461.1938; $^1$H NMR (300 MHz, CD$_3$OD) δ 8.92–8.83 (m, 1H), 8.68–8.56 (m, 11H), 7.73 (d, J=8.4, 2H), 7.51 (d, J=8.4, 2H), 7.47 (s, 1H), 7.42–7.35 (m, 5H), 5.22 (s, 2H), 5.12 (dd, J=3.3, 9.1, 1H), 4.68–4.57 (m, 1H), 4.47–4.38 (m, 1H), 3.40–3.25 (m, 11H), 3.14–3.00 (m, 1H), 2.67–2.52 (m, 1H), 2.40–2.29 (m, 1H).

Example 15

(S)-3-Amino-4-oxo-4,6,7,8-tetrahydro-pyrrolo[1,2-a]pyrimidine-6-carboxylic acid 4-carbamimidoyl-benzylamide According to the procedure for Example 1, intermediate 1j (30 mg, 0.07 mmol) was deprotected to afford 3.5 mg (15.2%) of Example 15. MS (ESI) 327.3 (M+H$^+$); $^1$H NMR (300 MHz, CD$_3$OD) δ 7.76 (d, J=8.3, 2H), 7.59 (d, J=8.3, 2H), 7.33 (s, 1H), 5.20 (dd, J=3.2, 9.4, 1H), 4.54 (dd, J=15.9, 123.4, 2H), 3.32–3.22 (m, 1H), 3.17–3.10 (m, 1H), 2.70–2.63 (m, 1H), 2.34–2.27 (m, 1H).

Example 16

(S)-3-Methanesulfonylamino-4-oxo-4,6,7,8-tetrahydro-pyrrolo[1,2-a]pyrimidine-6-carboxylic acid 4-carbamimidoyl-benzylamide Step A: (S)-[imino-(4-{[(3-methanesulfonylamino-4-oxo-4,6,7,8-tetrahydro-pyrrolo[1,2-a]pyrimidine-6-carbonyl)-amino]-methyl)-phenyl)-methyl]-carbamic acid tert-butyl ester (16a).

To a solution of 1j (50 mg, 0.117 mmol) in 0.5 mL pyridine at 0° C. was added methanesulfonyl chloride (14.8 mg, 0.129 mmol). The solution was stirred at rt for 16 h. The mixture was diluted with 50 mL EtOAc, washed with H$_2$O (2×) and brine, dried (Na$_2$SO$_4$) and concentrated to afford 13 mg (22%) of intermediate 16a. MS (ESI) 505.0 (M+H$^+$).

Step B:

Example 16

According to the procedure for the preparation of Example 1, intermediate 16a (13 mg, 0.026 mmol) was deprotected and purified to afford 6.7 mg (64%) of Example 16. MS (HR-ESI) calc'd for $C_{17}H_{21}N_6O_4S$ (M+H$^+$), found 405.1336; $^1$H NMR (300 MHz, CD$_3$OD) δ 9.10–9.05 (m, 1H), 7.95 (s, 1H), 7.73 (dd, J=1.9, 6.6, 2H), 7.54 (d, J=8.8, 2H), 5.11 (dd, J=3.3, 9.6, 1H), 4.59–4.43 (m, 2H), 3.25–3.00 (m, 2H), 3.28–2.99 (m, 3H), 2.66–2.58 (m, 1H), 2.26–2.20 (m, 1H).

Example 17

(S)-3-Benzenesulfonylamino-4-oxo-4,6,7,8-tetrahydro-pyrrolo[1,2-a]pyrimidine-6-carboxylic acid 4-carbamimidoyl-benzylamide Step A: (S)-[imino-(4-{[(3-benzenesulfonylamino-4-oxo-4,6,7,8-tetrahydro-pyrrolo[1,2-a]pyrimidine-6-carbonyl)-amino]-methyl}-phenyl)-methyl]-carbamic acid tert-butyl ester (17a).

Following a procedure similar to that for the preparation of intermediate 16a, intermediate 1j (50 mg, 0.117 mmol) and benzene sulfonyl chloride (22.8 mg, 0.129 mmol) yielded 53.6 mg (80.1%) of intermediate 17a. MS (ESI) 567.0 (M+H$^+$).

Step B:

Example 17

According to the procedure for the preparation of Example 1, intermediate 17a (53.6 mg, 0.09 mmol) was deprotected and purified to afford 13.5 mg (50%, based on fraction purified) of Example 17. MS (HR-ESI) calc'd for $C_{22}H_{23}N_6O_4S$ (M+H$^+$), found 467.1525; $^1$H NMR (300 MHz, CDCl$_3$) δ 9.18–8.98 (m, 1H), 8.97 (s, 1H), 7.85 (dd, J=1.3, 8.3, 2H), 7.76 (d, J=8.4, 2H), 7.60–7.43 (m, 5H), 5.09–4.99 (m, 1H), 4.61–4.37 (m, 2H), 3.29–2.98 (m, 2H), 2.60–2.52 (m, 1H), 2.25–2.17 (m, 1H).

Example 18

(6S, 8R)-8-Acetylamino-8-methyl-4-oxo-3-propylamino-4,6,7,8-tetrahydro-pyrrolo[1,2-a]pyrimidine-6-carboxylic acid 4-carbamimidoyl-benzylamide

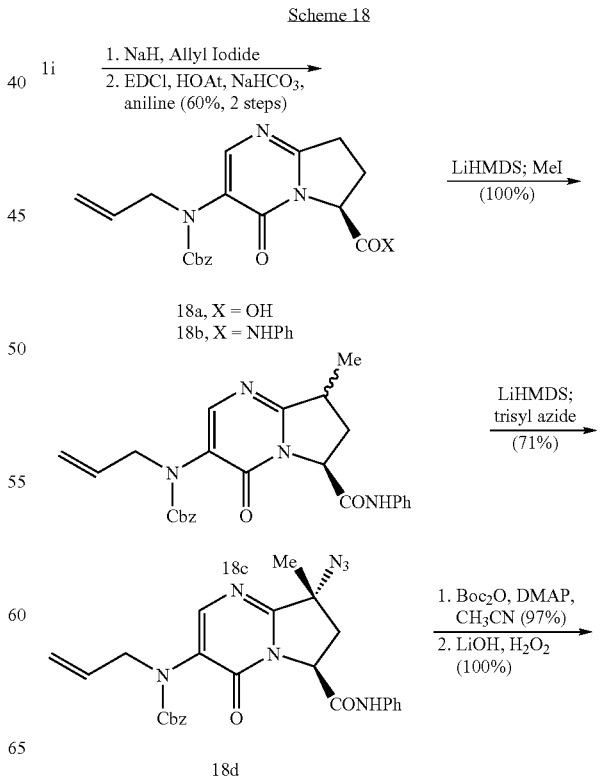

Scheme 18

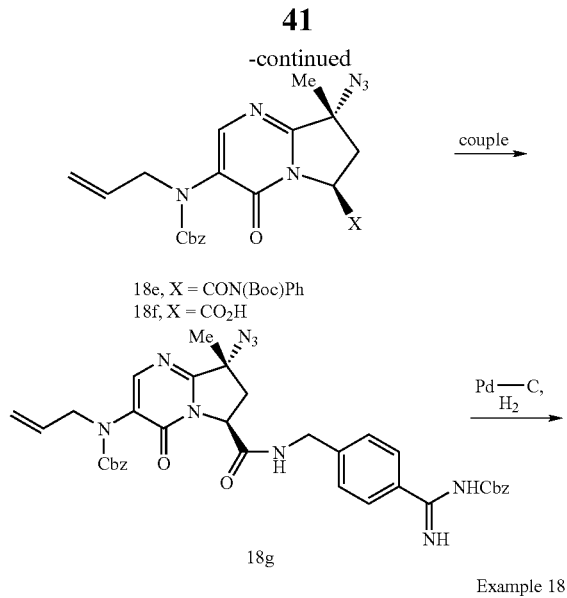

Example 18

Step A: (6S)-3-(allyl-benzyloxycarbonyl-amino)-4-oxo-4,6,7,8-tetrahydro-pyrrolo[1,2-a]pyrimidine-6-carboxylic acid (18a).

To a mixture of acid 1 h (6.00 g, 18.2 mmol) in 90 mL THF at 0° C., was added allyl iodide (2.50 mL, 27.3 mmol), and NaH (60% dispersion in oil, 2.18 g, 54.6 mmol). The reaction was stirred at rt for 15 h, then additional allyl iodide (1.67 mL, 18.2 mmol) was added. After 5 h, the reaction was quenched with the addition of H$_2$O. The volatile solvents were removed by rotary evaporation and the aqueous solution obtained was partitioned with Et$_2$O. The organic phase was extracted with 0.1 NaOH (3×). The combined organic extract was acidified with 1N HCl and extracted with EtOAc (5×). The combined organic extract was washed (brine), dried (Na$_2$SO$_4$), and concentrated to afford 6.51 g of the allyl amine (18a), which was used in the following step without additional purification.

Step B: (6S)-allyl-(4-oxo-6-phenylcarbamoyl-4,6,7,8-tetrahydro-pyrrolo[1,2-a]pyrimidin-3-yl)-carbamic acid benzyl ester (18b).

To a solution of 18a (5.50 g, 14.89 mmol) and aniline (1.93 mL, 22.3 mmol) in 75 mL 5:1 CH$_2$Cl$_2$/DMF at 0° C., was added HOAT (2.23 g, 16.4 mmol), NaHCO$_3$ (2.50 g, 29.8 mmol), and EDCI (4.00 g, 20.8 mmol). The mixture was stirred and allowed to warm to rt over 72 h. The reaction was diluted with EtOAc and the organic phase was washed with H$_2$O, 1N HCl, H$_2$O, and brine. The organic phase was dried (Na$_2$SO$_4$) and concentrated. The residue obtained was purified by flash chromatography (80 to 90% EtOAc/hexanes) to afford 3.825 g (58%, 2 steps) of 18b as an off-white solid.

Step C: (6S,8RS)-allyl-(8-methyl-4-oxo-6-phenylcarbamoyl-4,6,7,8-tetrahydro-pyrrolo[1,2-a]pyrimidin-3-yl)-carbamic acid benzyl ester (18c).

To a solution of phenyl amide 18b (3.805 g, 8.56 mmol) in 40 mL THF at −78° C., was added LiHMDS (1M in THF, 17.5 mL, 17.5 mmol). The orange solution was stirred at −78° C. for 10 min, then MeI (5.33 mL, 85.6 mmol) was added. The reaction was stirred at −78° C. for 1 h, allowed to slowly warm to −50° C. over 0.5 h with stirring, and then was quenched with the addition of sat. NH$_4$Cl. The mixture was diluted with EtOAc. The organic phase was washed with H$_2$O, 10% Na$_2$SO$_3$ (2×), and brine and dried (Na$_2$SO$_4$). The organic phase was filtered through a 2" pad of SiO$_2$, rinsing with EtOAc, and concentrated to afford 3.927 g (quantitative) of a diastereomeric mixture of methylated products (18c) as an off-white solid. MS (ESI) 459.4 (M+H$^+$), 481.4 (M+Na$^+$).

Step D: (6S,8R)-allyl-(8-azido-8-methyl-4-oxo-6-phenylcarbamoyl-4,6,7,8-tetrahydro-pyrrolo[1,2-a]pyrimidin-3-yl)-carbamic acid benzyl ester (18d).

To a solution of the methyl diastereomers (18c) (3.90 g, 8.51 mmol) in 40 mL THF at −78° C., was added LiHMDS (1M in THF, 17.9 mL, 17.9 mmol). The red solution was stirred at −78° C. for 5 min, then a solution of trisyl azide (2.90 g, 9.36 mmol) in 8 mL THF was added. The reaction was stirred at −78° C. for 1.5 h, then was quenched with the addition of AcOH (2.19 mL, 38.3 mmol). The mixture was stirred at rt for 1 h, then was diluted with EtOAc. The organic phase was washed with 1N HCl, H$_2$O and brine, dried (Na$_2$SO$_4$), and concentrated. The product was purified by flash chromatography (35 to 40% EtOAc/hexanes) to afford 2.764 g (65%) of azide 18d. MS (ESI) 500.4 (M+H$^+$), 522.4 (M+Na$^+$).

Step E: (6S,8R)-allyl-[8-azido-6-(tert-butoxycarbonyl-phenyl-aminocarbonyl)-8-methyl-4-oxo-4,6,7,8-tetrahydro-pyrrolo[1,2-a]pyrimidin-3-yl]-carbamic acid benzyl ester (18e).

To a solution of amide 18d (420 mg, 0.841 mmol) in 5 mL CH$_3$CN at rt, was added DMAP (51 mg, 0.421 mmol) and Boc$_2$O (367 mg, 1.68 mmol). The mixture was stirred at rt for 1 h, then was diluted with EtOAc. The organic phase was washed with H$_2$O, 0.1 N HCl, and brine, dried (Na$_2$SO$_4$), and concentrated. The residue obtained was purified by flash chromatography (25 to 30% EtOAc/hexanes) to afford 492 mg (98%) of imide 18e. MS (ESI) 600.5 (M+H$^+$), 622.5 (M+Na$^+$).

Step F: (6S,8R)-3-(allyl-benzyloxycarbonyl-amino)-8-azido-8-methyl-4-oxo-4,6,7,8-tetrahydro-pyrrolo[1,2-a]pyrimidine-6-carboxylic acid (18f).

To a solution of 18e (480 mg, 0.800 mmol) in 10 mL THF/H$_2$O (4:1) at 0° C., was added 30% H$_2$O$_2$ (1.28 mL, 11.3 mmol) and 1N LiOH (1.28 mL, 1.28 mmol). The mixture was stirred at 0° C. of 45 min, then Na$_2$SO$_3$ (1.51 g, 12 mmol) was added. The mixture was stirred 30 min, then evaporated in vacuo. The residue was diluted with Et$_2$O and extracted with 0.1 N NaOH (3×). The combined aqueous was acidified to pH 3 with conc. HCl, then was extracted with EtOAc (5×). The combined organic extract was washed with brine, dried (Na$_2$SO$_4$) and concentrated to afford 272 mg (80%) of a acid 18f, which was used in the following step with out further purification. MS (ESI) 447.3 (M+Na$^+$), 423.2 (M−H$^+$).

Step G: (6S,8R)-allyl-{8-azido-6-[4-(benzyloxycarbonylamino-imino-methyl)-benzylcarbamoyl]-8-methyl-4-oxo-4,6,7,8-tetrahydro-pyrrolo[1,2-a]pyrimidin-3-yl}-carbamic acid benzyl ester (18 g).

To a solution of 18f (270 mg, 0.636 mmol) and [(4-Aminomethyl-phenyl)-imino-methyl]-carbamic acid benzyl ester (272 mg, 0.763 mmol) in 6 mL CH$_2$Cl$_2$/DMF (5:1) at 0° C., were added HOAT (95 mg, 0.700 mmol), NaHCO$_3$ (187 mg, 2.23 mmol), and EDCI (171 mg, 0.890 mmol). The mixture was allowed to warm to rt and stir for 15 h. The mixture was diluted with EtOAc, washed with H$_2$O, 1 N HCl, H$_2$O, sat. NaHCO$_3$, and brine. The mixture was dried (Na$_2$SO$_4$) and concentrated to afford 393 mg (90%) of intermediate 18 g.

Step H:

Example 18

To a solution of 18 g (30 mg, 0.043 mmol) in 2 mL MeOH, was added 20 mg 10% Pd—C. The mixture was evacuated and flushed with $H_2$ (3×), then was stirred under an atmosphere of $H_2$ for 1h. The mixture was filtered, then 2 drops concentrated HCl was added. The mixture was concentrated in vacuo to afford 19.2 mg (87%) of Example 18. MS (HR-ESI) calc'd for $C_{20}H_{28}N_7O_2$ (M+H$^+$), found 398.2331; $^1$H NMR (300 MHz, $D_2O$) δ 7.60 (d, J=8.4, 2H), 7.48 (s, 1H), 7.37 (d, J=8.4, 2H), 5.17 (dd, J=3.4, 9.3, 1H), 4.46–4.31 (m, 2H), 2.99 (t, J=7.3, 2H), 2.86 (dd, J=14.6, 10.2, 1H), 2.49 (dd, J=14.6, 3.7, 1H), 1.58 (s, 3H), 1.55–1.43 (m, 2H), 0.77 (t, J=7.3, 3H).

Example 19

[6-(4-Carbamimidoyl-benzylcarbamoyl)-6-methyl-4-oxo-4,6,7,8-tetrahydro-pyrrolo[1,2-a]pyrimidin-3-yl]-carbamic acid benzyl ester Step B: 3-benzyloxycarbonylamino-6-methyl-4-oxo-4,6,7,8-tetrahydro-pyrrolo[1,2-a]pyrimidine-6-carboxylic acid (19b).

A solution of intermediate 19a (55 mg, 0.138 mmol) in 4 mL 1:1 TFA/$CH_2Cl_2$ with 2 drops water was stirred at rt for 12 h. The mixture was concentrated in vacuo, then coevaporated with $CCl_4$ to afford 50 mg of intermediate 19b (quantitative), which was used without further purification in the following step.

Step C: {6-[4-(tert-butoxycarbonylamino-imino-methyl)-benzylcarbamoyl[-6-methy[-4-oxo-4,6,7,8-tetrahydro-pyrrolo[1,2-a]pyrimidin-3-yl}-carbamic acid benzyl ester (19c).

To a solution of intermediate 19b (0.138 mmol) in 2 mL DMF at 0° C., were added iPr$_2$NEt (72,L, 0.413 mmol), BOP (74 mg, 0.166 mmol), and [(4-aminomethyl-phenyl)-imino-methyl]-carbamic acid tert-butyl ester (52 mg, 0.207 mmol).

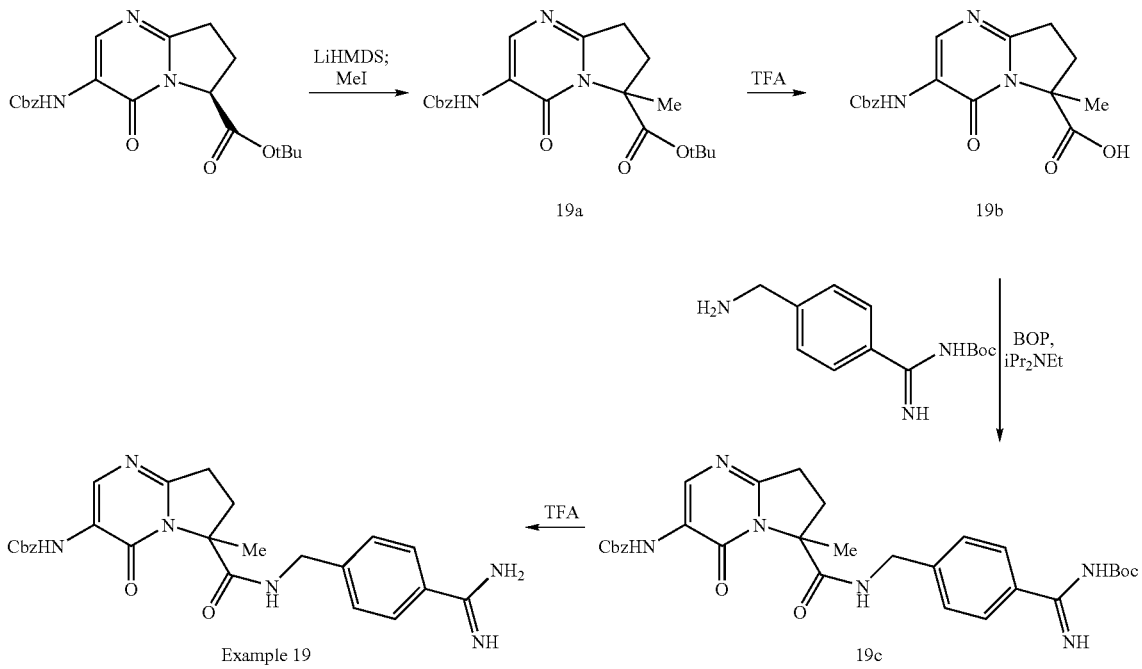

Scheme 19

Step A: 3-benzyloxycarbonylamino-6-methyl-4-oxo-4,6,7,8-tetrahydro-pyrrolo[1,2-a]pyrimidine-6-carboxylic acid tert-butyl ester (19a).

To a solution of intermediate 1g (200 mg, 0.519 mmol) in 5 mL THF at −78° C., was added a 1M solution of LIHMDS in THF (1.09 mL, 1.09 mmol). The mixture was stirred for 5 min, then MeI (162 mL, 2.60 mmol) was added. The mixture was stirred with warming to −30° C. over 1 h, then was quenched with sat. NH$_4$Cl. The mixture was diluted with EtOAc and washed with $H_2O$ and brine, dried (Na$_2$SO$_4$), and concentrated. The resultant residue was combined with additional crude material from another batch for purification by flash chromatography (stepwise gradient, 40 to 45 to 50% EtOAc/hexanes) to afford 59 mg of intermediate 19a (18%, based on 0.835 mmol of starting material). LR MS.

The mixture was allowed to slowly warm to rt and stir for 3 h. The mixture was diluted with EtOAc and washed with $H_2O$, 10% citric acid, $H_2O$, sat. NaHCO$_3$, and brine. The organic phase was dried (Na$_2$SO$_4$) and concentrated to afford 80 mg (quantitative) of intermediate 19c. LC-MS: 575.0 (M+H)

Step D:

Example 19

A mixture of intermediate 19c (79 mg, 0.138 mmol) in 4 mL 1:1 $CH_2Cl_2$/TFA was stirred at rt for 1 h, then concentrated. The crude product was purified by semipreparative HPLC (20 to 50% $CH_3CN/H_2O$) to afford 32 mg (40%) of Example 19 as the TFA salt. MS (HR-ESI) calc'd for $C_{25}H_{27}N_6O_4$ (M+H$^+$), found 475.2081;

$^1$H NMR (300 MHz, D$_2$O) δ 8.14 (s, 1H), 7.55 (d, J=8.5, 2H), 7.34 (d, J=8.5, 2H), 7.25 (s, 5H), 5.08–5.00 (m, 2H), 4.36 (s, 2H), 3.21–2.87 (m, 2H), 2.42–2.17 (m, 2H), 1.67 (s, 3H).

Example 20

[6-Allyl-6-(4-carbamimidoyl-benzylcarbamoyl)-4-oxo-4,6,7,8-tetrahydro-pyrrolo[1,2-a]pyrimidin-3-yl]-carbamic acid benzyl ester Step A: 6-allyl-3-benzyloxycarbonylamino-4-oxo-4,6,7,8-tetrahydro-pyrrolo[1,2-a]pyrimidine-6-carboxylic acid tert-butyl ester (20a).

According to the procedure for the preparation of intermediate 19a, alkylation of intermediate 1g (250 mg, 0.649 mmol) with allyl iodide afforded 153 mg (55%) of intermediate 20a. MS (ESI) 426.4 (M+H$^+$), 448.4 (M+Na$^+$).

Step B: 6-allyl-3-benzyloxycarbonylamino-4-oxo-4,6,7,8-tetrahydro-pyrrolo[1,2-a]pyrimidine-6-carboxylic acid (20b).

According to the procedure for the preparation of intermediate 19b, intermediate 20a (127 mg, 0.298 mmol) was deprotected to afford 95 mg (86%) of intermediate 20b. MS (ESI) 368.2 (M–H$^+$).

Step C: {6-allyl-6-[4-(tert-butoxycarbonylamino-imino-methyl)-benzylcarbamoyl]-4-oxo-4,6,7,8-tetrahydro-pyrrolo[1,2-a]pyrimidin-3-yl}-carbamic acid benzyl ester (20c).

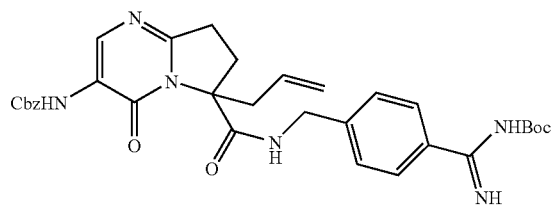

According to the procedure for the preparation of intermediate 19c, intermediate 20b (50 mg, 0.135 mmol) was coupled with [(4-aminomethyl-phenyl)-imino-methyl]-carbamic acid tert-butyl ester to afford 70 mg (86%) of intermediate 20c.

Step D:

Example 20

According to the procedure for the preparation of Example 19, Intermediate 20c (59.4 mg, 0.0989 mmol) was deprotected to afford 33 mg (54%) of Example 20 as the TFA salt. MS (HR-ESI) calc'd for $C_{27}H_{29}N_6O_4$ (M+H$^+$), found 501.2245; $^1$H NMR (300 MHz, D$_2$O) δ 8.13 (s, 1H), 7.53 (d, J=8.4, 2H), 7.32 (d, J=8.5, 2H), 7.25 (s, 5H), 5.56–5.42 (m, 1H), 5.08–4.98 (m, 2H), 4.94–4.90 (m, 2H), 4.36 (s, 2H), 3.11–2.96 (m, 2H), 2.75–2.68 (m, 11H), 2.46–2.27 (m, 2H).

Example 21

[6-benzyl-6-(4-carbamimidoyl-benzylcarbamoyl)-4-oxo-4,6,7,8-tetrahydro-pyrrolo[1,2-a]pyrimidin-3-yl]-carbamic acid benzyl ester Step A: 6-benzyl-3-benzyloxycarbonylamino-4-oxo-4,6,7,8-tetrahydro-pyrrolo[1,2-a]pyrimidine-6-carboxylic acid tert-butyl ester (21a).

According to the procedure for the preparation of intermediate 19a, alkylation of intermediate 1g (250 mg, 0.649 mmol) with benzyl bromide afforded 170 mg (55%) of intermediate 21a. MS (ESI) 476.5 (M+H$^+$), 498.5 (M+Na$^+$).

Step B: 6-benzyl-3-benzyloxycarbonylamino-4-oxo-4,6,7,8-tetrahydro-pyrrolo[1,2-a]pyrimidine-6-carboxylic acid (21b).

According to the procedure for the preparation of intermediate 19b, intermediate 21a (149 mg, 0.313 mmol) was deproteted to afford 125 mg (95%) of intermediate 21b. MS (ESI) 420.4 (M+H$^+$).

Step C: {6-benzyl-6-[4-(tert-butoxycarbonylamino-iminomethyl)-benzylcarbamoyl]-4-oxo-4,6,7,8-tetrahydro-pyrrolo[1,2-a]pyrimidin-3-yl}-carbamic acid benzyl ester (21c).

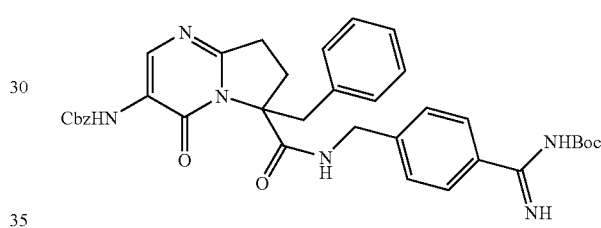

According to the procedure for the preparation of intermediate 19c, intermediate 21b (50 mg, 0.119 mmol) was coupled with [(4-aminomethyl-phenyl)-imino-methyl]-carbamic acid tert-butyl ester to afford 77 mg (quantitative) of intermediate 21c.

Step D:

Example 21

According to the procedure for the preparation of Example 19, Intermediate 21c (68.3 mg, 0.105 mmol) was deprotected to afford 47 mg (67%) of Example 21 as the TFA salt. MS (HR-ESI) calc'd for $C_{31}H_{31}N_6O_4$ (M+H$^+$), found 551.2405; $^1$H NMR (300 MHz, D$_2$O) δ 8.03 (s, 1H), 7.55 (d, J=8.4, 2H), 7.37 (d, J=8.4, 2H), 7.27–7.23 (m, 5H), 7.14–7.04 (m, 3H), 6.81 (d, J=7.0, 2H), 5.11–5.01 (m, 2H), 4.44–4.32 (m, 2H), 3.52 (d, J=13.5, 2H), 3.22 (d, J=13.5, 1H), 2.67–2.58 (m, 1H), 2.52–2.44 (m, 1H), 2.36–2.24 (m, 1H), 1.83–1.67 (m, 1H).

Example 22

[6-(4-Carbamimidoyl-benzylcarbamoyl)-6-ethyl-4-oxo-4,6,7,8-tetrahydro-pyrrolo[1,2-a]pyrimidin-3-yl]-carbamic acid benzyl ester Step A: 3-benzyloxycarbonylamino-6-ethyl-4-oxo-4,6,7,8-tetrahydro-pyrrolo[1,2-a]pyrimidine-6-carboxylic acid tert-butyl ester (22a).

According to the procedure for the preparation of intermediate 19a, alkylation of intermediate 1g (250 mg, 0.649 mmol) with ethyl iodide afforded 47 mg (18%) of intermediate 22a. MS (ESI) 414.4 (M+H⁺), 436.4 (M+Na⁺).

Step B: 3-benzyloxycarbonylamino-6-ethyl-4-oxo-4,6,7,8-tetrahydro-pyrrolo[1,2-a]pyrimidine-6-carboxylic acid (22b).

According to the procedure for the preparation of intermediate 19b, intermediate 22a (41 mg, 413.47 mmol) was deprotected to afford 35 mg (99%) of intermediate 22b. MS (ESI) 358.3 (M+H⁺), 356.2 (M−H⁺).

Step C: {6-[4-(tert-butoxycarbonylamino-imino-methyl)-benzylcarbamoyl]-6-ethyl-4-oxo-4,6,7,8-tetrahydro-pyrrolo[1,2-a]pyrimidin-3-yl}-carbamic acid benzyl ester (22c).

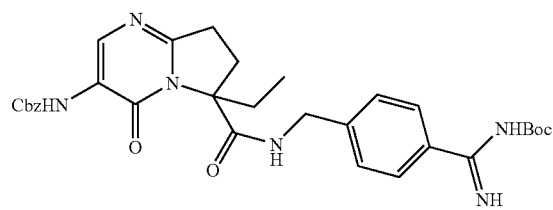

According to the procedure for the preparation of intermediate 19c, intermediate 22b (34.5 mg, 0.0965 mmol) was coupled with [(4-aminomethyl-phenyl)-imino-methyl]-carbamic acid tert-butyl ester to afford 57 mg (100%) of intermediate 22c.

Step D:

Example 22

According to the procedure for the preparation of Example 19, Intermediate 22c (51 mg, 0.087 mmol) was deprotected to afford 19.0 mg (36%) of Example 22 as the TFA salt. MS (HR-ESI) calc'd for C₂₆H₂₉N₆O₄ (M+H⁺), found 489.2261; ¹H NMR (300 MHz, D₂O) δ 8.16 (s,1H), 7.55 (d, J=8.4, 2H), 7.32 (d, J=8.4, 2H), 7.27 (s, 5H), 5.10–5.00 (m, 2H), 4.34 (s, 2H), 3.13–2.94 (m, 2H), 2.46–2.37 (m, 1H), 2.31 (t, J=8.4, 2H), 2.01–1.92 (m, 1H), 0.60 (t, J=8.4, 3H).

Example 23

[6-(4-Carbamimidoyl-benzylcarbamoyl)-6-methoxymethyl-4-oxo-4,6,7,8-tetrahydro-pyrrolo[1,2-a]pyrimidin-3-yl]-carbamic acid benzyl ester Step A: 3-benzyloxycarbonylamino-6-methoxymethyl-4-oxo-4,6,7,8-tetrahydro-pyrrolo[1,2-a]pyrimidine-6-carboxylic acid tert-butyl ester (23a).

According to the procedure for the preparation of intermediate 19a, alkylation of intermediate 1g (250 mg, 0.649 mmol) with methoxymethylchloride afforded 101 mg (36%) of intermediate 23a. MS (ESI) 430.4 (M+H⁺), 452.4 (M+Na⁺).

Step B: 3-benzyloxycarbonylamino-6-methoxymethyl-4-oxo-4,6,7,8-tetrahydro-pyrrolo[1,2-a]pyrimidine-6-carboxylic acid (23b).

According to the procedure for the preparation of intermediate 19b, intermediate 23a (87 mg, 0.203 mmol) was deprotected to afford 76 mg (quantitative) of intermediate 23b. MS (ESI) 418.3 (M 2Na⁺+H⁺), 372.2 (M−H⁺).

Step C: {6-[4-(tert-butoxycarbonylamino-imino-methyl)-benzylcarbamoyl]-6-methoxymethyl-4-oxo-4,6,7,8-tetrahydro-pyrrolo[1,2-a]pyrimidin-3-yl}-carbamic acid benzyl ester (23c).

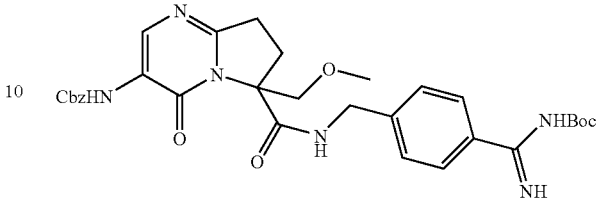

According to the procedure for the preparation of intermediate 19c, intermediate 23b (57.8 mg, 0.155 mmol) was coupled with [(4-aminomethyl-phenyl)-imino-methyl]-carbamic acid tert-butyl ester to afford 94 mg (100%) of intermediate 23c.

Step D:

Example 23

According to the procedure for the preparation of Example 19, Intermediate 23c (86 mg, 0.142 mmol) was deprotected to afford 51 mg (58%) of Example 23 as the TFA salt. MS (HR-ESI) calc'd for C₂₆H₂₆N₆O₅ (M+H⁺), found 505.2172; ¹H NMR (300 MHz, D₂O) δ 8.15 (s, 1H), 7.52 (d, J=8.4, 2H), 7.29 (d, J=8.4, 2H), 7.25 (s, 5H), 5.07–4.98 (m, 2H), 4.38–4.25 (m, 2H), 4.00–3.91 (m, 2H), 3.18 (s, 3H), 3.18–2.97 (m, 2H), 2.58–2.27 (m, 2H).

Example 24

(S)-[6-(3-Carbamoyl-benzylcarbamoyl)-4-oxo-4,6,7,8-tetrahydro-pyrrolo[1,2-a]pyrimidin-3-yl]-carbamic acid benzyl ester To a solution of Intermediate 1h (50 mg, 0.152 mmol) and 3-aminomethyl-benzamide (60 mg, 0.228 mmol) in 2 mL DMF, were added iPr₂Net (106 µL, 0.608 mmol), HOAT (41.4 mg, 0.304 mmol) and EDCI (35 mg, 0.182 mmol). The mixture was stirred at rt for 14 h, then was diluted with EtOAc. The organic phase was washed with H₂O, 1N HCl, H₂O, 0.1 N, NaOH, and brine, dried (Na₂SO₄), and concentrated. The crude product was recrystallized from methanol to afford 7.2 mg (10%) of Example 24. MS (HR-ESI) calculated for C₂₄H₂₄N₅O₅ (M+H⁺), found 462.1787; MS (ESI) 462.3 (M+H⁺), 484.3 (M+Na⁺); ¹H NMR (300 MHz, CD₃OD) δ. 8.51 (br. S, 1H), 7.84 (s, 1H), 7.78 (d, J=7.7, 1H), 7.53–7.31 (m, 7H), 5.20 (s, 2H), 5.13 (dd, J=3.0, 1.0, 1H), 4.61–4.37 (m, 2H), 3.25–3.16 (m, 1H), 3.12–3.03 (m, 1H), 2.66–2.55 (m, 1H), 2.32–2.24 (m, 1H).

Example 25

(S)-4-Oxo-3-(3-trifluoromethyl-benzylamino)-4,6,7,8-tetrahydro-pyrrolo[1,2-a]pyrimidine-6-carboxylic acid 4-carbamimidoyl-benzylamide Scheme 25

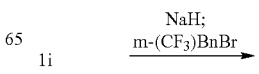

1i

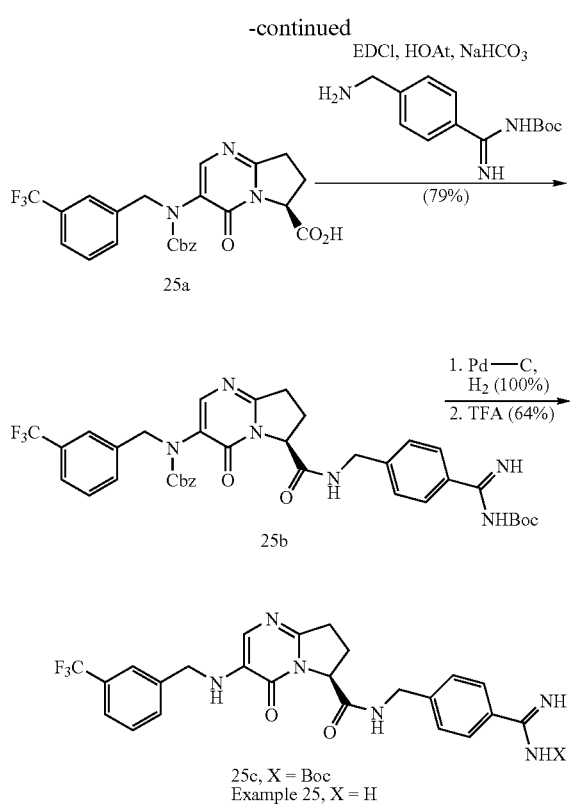

Step B: benzyl (S)-{6-[4-(tert-Butoxycarbonylamino-iminomethyl)-benzylcarbamoyl]-4-oxo-4,6,7,8-tetrahydro-pyrrolo[1,2-a]pyrimidin-3-yl}-(3-trifluoromethyl-benzyl)-carbamate (25b).

To a solution of intermediate 25a (0.281 mmol) and [(4-aminomethyl-phenyl)-imino-methyl]-carbamic acid tert-butyl ester (84 mg, 0.337 mmol) in 3 mL 5:1 $CH_2Cl_2$/DMF at 0° C., were added $NaHCO_3$ (59 mg, 0.703 mmol), HOAT (42.1 mg, 0.309 mmol), and EDCI (75.5 mg, 0.393 mmol). The mixture was allowed to warm to rt and stir 20 h, then was diluted with EtOAc. The organic phase was washed with $H_2O$, 1N HCl, $H_2O$, and sat. $NaHCO_3$, and brine, dried ($Na_2SO_4$) and brine. The crude residue was triturated with $Et_2O$ to afford 160 mg (79%) of intermediate 25b as a white solid. MS (ESI) 719.4 ($M+H^+$).

Step C: tert-butyl (S)-{imino-[4-({[4-oxo-3-(3-trifluoromethyl-benzylamino)-4,6,7,8-tetrahydro-pyrrolo[1,2-a]pyrimidine-6-carbonyl]-amino}-methyl)-phenyl]-methyl}-carbamate (25c).

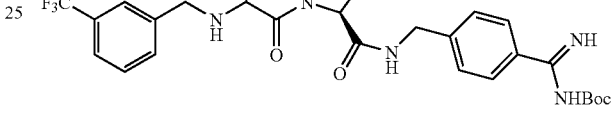

To a solution of 25b (83 mg, 0.115 mmol) in 5 mL MeOH, was added 20 mg 10% Pd—C. The mixture was evacuated and flushed 3× with $H_2$, then was stirred under an atmosphere of $H_2$ for 1 h. The mixture was filtered and concentrated to afford 67 mg (100%) of intermediate 25f. MS (ESI) 585.4 ($M+H^+$).

Step D:

Example 25

A solution of intermediate 25c (60 mg) in 3 mL TFA was stirred at rt for 2 h, then concentrated. The crude product was purified by semipreparative HPLC (gradient, 0 to 50% $CH_3CN/H_2O$) to afford 18.3 mg (25%) of Example 25. MS (HR-ESI) calc'd for $C_{24}H_{24}F_3N_6O_2$ ($M+H^+$), found 485.1899.

Example 26

(6S,8R)-8-Ethylamino-8-methyl-4-oxo-3-propylamino-4,6,7,8-tetrahydro-pyrrolo[1,2-a]pyrimidine-6-carboxylic acid 4-carbamimidoyl-benzylamide Step A: (S)-3-{[(benzyloxy)carbonyl][3-(trifluoromethyl)benzyl]amino}-4-oxo-4,6,7,8-tetrahydropyrrolo[1,2-a]pyrimidine-6-carboxylic acid (25a).

To a mixture of acid 1i (4.50 g, 13.7 mmol) in 70 mL THF at 0° C., was added 3-(trifluoromethyl)benzyl bromide (8.35 mL, 54.7 mmol), NaH (60% dispersion in oil, 1.64 g, 41.4 mmol), and TBAI (100 mg, catalytic). The reaction was stirred at rt for 15 h, then quenched with the addition of 50 mL $H_2O$. The volatile solvents were removed by rotary evaporation and the aqueous solution obtained was partitioned with $Et_2O$. The organic phase was extracted with 20% sat. $NaHCO_3$ (3×). The combined aqueous extract was acidified with 1N HCl and extracted with EtOAc (5×). The combined organic extract was washed (brine), dried ($Na_2SO_4$), and concentrated to afford 6.18 g (93%) of the 3-(trifluoromethyl)benzyl amine (25a), which was used in the following step without additional purification. MS (ESI) 488.3 ($M+H^+$), 510.3 ($M+Na^+$); 486.3 ($M-H^+$).

Scheme 26

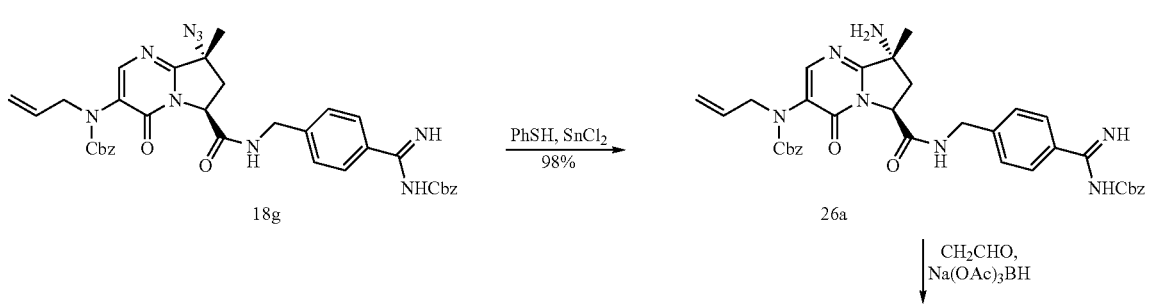

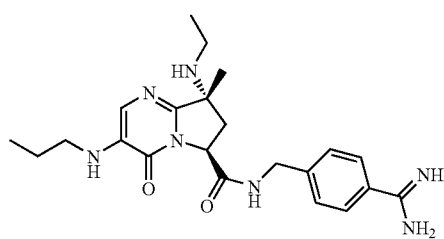

Example 26

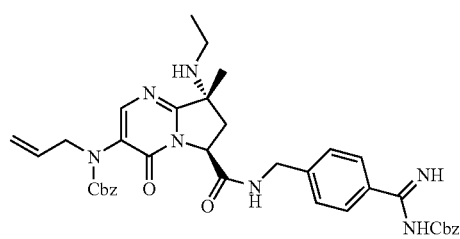

26b

Step A: (6S,8R)-allyl-{8-amino-6-[4-(benzyloxycarbonylamino-imino-methyl)-benzylcarbamoyl]-8-methyl-4-oxo-4,6,7,8-tetrahydro-pyrrolo [1,2-a]pyrimidin-3-yl}-carbamic acid benzyl ester (26a).

To a solution of $SnCl_2$ (330 mg, 1.74 mmol) in 11 mL $CH_3CN$ at rt, were added PhSH (0.715 mL, 6.96 mmol) and TEA (0.728 mL, 5.22 mmol). The mixture was stirred 5 min, then 18 g (800 mg, 1.16 mmol) was added. The mixture was stirred 15 min, then diluted with $CH_2Cl_2$ and 1N NaOH. The layers were separated and the aqueous was extracted with $CH_2Cl_2$ (2×). The combined organic extract was washed with 1N NaOH and brine, dried ($Na_2SO_4$), filtered through a pad of Celite®, and concentrated to afford 752 mg (98%) of 26a as a colorless foam. LC-MS 664.2 ($M+H^+$).

Step B: (6S,8R)-allyl-{6-[4-(benzyloxycarbonylamino-imino-methyl)-benzylcarbamoyl]-8-ethylamino-8-methyl-4-oxo-4,6,7,8-tetrahydro-pyrrolo[1,2-a]pyrimidin-3-yl}-carbamic acid benzyl ester (26b).

Following a procedure similar to that for the preparation of intermediate 1k, 26a (30.0 mg, 0.045 mmol), acetaldehyde (2.2 mg, 0.050 mmol) and $NaBH(OAc)_3$ (14.4 mg, 0.068 mmol) yielded 16.9 mg (54%) of 26b. MS (ESI) 692.5 ($M+H^+$).

Step C:

Example 26

According to the procedure for the preparation of Example 13, 26b (14.4 mg, 0.023 mmol) was deprotected and purified to afford 6.9 mg (70%) of Example 26. MS (HR-ESI) calc'd for $C_{22}H_{32}N_7O_2$ ($M+H^+$), found 427.2637; $^1$H NMR (300 MHz, $CD_3OD$) δ 7.61 (d, J=8.4, 2H), 7.37 (d, J=8.4, 2H), 7.24 (s, 1H), 5.16–5.11 (m, 1H), 4.47–4.31 (m, 2H), 3.08–2.80 (m, 5H), 2.41 (dd, J=4, 15, 11H), 1.60 (s, 3H), 1.54–1.41 (m 2H), 1.15–1.09 (m, 3H), 0.9–0.75 (m, 3H).

Example 27

(6S,8R)-8-Isopropylamino-8-methyl-4-oxo-3-propylamino-4,6,7,8-tetrahydro-pyrrolo[1,2-a]pyrimidine-6-carboxylic acid 4-carbamimidoyl-benzylamide Step A: (6S,8R)-allyl-{6-[4-(benzyloxycarbonylamino-imino-methyl)-benzylcarbamoyl]-8-isopropylamino-8-methyl-4-oxo-4,6,7,8-tetrahydro-pyrrolo[1,2-a]pyrimidin-3-yl}-carbamic acid benzyl ester (27a).

Following a procedure similar to that for the preparation of intermediate 1k, 26a (30 mg, 0.045 mmol), acetone (5.3 mg, 0.090 mmol) and $NaBH(OAc)_3$ (26.8 mg, 0.127 mmol) yielded 8.9 mg (28.1%) of 27a. MS (ESI) 706.2 ($M+H^+$).

Step B:

Example 27

According to the procedure for the preparation of Example 13, 27a (8.9 mg, 0.0126 mmol) was deprotected and purified to afford 1.1 mg (19.9%) of Example 27. MS (HR-ESI) calc'd for $C_{23}H_{34}N_7O_2$ ($M+H^+$), found 440.2793; $^1$H NMR (300 MHz, $CD_3OD$) δ 7.61–7.55 (d, J=8.4, 2H), 7.36–7.32 (d, J=8.0, 2H), 7.17 (s, 1H), 5.14–5.11 (m, 1H), 4.66–4.28 (m, 2H), 3.54–3.45 (m, 1H), 2.99–2.87 (m, 3H), 2.42 (dd, J=3.7, 15, 1H), 1.60 (s, 3H), 1.50–1.40 (m, 2H), 1.17 (d, J=6.6, 3H), 1.03 (d, J=6.6, 3H), 0.746 (t, J=7.3, 3H).

Example 28

(6S,8R)-4-Oxo-8-propyl-3-propylamino-4,6,7,8-tetrahydro-pyrrolo[1,2-a]pyrimidine-6-carboxylic acid 4-carbamimidoyl-benzylamide Scheme 28

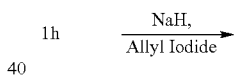

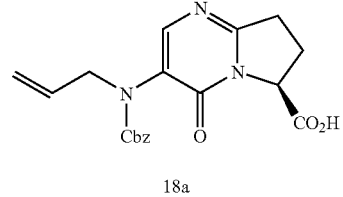

18a

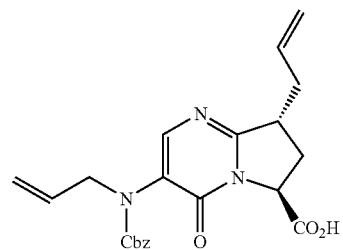

28a

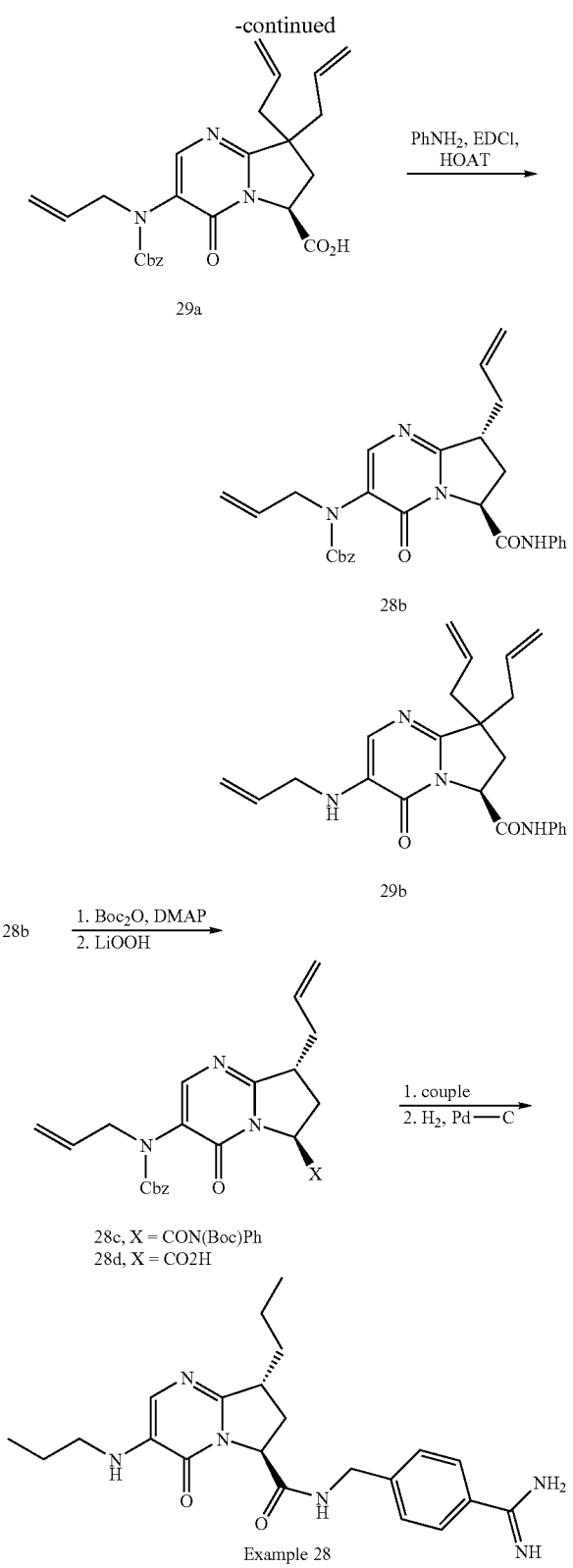

reaction was stirred at rt for 15 h, then was quenched with the addition of H$_2$O. The volatile solvents were removed by rotary evaporation and the aqueous solution obtained was partitioned with Et$_2$O. The organic phase was extracted with 0.1 NaOH (3×). The combined aqueous extract was acidified with 1N HCl and extracted with EtOAc (5×). The combined organic extract was washed (brine), dried (Na$_2$SO$_4$), and concentrated to afford 3.00 g of an 18:1:1 mixture of allyl amine 18a, di-allyl intermediate 28a, and tri-allyl intermediate 29a, which was used in the following step without additional purification.

Step B: Amide Formation—Preparation of 18b, 28b, and 29b.

To a solution of 18a/28a/29a (4.10 g, 11.1 mmol) and aniline (1.15 mL, 13.3 mmol) in 50 mL 4:1 CH$_2$Cl$_2$/DMF at 0° C., was added HOAT (1.66 g, 12.2 mmol), NaHCO$_3$ (1.87 g, 22.2 mmol), and EDCI (2.98 g, 15.4 mmol). The mixture was allowed to warm to rt and stir for 15 h. The reaction was diluted with EtOAc and the organic phase was washed with H$_2$O, 1N HCl, H$_2$O, and brine. The organic phase was dried (Na$_2$SO$_4$) and concentrated. The residue obtained was purified by flash chromatography (40 to 50 to 80 to 90% EtOAc/hexanes) to afford sequentially 400 mg of 29b, 400 mg of 28b, and 2.645 g of 18b. 28b: LC-MS 485.0 (M+H$^+$). 29b: LC-MS 525.1 (M+H$^+$).

Step C: (6S,8R)-allyl-[8-allyl-6-(tert-butoxycarbonyl-phenyl-aminocarbonyl)-4-oxo-4,6,7,8-tetrahydro-pyrrolo[1,2-a]pyrimidin-3-yl]-carbamic acid benzyl ester (28c)

To a solution of 28b (385 mg, 0.795 mmol) in 10 mL CH$_3$CN at rt, were added DMAP (49 mg, 0.398 mmol) and Boc$_2$O (347 mg, 1.59 mmol). The mixture was stirred at rt for 3 h, then was diluted with EtOAc. The organic phase was washed (H$_2$O, 1N HCl, sat. NaHCO$_3$, and brine), dried (Na$_2$SO$_4$), and concentrated. The crude product was purified by flash chromatography (30% EtOAc/hexanes) to afford 346 mg of 28c as a colorless foam. MS (ESI) 585.5 (M+H$^+$), 583.3 (M−H$^+$).

Step D: (6S,8R)-8-allyl-3-(allyl-benzyloxycarbonyl-amino)-4-oxo-4,6,7,8-tetrahydro-pyrrolo[1,2-a]pyrimidine-6-carboxylic acid (28d)

To a solution of 28c (311 mg, 0.532 mmol) in 5 mL THF/H$_2$O (4:1) at 0° C., were added 30% H$_2$O$_2$ (0.241 mL, 2.13 mmol) and IM LiOH (0.851 mL, 0.851 mmol). The mixture was stirred at 0° C. for 2 h, then Na$_2$SO$_3$ and 10 mL H$_2$O were added. The organic solvent was evaporated under a stream of nitrogen. The precipitate was filtered and rinsed with H$_2$O and 0.1 N NaOH. The combined aqueous filtrate was acidified with conc. HCl, then extracted with EtOAc (3×). The combined organic extract was washed with brine, dried (Na$_2$SO$_4$), and concentrated to afford 208 mg (96%) of 28d. MS (ESI) 410.3 (M+H$^+$), 432.3 (M+Na$^+$), 408.2 (M−H$^+$).

Step E: benzyl (6S,8R)-allyl-{8-allyl-6-[4-(benzyloxycarbonylamino-imino-methyl)-benzylcarbamoyl]-4-oxo-4,6,7,8-tetrahydro-pyrrolo[1,2-a]pyrimidin-3-yl}-carbamate (28e).

To a solution of 28d (172 mg, 0.420 mmol) and [(4-aminomethyl-phenyl)-imino-methyl]-carbamic acid benzyl ester hydrochloride (180 mg, 0.504 mmol) in 3.6 mL CH$_2$Cl$_2$/DMF (5:1) at 0° C., was added HOAT (113 mg, 0.588 mmol), NaHCO$_3$ (141 mg, 1.68 mmol), and EDCI (113 mg, 0.588 mmol). The mixture was allowed to warm to rt and stir for 64 h. The reaction was diluted with EtOAc and the organic phase was washed with H$_2$O, 1N HCl, H$_2$O, and brine. The organic phase was dried (Na$_2$SO$_4$) and concen- Step A: alkylation of intermediate 1h.

To a mixture of acid 1 h (2.55 g, 7.74 mmol) in 30 mL THF at 0° C., was added allyl iodide (1.77 mL, 19.4 mmol), and NaH (60% dispersion in oil, 929 mg, 23.2 mmol). The trated. The residue obtained was purified by flash chromatography (75% EtOAc/hexanes) to afford 59 mg of intermediate 28e.

Step F:

Example 28

To a solution of 28e (59 mg) 2 mL MeOH, were added 3 drops conc. HCl and 20 mg 10% Pd—C. The mixture was evacuate and flushed with $H_2$ (3x), then stirred under an atmosphere of $H_2$ for 1.5 h. The mixture was filtered and concentrated to afford 37 mg (88%) of Example 28. MS (HR-ESI) calc'd for $C_{22}H_{31}N_6O_2$ (M+H$^+$), found 411.2520; $^1$H NMR (300 MHz, $D_2O$) δ 7.58 (d, J=8.4, 2H), 7.33 (d, J=8.4, 2H), 7.07 (s, 1H), 5.15 (dd, J=3.0, 1.1, 1H), 4.43–4.29 (m, 2H), 3.56–3.48 (m, 1H), 2.92 (t, J=7.3, 2H), 2.44–2.30 (m, 2H), 1.78–1.69 (m, 1H), 1.51–1.39 (m, 3H), 1.25–1.17 (m, 2H), 0.74 (t, J=7.3, 6H).

Example 29

(S)-4-Oxo-8,8-dipropyl-3-propylamino-4,6,7,8-tetrahydro-pyrrolo[1,2a]pyrimidine-6-carboxylic acid 4-carbamimidoyl-benzylamide

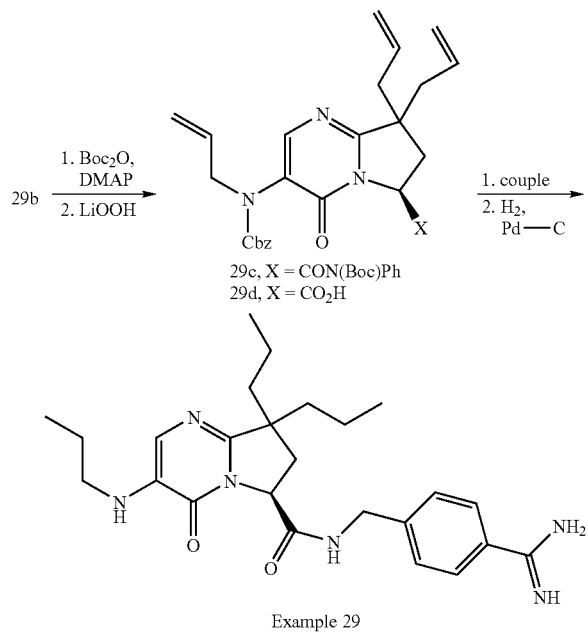

Example 29

Step A: benzyl (S)-allyl-[8,8-diallyl-6-(tert-butoxycarbonyl-phenyl-aminocarbonyl)-4-oxo-4,6,7,8-tetrahydro-pyrrolo[1,2-a]pyrimidin-3-yl]-carbamate (29c).

According to the procedure for the preparation of 28c, 29b (400 mg, 0.763 mmol) afforded after flash chromatography (25% EtOAc/hexanes) 419 mg of 29c as a colorless foam. MS (ESI) 625.5 (M+H$^+$), 623.3 (M−H$^+$).

Step B: (S)-8,8-diallyl-3-(allyl-benzyloxycarbonyl-amino)-4-oxo-4,6,7,8-tetrahydro-pyrrolo[1,2-a]pyrimidine-6-carboxylic acid (29d).

According to the procedure for the preparation of 28d, 29c (372 mg, 0.595 mmol) afforded 202 mg (76%) of 29d. MS (ESI) 450.4 (M+H$^+$), 448.2 (M−H$^+$).

Step C: benzyl (S)-allyl-{8,8-diallyl-6-[4-(benzyloxycarbonylamino-imino-methyl)-benzylcarbamoyl]-4-oxo-4,6,7,8-tetrahydro-pyrrolo[1,2-a]pyrimidin-3-yl}-carbamate (29e)

According to the procedure for the preparation of 28e, 29d (162 mg, 0.360 mmol) was coupled with [(4-aminomethyl-phenyl)-imino-methyl]-carbamic acid benzyl ester hydrochloride to afford after flash chromatography (66% EtOAc/hexanes) 105 mg (41%) of 29e. MS (ESI) 715.5 (M+H$^+$), 737.5 (M+Na$^+$).

Step D:

Example 29

According to the procedure for the preparation of Example 28, 29e (95 mg, 0.132 mmol) was hydrogenated to afford 62 mg (89%) of Example 29. MS (HR-ESI) calc'd for $C_{25}H_{37}N_6O_2$ (M+H$^+$), found 453.2978; $^1$H NMR (300 MHz, $D_2O$) δ 7.58 (d, J=8.4, 2H), 7.33 (d, J=8.4, 2H), 7.10 (s, 1H), 5.09 (dd, J=9.9, 5.9, 1H), 4.35 (s, 2H), 2.93 (t, J=7.3, 2H), 2.55 (dd, J=14.0, 9.8, 1H), 2.10 (dd, J=14.0, 5.6, 1H), 1.66–1.39 (m, 6H), 1.20–1.04 (m, 2H), 1.00–0.83 (m, 2H), 0.74 (t, J=7.3, 3H), 0.68 (t, J=6.9, 3H), 0.62 (t, J=7.3, 3H).

Example 30

(S)-3-(Naphthalene-1-sulfonylamino)-4-oxo-4,6,7,8-tetrahydro-pyrrolo[1,2-a]pyrimidine-6-carboxylic acid 4-carbamimidoyl-benzylamide Step A: (S)-{imino-[4-({[3-(naphthalene-1-sulfonylamino)-4-oxo-4,6,7,8-tetrahydro-pyrrolo[1,2-a]pyrimidine-6-carbonyl]-amino}-methyl)-phenyl]-methyl}-carbamic acid tert-butyl ester (30a).

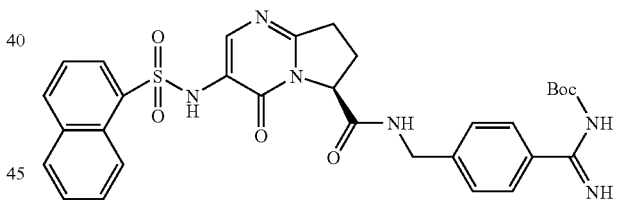

Following a procedure similar to that for the preparation of 16a, intermediate 3a (50 mg, 0.117 mmol) and 1-napthylene sulfonyl chloride (39.8 mg, 0.176 mmol) yielded 21.7 mg (30.0%) of 1-napthalene sulfonamide intermediate 30a. MS (ESI) 617.0 (M+H$^+$).

Step B:

Example 30

According to the procedure for the preparation of Example 1, intermediate 30a (21.7 mg, 0.035 mmol) was deprotected and purified to afford 3.2 mg (17.7%) of Example 18. MS (HR-ESI) calc'd for $C_{26}H_{25}N_6O_4S$ (M+H$^+$), found 517.1672; $^1$H NMR (300 MHz, $CD_3OD$) δ 8.96–8.93 (m, 1H), 8.70 (d, J=8.4, 1H), 8.23–8.20 (m, 1H), 8.10 (d, J=8.0, 1H), 7.95 (d, J=8.8, 1H), 7.79 (s, 1H), 4.90–4.83 (m, 1H), 4.50–4.30 (m, 2H), 3.28–2.92 (m, 2H), 2.50–2.41 (m, 1H), 2.16–2.11 (m, 1H).

Example 31

(S)-3-(4-Methoxy-benzenesulfonylamino)-4-oxo-4,6,7,8-tetrahydro-pyrrolo[1,2-a]pyrimidine-6-carboxylic acid 4-carbamimidoyl-benzylamide Step A: (S)-{imino-[4-({[3-(4-methoxy-benzenesulfonylamino)-4-oxo-4,6,7,8-tetrahydro-pyrrolo[1,2-a]pyrimidine-6-carbonyl]-amino}-methyl)-phenyl]-methyl}-carbamic acid tert-butyl ester (31a).

Following a procedure similar to that for the preparation of 16a, intermediate 3a (50 mg, 0.117 mmol) and 4-methoxybenzene sulfonyl chloride (31.4 mg, 0.152 mmol) yielded 32.2 mg (46.2%) of 31a. MS (ESI) 597.0 (M+H$^+$).
Step B:

Example 31

According to the procedure for the preparation of Example 1, intermediate 19 (32.2 mg, 0.054 mmol) was deprotected and purified to afford 16.2 mg (56.6%) of Example 31. MS (HR-ESI) calc'd for $C_{23}H_{25}N_6O_5S$ (M+H$^+$), found 597.1600; $^1$H NMR (300 MHz, CD$_3$OD) δ 9.10–9.01 (m, 1H), 7.96 (s, 1H), 7.80–7.74 (m, 4H), 7.54 (d, J=6.6, 8.5, 2H), 7.00–6.95 (m, 2H), 5.04–4.99 (m, 1H), 4.63–4.36 (m, 2H), 3.32–3.29 (m, 3H), 3.21–2.98 (m, 2H), 2.65–2.53 (m, 1H), 2.25–2.15 (m, 1H).

Example 32

(S)-3-(4-Fluoro-benzenesulfonylamino)-4-oxo-4,6,7,8-tetrahydro-pyrrolo[1,2-a]pyrimidine-6-carboxylic acid 4-carbamimidoyl-benzylamide Step A: (S)-{[4-({[3-(4-fluoro-benzenesulfonylamino)-4-oxo-4,6,7,8-tetrahydro-pyrrolo[1,2-a]pyrimidine-6-carbonyl]-amino}-methyl)-phenyl]-imino-methyl}-carbamic acid tert-butyl ester (32a).

Following a procedure similar to that for the preparation of 16a, intermediate 3a (50 mg, 0.117 mmol) and 4-fluorobenzene sulfonyl chloride (29.6 mg, 0.158 mmol) yielded 28.2 mg (41.0%) of 32a. MS (ESI) 585.0 (M+H$^+$).
Step B:

Example 32

According to the procedure for the preparation of Example 1, 32a (28.2 mg, 0.048 mmol) was deprotected and purified to afford 14.6 mg (63%) of Example 32. MS (HR-ESI) calc'd for $C_{22}FH_{22}N_6O_4S$ (M+H$^+$), found 485.1409; $^1$H NMR (300 MHz, CD$_3$OD) δ 8.99–8.95 (m, 1H), 7.96 (s, 1H), 7.87–7.82 (m, 2H), 7.72 (d, J=8.4, 2H), 7.50 (d, J=8.4, 2H), 7.20–7.13 (m, 2H), 4.97 (dd, J=2.9, 9.5, 1H), 4.59–4.51 (m, 1H), 4.37 (dd, J=5.1, 16.1, 1H), 3.25–2.98 (m, 2H), 2.62–2.48 (m, 1H), 2.21–2.15 (m, 1H).

Example 33

(S)-4-Oxo-3-(4-trifluoromethoxy-benzenesulfonylamino)-4,6,7,8-tetrahydro-pyrrolo[1,2-a]pyrimidine-6-carboxylic acid 4-carbamimidoyl-benzylamide Step A: (S)-{imino-[4-({[4-oxo-3-(4-trifluoromethoxy-benzenesulfonylamino)-4,6,7,8-tetrahydro-pyrrolo[1,2-a]pyrimidine-6-carbonyl]-amino}-methyl)-phenyl]-methyl}-carbamic acid tert-butyl ester (33a).

Following a procedure similar to that for the preparation of 16a, intermediate 3a (50 mg, 0.117 mmol) and 4-(trifluoromethoxy)benzene sulfonyl chloride (39.6 mg, 0.152 mmol) yielded 31.7 mg (41.6%) of 33a. MS (ESI) 651.0 (M+H$^+$).

Step B:

Example 33

According to the procedure for the preparation of Example 1, 33a (31.7 mg, 0.049 mmol) was deprotected and purified to afford 7.2 mg (26.7%) of Example 33. MS (HR-ESI) calc'd for $C_{23}F_3H_{22}N_6O_5S$ (M+H$^+$), found 551.1322; $^1$H NMR (300 MHz, CD$_3$OD) δ 7.97 (s, 1H), 7.94–7.88 (m, 2H), 7.43 (d, J=8.4, 2H), 7.50 (d, J=8.74, 2H), 7.36–7.32 (m, 2H), 5.00–4.94 (m, 1H), 4.59–4.35 (m, 2H), 3.17–2.99 (m, 2H), 2.58–2.48 (m, 1H), 2.21–2.15 (m, 1H).

Example 34

(S)-4-Oxo-3-(4-phenoxy-benzenesulfonylamino)-4,6,7,8-tetrahydro-pyrrolo[1,2-a]pyrimidine-6-carboxylic acid 4-carbamimidoyl-benzylamide Step A: (S)-{imino-[4-({[4-oxo-3-(4-phenoxy-benzenesulfonylamino)-4,6,7,8-tetrahydro-pyrrolo[1,2-I]pyrimidine-6-carbonyl]-amino}-methyl)-phenyl]-methyl}-carbamic acid tert-butyl ester (34a).

Following a procedure similar to that for the preparation of 16a, intermediate 3a (50 mg, 0.117 mmol) and [(4-phenoxy)benzene] sulfonyl chloride (40.9 mg, 0.158 mmol) yielded 30.0 mg (39.0%) of 34a. MS (ESI) 659.1 (M+H⁺).

Step B:

Example 34

According to the procedure for the preparation of Example 1, 34a (30.0 mg, 0.046 mmol) was deprotected and purified to afford 4.2 mg (16%) of Example 34. MS (HR-ESI) calc'd for $C_{28}H_{27}N_6O_5S$ (M+H⁺), found 559.1787; $^1$H NMR (300 MHz, CD$_3$OD) δ 9.01–8.97 (m, 1H), 7.91 (s, 1H), 7.71 (dd, J=8.0, 2H), 7.49 (d, J=8.0, 3H), 7.40–7.31 (m, 4H), 7.17–7.08 (m, 2H), 6.98 (dd, J=1.1, 8.6, 2H), 5.02–4.96 (dd, J=3.3, 9.5, 1H), 4.54–4.32 (m, 2H), 3.21–2.99 (m, 2H), 2.59–2.50 (m, 1H), 2.20–2.16 (m, 1H).

Example 35

(S)-3-(4-Acetyl-benzenesulfonylamino)-4-oxo-4,6,7,8-tetrahydro-pyrrolo[1,2-a]pyrimidine-6-carboxylic acid 4-carbamimidoyl-benzylamide Step A: (S)-{[4-({[3-(4-acetyl-benzenesulfonylamino)-4-oxo-4,6,7,8-tetrahydro-pyrrolo[1,2-a]pyrimidine-6-carbonyl]-amino}-methyl)-phenyl]-imino-methyl}-carbamic acid tert-butyl ester (35a).

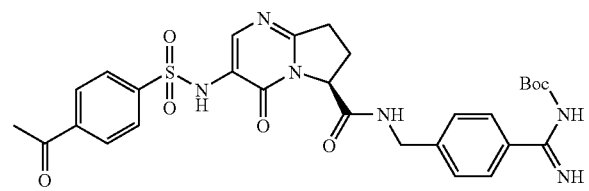

Following a procedure similar to that for the preparation of 16a, intermediate 3a (50 mg, 0.117 mmol) and 4-acetyl-benzene sulfonyl chloride (30.6 mg, 0.14 mmol) yielded 30.0 mg (42.0%) of 35a. MS (ESI) 609.1 (M+H⁺).

Step B:

Example 35

According to the procedure for the preparation of Example 1, 35a (30.0 mg, 0.049 mmol) was deprotected and purified to afford 5.8 mg (23%) of Example 35. MS (HR-ESI) calc'd for $C_{24}H_{25}N_6O_5S$ (M+H⁺), found 509.1617; $^1$H NMR (300 MHz, CD$_3$OD) δ 8.93–8.90 (m, 1H), 8.02–7.98 (m, 3H), 7.91–7.86 (m, 2H), 7.70 (d, J=8.5, 2H), 7.46 (d, J=8.4, 2H), 4.95 (dd, J=2.9, 9.5, 1H), 4.56–4.28 (m, 2H), 3.28–2.99 (m, 2H), 2.57–2.46 (m, 4H), 2.20–1.88 (m, 1H).

Example 36

(S)-4-Oxo-3-phenylmethanesulfonylamino-4,6,7,8-tetrahydro-pyrrolo[1,2-a]pyrimidine-6-carboxylic acid 4-carbamimidoyl-benzylamide Step A: (S)-[imino-(4-{[(4-oxo-3-phenylmethanesulfonylamino-4,6,7,8-tetrahydro-pyrrolo[1,2-a]pyrimidine-6-carbonyl)-amino]-methyl}-phenyl)-methyl]-carbamic acid tert-butyl ester (36a).

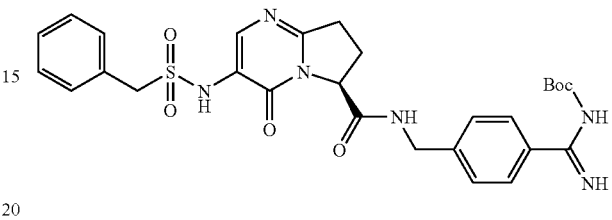

Following a procedure similar to that for the preparation of 16a, intermediate 3a (50 mg, 0.117 mmol) and alpha-toluene sulfonyl chloride (26.7 mg, 0.14 mmol) yielded 35.6 mg (44%) of 36a. MS (ESI) 581.1 (M+H⁺).

Step B:

Example 36

According to the procedure for the preparation of Example 1, intermediate 36a (35.6 mg, 0.061 mmol) was deprotected and purified to afford 8.2 mg (27.9%) of Example 36. MS (HR-ESI) calc'd for $C_{23}H_{25}N_6O_4S$ (M+H⁺), found 481.1665; $^1$H NMR (300 MHz, CD$_3$OD) δ 7.66 (s,1H), 7.46 (d, J=8.4, 2H), 7.33 (d, J=8.5, 2H), 7.20–7.13 (m, 1H), 5.05–4.99 (m, 1H), 4.61–4.23 (m, 4H), 3.15–2.91 (m, 2H), 2.60–2.46 (m, 1H), 2.21–2.12 (m, 1H).

Example 37

(S)-8,8-Diethyl-4-oxo-3-propylamino-4,6,7,8-tetrahydro-pyrrolo[1,2-a]pyrimidine-6-carboxylic acid 4-carbamimidoyl-benzylamide

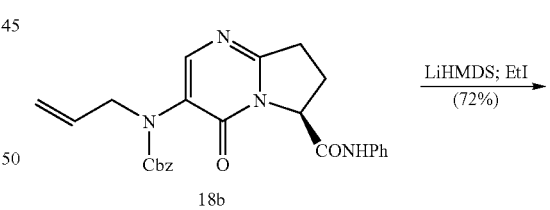

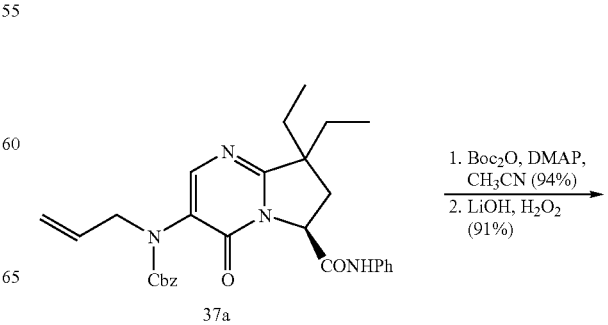

61

-continued

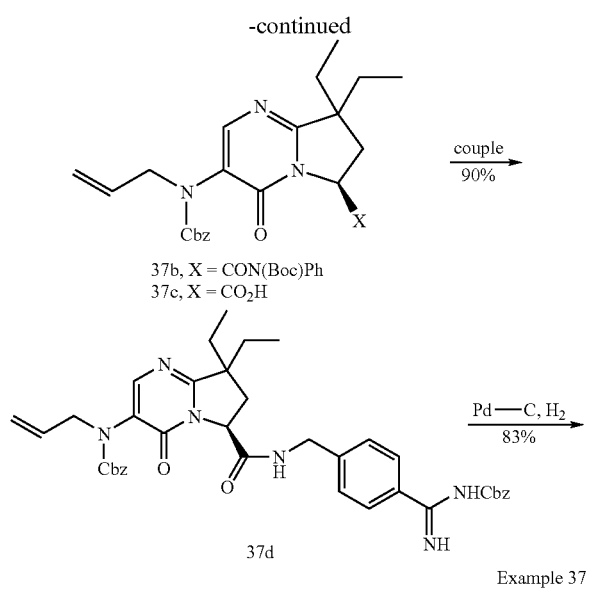

37b, X = CON(Boc)Ph
37c, X = CO₂H

37d

Example 37

Step A: (S)-allyl-(8,8-diethyl-4-oxo-6-phenylcarbamoyl-4,6,7,8-tetrahydro-pyrrolo[1,2-a]pyrimidin-3-yl)-carbamic acid benzyl ester (37a).

To a solution of phenyl amide 18b (100 mg, 0.225 mmol) in 1 mL THF at −78° C., was added LiHMDS (IM in THF, 0.720 mL, 0.720 mmol). The orange solution was stirred at −78° C. for 5 min, then EtI (0.045 mL, 0.563 mmol) was added. The reaction was stirred and allowed to slowly warm to −30° C. over 45 min. Additional LiHMDS (IM in THF, 0.250 mL, 0.250 mmol) and EtI (0.025 mL) were added and the mixture was allowed to warm to −20° C. over 30 min. The reaction was quenched with the addition of sat. NH₄Cl. The mixture was diluted with EtOAc. The organic phase was washed with H₂O and brine, dried (Na₂SO₄) and concentrated. The crude product was purified by flash chromatography (40 to 45% EtOAc/hexanes) to afford 81.1 mg (72%) of 37a as a colorless foam. MS (ESI) 501.3 (M+H⁺), 523.3 (M+Na⁺), 499.4 (M−H⁺), 535.3 (M+Cl⁻).

Step B: (S)-allyl-[6-(tert-butoxycarbonyl-phenyl-aminocarbonyl)-8,8-diethyl-4-oxo-4,6,7,8-tetrahydro-pyrrolo[1,2-I]pyrimidin-3-yl]-carbamic acid benzyl ester (37b).

According to the procedure for the preparation of intermediate 18e, intermediate 37a (75 mg, 0.150 mmol) afforded 85 mg (94%) of imide 37b. MS (ESI) 601.5 (M+H⁺), 623.5 (M+Na⁺).

Step C: (S)-3-(allyl-benzyloxycarbonyl-amino)-8,8-diethyl-4-oxo-4,6,7,8-tetrahydro-pyrrolo[1,2-a]pyrimidine-6-carboxylic acid (37c).

According to the procedure for the preparation of intermediate 18f, intermediate 37b (85 mg, 0.142 mmol) afforded 55 mg of acid 37c (91%), which was used in the following step without further purification.

Step D: (S)-allyl-{6-[4-(benzyloxycarbonylamino-iminomethyl)-benzylcarbamoyl]-8,8-diethyl-4-oxo-4,6,7,8-tetrahydro-pyrrolo[1,2-a]pyrimidin-3-yl}-carbamic acid benzyl ester (37d).

According to the procedure for the preparation of intermediate 18 g, intermediate 37c (55 mg, 0.129 mmol)

62 afforded after flash chromatography (80 to 90% EtOAc/hexanes) 80 mg (90%) of intermediate 37d. MS (ESI) 691.5 (M+H⁺), 713.5 (M+Na⁺).

Step E:

Example 37

To a solution of 37d (80 mg, 0.043 mmol) in 3 mL MeOH and 5 drops conc. HCl, was added 30 mg 10% Pd—C. The mixture was evacuated and flushed with H₂ (3×), then was stirred under an atmosphere of H₂ for 1 hour. The mixture was filtered and concentrated in vacuo to afford 47.7 mg (83%) of Example 37. MS (ESI) 425.1 (M+H⁺); ¹H NMR (300 MHz, D₂O) δ 7.58 (d, J=8.4, 2H), 7.35 (d, J=8.4, 2H), 7.12 (s, 1H), 5.07 (dd, J=3.4, 9.3, 1H), 4.41–4.32 (m, 2H), 2.93 (t, J=7.3, 2H), 2.53 (dd, J=14.6, 10.2, 1H), 2.05 (dd, J=14.6, 3.7, 1H), 1.66–1.57 (m, 4H), 1.50–1.38 (m, 2H), 0.74 (t, J=7.3, 3H), 0.65 (t, J=11.9, 6H).

Example 38

(6R,8S)-[6-(4-Carbamimidoyl-benzylcarbamoyl)-8-methyl-4-oxo-3-propylamino-4,6,7,8-tetrahydro-pyrrolo[1,2a]pyrimidin-8-yl]-acetic acid tert-butyl ester Step A: (6R,8S)-[3-(allyl-benzyloxycarbonyl-amino)-8-methyl-4-oxo-6-phenylcarbamoyl-4,6,7,8-tetrahydro-pyrrolo[1,2-a]pyrimidin-8-yl]-acetic acid tert-butyl ester (38a).

To Intermediate 18c (495.7 mg, 1.08 mmol) in THF at −78° C. was added LiHMDS (2.268 mL, 2.268 mmol) dropwise. After 10 min, tert-butyl bromoacetate was added and the mixture was stirred at −78° C. for 20 min. It was allowed to warm to −40° C. over 20 min, then quenched with NH₄Cl. The reaction mixture was diluted with EtOAc, then washed with H₂O, brine, dried (Na₂SO₄) and concentrated. It was purified by SiO₂ chromatography (50% EtOAc/hexanes) to afford 367.9 mg (59%) of intermediate 38a.

Step B: (6R,8S)-[3-(allyl-benzyloxycarbonyl-amino)-6-(tert-butoxycarbonyl-phenyl-aminocarbonyl)-8-methyl-4-oxo-4,6,7,8-tetrahydro-pyrrolo[1,2-a]pyrimidin-8-yl]-acetic acid tert-butyl ester (38b).

Following a procedure similar to that for the preparation of intermediate 18e, intermediate 38a (435.9 mg, 0.76 mmol), was protected to give 418.9 mg (82%) of intermediate 38b. MS (ESI) 673.4 (M+H⁺), 695.3 (M+Na⁺).

Step C: (6R,8S)-3-(allyl-benzyloxycarbonyl-amino)-8-tert-butoxycarbonylmethyl-8-methyl-4-oxo-4,6,7,8-tetrahydro-pyrrolo[1,2-a]pyrimidine-6-carboxylic acid (38c)

According to the procedure for the preparation of 18f, intermediate 38b (413.9 mg, 0.62 mmol) was deprotected to afford 273.9 mg (89%) of intermediate 38c. MS (ESI) 498.4 (M+H⁺), 496.2 (M−H⁺).

Step D: (6R,8S)-{3-(allyl-benzyloxycarbonyl-amino)-6-[4-(benzyloxycarbonylamino-imino-methyl)benzylcarbamoyl]-8-methyl-4-oxo-4,6,7,8-tetrahydro-pyrrolo[1,2-a]pyrimidin-8-yl}-acetic acid tert-butyl ester (38d).

Following a procedure similar to that for the preparation of 18 g, intermediate 38c (268.9 mg, 0.54 mmol) was coupled with [(4-aminomethyl-phenyl)-imino-methyl]-car bamic acid benzyl ester (223.9 mg, 0.70 mmol) to provide 262.3 mg (64%) of intermediate 38d. MS (ESI) 763.5 (M+H$^+$).

Step E:

Example 38

According to the procedure for the preparation of Example 18, intermediate 38d (33.6 mg, 0.044 mmol) was hydrogenated to afford 24.5 mg (100%) of Example 38. MS (ESI) 497.5 (M+H$^+$); MS (HR-ESI) calc'd for $C_{21}H_{37}N_6O_4$ (M+H$^+$), found 497.2868; $^1$H NMR (300 MHz, CD$_3$OD) δ 8.80 (s, 1H), 8.57 (s, 1H), 7.70 (d, J=8.1, 2H), 7.52 (d, J=8.1, 2H), 7.00 (s, 1H), 5.59–5.51 (m, 1H), 4.53 (dd, J=15.7. 150.1, 2H), 3.3/–3.08 (m, 2H), 3.06 (t, J=7.2, 2H), 2.93 (d, J=16.5, 1H), 2.71–2.53 (m, 2H), 2.79–2.62 (m, 5H), 1.43 (s, 9H), 1.01–0.95 (t, J=7.5, 3H).

Example 39

(6R,8S)-[6-(4-Carbamimidoyl-benzylcarbamoyl)-8-methyl-4-oxo-3-propylamino-4,6,7,8-tetrahydro-pyrrolo[1,2-a]pyrimidin-8-yl]-acetic acid Step A: (6R,8S)-{3-(allyl-benzyloxycarbonyl-amino)-6-[4-(benzyloxycarbonylamino-imino-methyl)-benzylcarbamoyl]-8-methyl-4-oxo-4,6,7,8-tetrahydro-pyrrolo[1,2-a]pyrimidin-8-yl}-acetic acid (39a).

A solution of intermediate 38d (262.3 mg, 0.34 mmol) in 5 mL 4M HCl dioxane was stirred at rt for 2 h. The solvent was removed in vacuo, then the compound was triturated with ether to afford 245 mg (100%) of intermediate 39a. MS (ESI) 707.4 (M+H$^+$), 705.3 (M–H$^+$).

Step B:

Example 39

According to the procedure for the preparation of Example 18, intermediate 39a (15 mg, 0.021 mmol) was hydrogenated to afford 9.8 mg (100%) of Example 39. MS (ESI) 441.4 (M+H$^+$), 439.3 (M–H+); MS (HR-ESI) calc'd for $C_{22}H2_9N_6O_4$ (M+H$^+$), found 441.2252; $^1$H NMR (300 MHz, CD$_3$OD) δ 7.78 (d, J=8.4, 2H), 7.62 (d, J=8.4, 2H), 7.08 (s, 11H), 5.27 (t, J=6.3, 11H), 4.70–4.44 (m, 2H), 3.14 (t, J=7.1, 2H), 3.00 (dd, J=16.9, 34.4, 2H), 2.70–2.55 (m, 2H), 1.78–1.58 (m, 5H), 1.03 (t, J=7.4, 3H).

Example 40

(6R,8S)-8-Methyl-4-oxo-8-phenylcarbamoylmethyl-3-propylamino-4,6,7,8-tetrahydro-pyrrolo[1,2-a]pyrimidine-6-carboxylic acid 4-carbamimidoyl-benzylamide Step A: (6R,8S)-allyl-{6-[4-(benzyloxycarbonylamino-imino-methyl)-benzylcarbamoyl]-8-methyl-4-oxo-8-phenylcarbamoylmethyl-4,6,7,8-tetrahydro-pyrrolo[1,2-a]pyrimidin-3-yl}-carbamic acid benzyl ester (40a).

Following a procedure similar to that for the preparation of intermediate 18 g, intermediate 39a (20 mg, 0.028 mmol) was coupled with aniline (3.39 mg, 0.036 mmol) to provide 12.4 mg (57%) of intermediate 40a. MS (ESI) 782.3 (M+H$^+$).

Step B:

Example 40

According to the procedure for the preparation of Example 18, intermediate 40a (12.4 mg, 0.015 mmol) was hydrogenated to afford 7.2 mg (93%) of Example 40. MS (ESI) 516.4 (M+H$^+$); MS (HR-ESI) calc'd for $C_{28}H_{34}N_7O_3$ (M+H$^+$), found 516.2734; $^1$H NMR (300 MHz, CD$_3$OD) δ 7.68 (d, J=8.4, 2H), 7.59–7.50 (m, 4H), 7.33–7.22 (m, 2H), 7.11–7.02 (m, 2H), 5.24–5.18 (m, 1H), 4.61–4.41 (m, 2H), 3.09–3.03 (m, 5H), 2.70–2.55 (m, 2H), 1.69–1.58 (m, 2H), 1.57 (s, 3H), 0.97 (t, J=7.5, 3H).

Example 41

(6R,8S)-8-Methyl-4-oxo-8-(2-oxo-2-piperidin-1-yl-ethyl)-3-propylamino-4,6,7,8-tetrahydro-pyrrolo[1,2-a]pyrimidine-6-carboxylic acid 4-carbamimidoyl-benzylamide Step A: (6R,8S)-allyl-[6-[4-(benzyloxycarbonylamino-imino-methyl)-benzylcarbamoyl]-8-methyl-4-oxo-8-(2-oxo-2-piperidin-1-yl-ethyl)-4,6,7,8-tetrahydro-pyrrolo[1,2-a]pyrimidin-3-yl]-carbamic acid benzyl ester (41a).

Following a procedure similar to that for the preparation of intermediate 18 g, intermediate 39a (20 mg, 0.028 mmol) was coupled with piperidine (8.1 mg, 0.14 mmol) to provide 15.7 mg (71%) of intermediate 41a. MS (ESI) 774.5 (M+H$^+$).

Step B:

Example 41

According to the procedure for the preparation of Example 18, intermediate 41a (15.7 mg, 0.020 mmol) was hydrogenated to afford 10.4 mg (100%) of Example 41. MS (ESI) 508.5 (M+H$^+$); MS (HR-ESI) calc'd for $C_{27}H_{38}N_7O_3$ (M+H$^+$), found 508.3044; $^1$H NMR (300 MHz, CD$_3$OD) δ 7.75 (d, J=8.4, 2H), 7.57 (d, J=8.4, 2H), 7.00 (s, 1H), 5.19 (t, J=8.1, 1H), 4.51 (d, J=16.1, 1H), 4.39 (d, J=16.1, 1H), 3.52–3.42 (m, 4H), 3.15 (d, J=6.3, 2H), 3.06 (t, J=7.1, 2H), 2.68–2.38 (m, 2H), 1.71–1.42 (m, 11H), 0.97 (t, J=7.5, 3H).

Example 42

(6R,8S)-8-Formylamino-8-methyl-4-oxo-3-propylamino-4,6,7,8-tetrahydro-pyrrolo[1,2-a]pyrimidine-6-carboxylic acid 4-carbamimidoyl-benzylamide Step A: (6R,8S)-allyl-{6-[4-(benzyloxycarbonylamino-imino-methyl)-benzylcarbamoyl]-8-formylamino-8-methyl-4-oxo-4,6,7,8-tetrahydro-pyrrolo[1,2-a]pyrimidin-3-yl}-carbamic acid benzyl ester (42a)

To a solution of DCC (18.6 mg, 0.090 mmol) and formic acid (8.28 mg, 0.180 mmol) in CH$_2$Cl$_2$ that had been stirred at 0° C. for 10 min, was added intermediate 26a (30 mg, 0.045) in a solution of pyridine. The reaction was stirred at 0° C. for 15m then at rt for 2 h. The reaction mixture was concentrated in vacuo, then taken up in brine and extracted with chloroform (6×), dried (Na$_2$SO$_4$) and concentrated. It was purified by SiO$_2$ chromatography (gradient elution, 1–12% MeOH/CH$_2$Cl$_2$) to afford 23.3 mg (75%) of intermediate 42a. MS (ESI) 692.2 (M+H$^+$).

Step B:

Example 42

According to the procedure for the preparation of Example 18, intermediate 42a (23.3 mg, 0.034 mmol) was hydrogenated to afford 11.3 mg (78%) of Example 42. MS (ESI) 426.5 (M+H$^+$); MS (HR-ESI) calc'd for C$_{211}$H$_{28}$N$_7$O$_3$ (M+H$^+$), found 426.2256; $^1$H NMR (300 MHz, CD$_3$OD) δ 7.95 (s, 11H), 7.75 (d, J=8.4, 2H), 7.57 (d, J=8.4, 2H), 7.06 (s, 1H), 5.21 (dd, J=3.5, 10.3, 1H), 4.52 (dd, J=16.1, 83.5, 2H), 3.10–2.95 (m, 3H), 2.33 (dd, J=3.4, 13.9, 1H), 1.70–1.59 (m, 5H), 0.97 (t, J=7.3, 3H).

Example 43

(6R,8S)-8-Methyl-4-oxo-3-propylamino-8-ureido-4,6,7,8-tetrahydro-pyrrolo[1,2-a]pyrimidine-6-carboxylic acid 4-carbamimidoyl-benzylamide Step A: (6R,8S)-Allyl-{6-[4-(benzyloxycarbonylamino-imino-methyl)- enzylcarbamoyl]-8-methyl-4-oxo-8-ureido-4,6,7,8-tetrahydro-pyrrolo[1,2-a]pyrimidin-3-yl}-carbamic acid benzyl ester (43a).

To a solution of intermediate 26a in CH$_2$Cl$_2$, was added phenethyl isocyanate (8.68 mg, 0.059 mmol). The mixture was stirred for 4 h. Additional phenethyl isocyanate (1.99 mg, 0.0135 mmol) was added, then the reaction was stirred for 19 h. The compound was purified by SiO$_2$ chromatography (gradient elution: 0–10% MeOH/CH$_2$Cl$_2$) to provide 37.7 mg (100%) of intermediate 43a. MS (ESI) 811.2 (M+H$^+$).

Step B:

Example 43

According to the procedure for the preparation of Example 18, intermediate 43a (35.3 mg, 0.044 mmol) was hydrogenated to afford 14.4 mg (74%) of Example 43. MS (ESI) 441.5 (M+H$^+$); MS (HR-ESI) calc'd for C$_{21}$H$_{29}$N$_8$O$_3$ (M+H$^+$), found 441.2381; $^1$H NMR (300 MHz, CD$_3$OD) δ 9.25–9.18 (m, 1H), 7.77 (d, J=8.4, 2H), 7.56 (d, J=8.4, 2H), 7.03 (s, 1H), 5.24 (dd, J=3.0, 10.7, 1H), 4.66 (d, J=15.9, 2H), 4.40 (d, J=15.9, 1H), 3.11–2.97 (m, 3H), 2.28 (dd, J=3.3, 13.5, 1H), 1.70–1.56 (m, 5H), 0.97 (t, J=7.4, 3H).

Various analogs synthesized using Schemes and methods disclosed herein are listed in the Table 1 below.

TABLE 1

| # | R1 | R2 | R4 | R5 | R6 | X" | MS |
|---|----|----|----|----|----|----|----|
| 1 | benzyl | H | H | H | H | 4-amidinobenzyl | 417.2053 |
| 2 | phenethyl | H | H | H | H | 4-amidinobenzyl | 431.2203 |
| 3 | ethyl | Et | H | H | H | 4-amidinobenzyl | 383.2211 |
| 4 | isopropyl | H | H | H | H | 4-amidinobenzyl | 369.4 |
| 5 | ethyl | H | H | H | H | 4-amidinobenzyl | 355.1887 |
| 6 | cyclopentyl | H | H | H | H | 4-amidinobenzyl | 395.2200 |
| 7 | isobutyl | H | H | H | H | 4-amidinobenzyl | 383.2208 |
| 8 | propyl | H | H | H | H | 4-amidinobenzyl | 369.2036 |
| 9 | i-butyl | i-Bu | H | H | H | 4-amidinobenzyl | 439.2833 |
| 10 | s-butyl | H | H | H | H | 4-amidinobenzyl | 383.2201 |
| 11 | 1-ethylpropyl | H | H | H | H | 4-amidinobenzyl | 397.2367 |
| 12 | 4-pentanoic acid benzyl ester | H | H | H | H | 4-amidinobenzyl | 517.2584 |
| 13 | 4-pentanoic acid | H | H | H | H | 4-amidinobenzyl | 427.3 |
| 14 | benzyl—OC(=O) | H | H | H | H | 4-amidinobenzyl | 461.1938 |
| 15 | H | H | H | H | H | 4-amidinobenzyl | 327.3 |
| 16 | methyl—SO$_2$— | H | H | H | H | 4-amidinobenzyl | 405.1336 |
| 17 | phenyl—SO$_2$— | H | H | H | H | 4-amidinobenzyl | 467.1525 |
| 18 | propyl | H | Me | NH$_2$ | H | 4-amidinobenzyl | 398.2331 |
| 19 | benzyl—OC(=O) | H | H | H | methyl | 4-amidinobenzyl | 475.2081 |
| 20 | benzyl—OC(=O) | H | H | H | allyl | 4-amidinobenzyl | 501.2245 |
| 21 | benzyl—OC(=O) | H | H | H | benzyl | 4-amidinobenzyl | 551.2405 |
| 22 | benzyl—OC(=O) | H | H | H | ethyl | 4-amidinobenzyl | 489.2261 |
| 23 | benzyl—OC(=O) | H | H | H | MeO—methyl | 4-amidinobenzyl | 505.2172 |
| 24 | benzyl—OC(=O) | H | H | H | H | 3-carbamoylbenzyl | 462.1787 |
| 25 | 3-(CF$_3$)—benzyl | H | H | H | H | 4-amidinobenzyl | 485.1899 |
| 26 | propyl | H | Et—NH— | Me | H | 4-amidinobenzyl | 427.2637 |
| 27 | propyl | H | 2-Pr—NH— | Me | H | 4-amidinobenzyl | 440.2793 |
| 28 | propyl | H | Pr | H | H | 4-amidinobenzyl | 411.2520 |
| 29 | propyl | H | Pr | Pr | H | 4-amidinobenzyl | 453.2978 |
| 30 | naphthyl-1-SO$_2$— | H | H | H | H | 4-amidinobenzyl | 517.1672 |

TABLE 1-continued

[Chemical structure with R¹R²N, R⁴, R⁵, R⁶, X″ substituents on a pyrrolopyrimidinone-carboxamide scaffold]

| # | R1 | R2 | R4 | R5 | R6 | X″ | MS |
|---|---|---|---|---|---|---|---|
| 31 | 4-MeO—phenyl—SO₂— | H | H | H | H | 4-amidinobenzyl | 597.1600 |
| 32 | 4-F—phenyl—SO₂— | H | H | H | H | 4-amidinobenzyl | 485.1409 |
| 33 | 4-CF₃O—phenyl—SO₂— | H | H | H | H | 4-amidinobenzyl | 551.1322 |
| 34 | 4-phenoxy-phenyl—SO₂— | H | H | H | H | 4-amidinobenzyl | 559.1787 |
| 35 | 4-acetyl-phenyl—SO₂— | H | H | H | H | 4-amidinobenzyl | 509.1617 |
| 36 | benzyl—SO₂— | H | H | H | H | 4-amidinobenzyl | 481.1665 |
| 37 | propyl | H | Et | Et | H | 4-amidinobenzyl | 425.1 |
| 38 | propyl | H | tert-butyl acetate | Me | H | 4-amidinobenzyl | 497.2868 |
| 39 | propyl | H | acetate | Me | H | 4-amidinobenzyl | 441.2252 |
| 40 | propyl | H | phenylcarbamoyl-methyl | Me | H | 4-amidinobenzyl | 516.2734 |
| 41 | propyl | H | 2-oxo-2-piperidin-1-yl-ethyl | Me | H | 4-amidinobenzyl | 508.3044 |
| 42 | propyl | H | formylamino | Me | H | 4-amidinobenzyl | 426.2256 |
| 43 | propyl | H | ureido | Me | H | 4-amidinobenzyl | 441.2381 |

Utility

The compounds of the present invention are inhibitors of factor VIIa and are useful as anticoagulants for the prevention or treatment of thromboembolic disorders in mammals. In general, a thromboembolic disorder is a circulatory disease caused by blood clots (i.e., diseases involving fibrin formation, platelet activation, and/or platelet aggregation). The term "thromboembolic disorders" as used herein includes arterial or venous cardiovascular or cerebovascular thromboembolic disorders, and thromboembolic disorders in the chambers of the heart. The term "thromboembolic disorders" as used herein also includes specific disorders selected from, but not limited to, unstable angina or other acute coronary syndromes, first or recurrent myocardial infraction, ischemic sudden death, transient ischemic attack, stroke, atherosclerosis, peripheral occlusive arterial disease, venous thrombosis, deep vein thrombosis, thrombophlebitis, arterial embolism, coronary and cerebral arterial thrombosis, cerebral embolism, kidney embolisms, pulmonary embolisms, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis. It is noted that thrombosis includes occlusion (e.g. after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy. The anticoagulant effect of compounds of the present invention is believed to be due to inhibition of serine proteases involved in the coagulation cascade, more specifically, inhibition of the coagulation factors: factor VIa, factor IXa, factor Xa, factor XIa or thrombin.

The effectiveness of compounds of the present invention as inhibitors of the coagulation factors VIIa, IXa, Xa, XIa, or thrombin, can be determined using a relevant purified serine protease, respectively, and an appropriate synthetic substrate. The rate of hydrolysis of the chromogenic substrate by the relevant serine protease was measured both in the absence and presence of compounds of the present invention. Hydrolysis of the substrate resulted in the release of pNA, which was monitored spectrophotometrically by measuring the increase in absorbance at 405 nM, or the release of AMC (amino methylcoumarin, which was monitored spectrofluorometrically by measuring the increase in emission at 460 nM with excitation at 380 nM. A decrease in the rate of absorbance change at 405 nM in the presence of inhibitor is indicative of enzyme inhibition. Such methods are known to one skilled in the art. The results of this assay are expressed as inhibitory constant, $K_i$.

Factor VIIa determinations were made in 0.007 M calcium chloride, 0.1 M sodium chloride, 0.05 M trizma base containing 0.1% human serum albumin at a pH of 7.4. Determinations were made using purified human factor VIIa (Heamatologic Technologies Inc., Essex Jct., Vt.) at a final assay concentration of 2–5 nM, soluble tissue factor at a concentration of 28 nM and the synthetic substrate S-2288 (Chromogenix) at a concentration of 0.001 M. Compounds tested in the assay for Factor VIIa are considered to be active if they exhibit a $K_i$ of equal to or less than 25 μM. Preferred compounds of the present invention have $K_i$'s of equal to or less than 1 μM. More preferred compounds of the present invention have $K_i$'s of equal to or less than 0.1 μM. Even more preferred compounds of the present invention have $K_i$'s of equal to or less than 0.01 μM. Compounds of the present invention have demonstrated $K_i$ values of equal to or less than 25 µM in the assay for Factor VIIa, thereby confirming the utility of the compounds of the present invention as effective inhibitors of coagulation factor VIIa.

Factor IXa determinations were made in 0.005 M calcium chloride, 0.1 M sodium chloride, 0.05 M trizma base and 0.5% Carbowax PEG 8000 at a pH of 7.4. Determinations were made using purified human factor IXa (Haematologic Technologies) at a final assay concentration of 50–100 nM and the synthetic substrate PCIXA2100-B (CenterChem) at a concentration of 0.0002–0.0004 M. Compounds tested in the factor IXa assay are considered to be active if they exhibit a $K_i$ of equal to or less than 25 µM.

Factor Xa determinations were made in 0.1 M sodium phosphate buffer at a pH of 7.4 containing 0.2 M sodium chloride and 0.5% Carbowax PEG 8000. Determinations of the Michaelis constant, Km, for substrate hydrolysis were made using purified human factor Xa (Heamatologic Technologies Inc., Essex Jct., Vt.) at a final assay concentration of 0.5 nM and the synthetic substrate S-2222 (Chromogenix) at a concentration of 0.0002–0.0004 M. Compounds tested in the factor Xa assay are considered to be active if they exhibit a $K_i$ of equal to or less than 25 µM.

Factor XIa determinations were made in 50 mM HEPES buffer at pH 7.4 containing 145 mM NaCl, 5 mM KCl, and 0.1% PEG 8000 (polyethylene glycol; JT Baker or Fisher Scientific). Determinations were made using factor XIa at a final concentration of 75–200 µM (Haematologic Technologies) and the synthetic substrate S-2366 (Chromogenix) at a concentration of 0.0002–0.00025 M. Compounds tested in the factor XIa assay are considered to be active if they exhibit a $K_i$ of equal to or less than 25 µM.

Thrombin determinations were made in 0.1 M sodium phosphate buffer at a pH of 7.4 containing 0.2M sodium chloride and 0.5% Carbowax PEG 8000. Determinations were made using purified human alpha Thrombin (Heamatologic Technologies Inc., Essex Jct., Vt.) at a final assay concentration of 0.25 nM and the synthetic substrate S-2366 (Chromogenix) at a concentration of 0.0002 M. Compounds tested in the thrombin assay are considered to be active if they exhibit a Ki of equal to or less than 25 µM.

Compounds of the present invention have demonstrated $K_j$ values of equal to or less than 25 µM in at least one of the above assays, thereby confirming the utility of the compounds of the present invention as effective inhibitors of the coagulation cascade and useful as anticoagulants for the prevention or treatment of thromboembolic disorders in mammals.

The Michaelis constant, $K_m$, for substrate hydrolysis by each protease was determined at 25° C. using the method of Lineweaver and Burk. Values of $K_i$ were determined by allowing the protease to react with the substrate in the presence of the inhibitor. Reactions were allowed to go for periods of 20–180 minutes (depending on the protease) and the velocities (rate of absorbance change vs. time)were measured. The following relationship was used to calculate $K_i$ values:

$(v_o-v_s)/v_s=I/(K_i(1+S/K_m))$ for a competitive inhibitor with one binding site; or $v_s/v_o=A+((B-A)/1+((IC_{50}/(I)^n)))$ and $K_i=IC_{50}/(1+S/K_m)$ for a competitive inhibitor where:
$v_o$ is the velocity of the control in the absence of inhibitor;
$v_s$ is the velocity in the presence of inhibitor;
I is the concentration of inhibitor;
A is the minimum activity remaining (usually locked at zero);
B is the maximum activity remaining (usually locked at 1.0);
n is the Hill coefficient, a measure of the number and cooperativity of potential inhibitor binding sites;
$IC_{50}$ is the concentration of inhibitor that produces 50% inhibition under the assay conditions;
$K_i$ is the dissociation constant of the enzyme:inhibitor complex;
S is the concentration of substrate; and
$K_m$ is the Michaelis constant.

The effectiveness of compounds of the present invention as inhibitors of the coagulation factors XIa, VIIa, IXa, Xa, or thrombin, can be determined using relevant in vivo thrombosis models, including In Vivo Electrically-induced Carotid Artery Thrombosis Models and In Vivo Rabbit Arterio-venous Shunt Thrombosis Models.

In Vivo Electrically-induced Carotid Artery Thrombosis Model:

The antithrombotic effect of compounds of the present invention can be demonstrated in the electrically-induced carotid artery thrombosis (ECAT) model in rats. In this model, rats are anesthetized with a mixture of ketamine (110 mg/kg i.m.) and xylazine (10 mg/kg i.m.). A femoral vein and a femoral artery are isolated and catheterized. The carotid artery is also isolated such that its blood flow can be measured with a calibrated flow probe that is linked to a flowmeter. A stainless steel bipolar hook electrode is placed on the carotid artery and positioned caudally in relationship to the flow probe as a means of applying electrical stimulus. In order to protect the surrounding tissue, a piece of Parafilm is placed under the electrode.

Test compounds are considered to be effective as anticoagulants based on their ability to maintain blood flow in the carotid artery following the induction of thrombosis by an electrical stimulus. A test compound or vehicle is given as continuous intravenous infusion via the femoral vein, starting 1 hour before electrical stimulation and continuing to the end of the test. Thrombosis is induced by applying a direct electrical current of 4 mA for 3 min to the external arterial surface, using a constant current unit and a d.c. stimulator. The carotid blood flow is monitored and the time to occlusion (decrease of blood flow to zero following induction of thrombosis) in minutes is noted. The change in observed blood flow is calculated as a percentage of the blood flow prior to induction of thrombosis and provides a measure of the effect of a test compound when compared to the case where no compound is administered. This information is used to estimate the $ED_{50}$ value, the dose that increases blood flow to 50% of the control (blood flow prior to induction of thrombosis) and is accomplished by nonlinear least square regression.

In Vivo Rabbit Arterio-venous Shunt Thrombosis Model:

The antithrombotic effect of compounds of the present invention can be demonstrated in a rabbit arterio-venous (AV) shunt thrombosis model. In this model, rabbits weighing 2–3 kg anesthetized with a mixture of xylazine (10 mg/kg i.m.) and ketamine (50 mg/kg i.m.) are used. A saline-filled AV shunt device is connected between the femoral arterial and the femoral venous cannulae. The AV shunt device consists of a piece of 6-cm tygon tubing that contains a piece of silk thread. Blood will flow from the femoral artery via the AV-shunt into the femoral vein. The exposure of flowing blood to a silk thread will induce the formation of a significant thrombus. After forty minutes, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The ID50 values (dose which produces 50% inhibition of thrombus formation) are estimated by linear regression.

The compounds of Formula (I) may also be useful as inhibitors of serine proteases, notably human thrombin, plasma kallikrein and plasmin. Because of their inhibitory action, these compounds are indicated for use in the prevention or treatment of physiological reactions, blood coagulation and inflammation, catalyzed by the aforesaid class of enzymes. Specifically, the compounds have utility as drugs for the treatment of diseases arising from elevated thrombin activity such as myocardial infarction, and as reagents used as anticoagulants in the processing of blood to plasma for diagnostic and other commercial purposes.

Some compounds of the present invention may be shown to be direct acting inhibitors of the serine protease thrombin by their ability to inhibit the cleavage of small molecule substrates by thrombin in a purified system. In vitro inhibition constants may be determined by the method described by Kettner et al. in *J. Biol. Chem.* 1990, 265, 18289–18297, herein incorporated by reference. In these assays, thrombin-mediated hydrolysis of the chromogenic substrate S2238 (Helena Laboratories, Beaumont, Tex.) are monitored spectrophotometrically. Addition of an inhibitor to the assay mixture results in decreased absorbance and is indicative of thrombin inhibition. Human thrombin (Heamatologic Technologies Inc., Essex Jct., Vt.) at a concentration of 0.2 nM in 0.10 M sodium phosphate buffer, pH 7.5, 0.20 M NaCl, and 0.5% PEG 6000, is incubated with various substrate concentrations ranging from 0.20 to 0.02 mM. After 25 to 30 minutes of incubation, thrombin activity is assayed by monitoring the rate of increase in absorbance at 405 nm that arises owing to substrate hydrolysis. Inhibition constants are derived from reciprocal plots of the reaction velocity as a function of substrate concentration using the standard method of Lineweaver and Burk.

The compounds of the present invention can be administered alone or in combination with one or more additional therapeutic agents. These include other anti-coagulant or coagulation inhibitory agents, anti-platelet or platelet inhibitory agents, thrombin inhibitors, or thrombolytic or fibrinolytic agents.

The compounds are administered to a mammal in a therapeutically effective amount. By "therapeutically effective amount" it is meant an amount of a compound of Formula (I) that, when administered alone or in combination with an additional therapeutic agent to a mammal, is effective to treat (i.e. prevent, inhibit or ameliorate) the thromboembolic disease condition or treat the progression of the disease in a host.

The compounds of the invention are preferably administered alone to a mammal in a therapeutically effective amount. However, the compounds of the invention can also be administered in combination with an additional therapeutic agent, as define below, to a mammal in a therapeutically effective amount. When administered in a combination, the combination of compounds is preferably, but not necessarily, a synergistic combination. Synergy, as described for example by Chou and Talalay, *Adv. Enzyme Regul.* 1984, 22, 27–55, occurs when the effect (in this case, inhibition of the desired target) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased antiviral effect, or some other beneficial effect of the combination compared with the individual components.

By "administered in combination" or "combination therapy" it is meant that the compound of Formula (I) and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect. Compounds which can be administered in combination with the compounds of the present invention include, but are not limited to, anticoagulants, anti-thrombin agents, anti-platelet agents, fibrinolytics, hypolipidemic agents, antihypertensive agents, and anti-ischemic agents.

Other anticoagulant agents (or coagulation inhibitory agents) that may be used in combination with the compounds of this invention include warfarin, heparin, low molecular weight heparin (for example LOVANOX™), as well as other factor VIIa, VIIIa, IXa, Xa, XIa, prothrombin, TAFI, and fibrinogen inhibitors known in the art.

The term anti-platelet agents (or platelet inhibitory agents), as used herein, denotes agents that inhibit platelet function such as by inhibiting the aggregation, adhesion or granular secretion of platelets. Such agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicyclic acid or ASA), and piroxicam are preferred. Other suitable anti-platelet agents include clopidrogel and ticlopidine, including pharmaceutically acceptable salts or prodrugs thereof. Ticlopidine is also a preferred compound since it is known to be gentle on the gastro-intestinal tract in use. Still other suitable platelet inhibitory agents include IIb/IIIa antagonists, thromboxane-A2-receptor antagonists and thromboxane-A2-synthetase inhibitors, prostacyclin mimetics, phosphodiesterase (PDE) inhibitors, such as dipyridamole or cilostazol, serotonin-2-receptor antagonists, and P2Y1 and P2Y12 receptor antagonists, as well as pharmaceutically acceptable salts or prodrugs thereof.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin and argatroban, including pharmaceutically acceptable salts and prodrugs thereof. Boroarginine derivatives and boropeptides include N-acetyl and peptide derivatives of boronic acid, such as C-terminal a-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin. Boropeptide thrombin inhibitors include compounds described in Kettner et al., U.S. Pat. No. 5,187,157 and European Patent Application Publication Number 293 881 A2, the disclosures of which are hereby incorporated herein by reference. Other suitable boroarginine derivatives and boropeptide thrombin inhibitors include those disclosed in PCT Application Publication Number 92/07869 and European Patent Application Publication Number 471,651 A2, the disclosures of which are hereby incorporated herein by reference.

The term thrombolytics (or fibrinolytic) agents (or thrombolytics or fibrinolytics), as used herein, denotes agents that lyse blood clots (thrombi). Such agents include tissue plasminogen activator (TPA), anistreplase, urokinase, streptokinase, PAI-I inhibitors, and inhibitors of x-2-antiplasmin, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

The term hypolipidemic agents, as used herein, includes HMG-CoA reductase inhibitors (for example, pravastatin, simvastatin, atorvastatin, and the like) and microsomal triglyceride transport protein inhibitors.

The term antihypertensive agents, as used herein, includes angiotensin-converting enzyme inhibitors (for example captopril, lisinopril, or fosinopril), angiotensin-II receptor antagonists (for example irbestatin, losartan, or valsartan), ACE/NEP inhibitors (for example omapatrilat or gemopatrilat) and O-blockers (for example propanolol, nadolo, or carvedilol).

Administration of the compounds of Formula (I) of the invention in combination with such additional therapeutic agent, may afford an efficacy advantage over the compounds and agents alone, and may do so while permitting the use of lower doses of each. A lower dosage minimizes the potential of side effects, thereby providing an increased margin of safety.

The compounds of the present invention are also useful as standard or reference compounds, for example as a quality standard or control, in tests or assays involving the inhibition of factor VIIa, IXa, Xa and/or XIa. Such compounds may be provided in a commercial kit, for example, for use in pharmaceutical research involving factor VIIa, IXa, Xa and/or XIa. For example, a compound of the present invention could be used as a reference in an assay to compare its known activity to a compound with an unknown activity. This would ensure the experimentor that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving factor VIIa, IXa, Xa, and/or XIa. For example, the presence of factor VIIa, IXa, Xa and/or XIa in an unknown sample could be determined by addition of the relevant chromogenic substrate, example S2222 for factor Xa, to a series of solutions containing test sample and optionally one of the compounds of the present invention. If production of pNA is observed in the solutions containing test sample, but not in the presence of a compound of the present invention, then one would conclude factor Xa was present.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl-or propyl-paraben, and chlorobutanol.

Suitable pharmaceutical carriers are described in *Remington's Pharmaceutical Sciences*, Mack Publishing Company, a standard reference text in this field.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where the compounds of the present invention are administered in combination with an anti-platelet agent, by way of general guidance, typically a daily dosage may be about 0.01 to 25 milligrams of the compound of Formula I and about 50 to 150 milligrams of the anti-platelet agent, preferably about 0.1 to 1 milligrams of the compound of Formula I and about 1 to 3 milligrams of antiplatelet agents, per kilogram of patient body weight.

Where the compounds of Formula I are administered in combination with thrombolytic agent, typically a daily dosage may be about 0.1 to 1 milligrams of the compound of Formula I, per kilogram of patient body weight and, in the case of the thrombolytic agents, the usual dosage of the thrombolyic agent when administered alone may be reduced by about 70–80% when administered with a compound of Formula I.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

What is claimed is:

1. A compound of Formula (I):

(I)

or a stereoisomer or pharmaceutically acceptable salt form thereof, wherein:

$A^1$ is —$CH_2$; wherein $A^1$ is optionally substituted with 0–2 $R^{14}$;

X is —C(O)NH—$(CR^{16}R^{16})_n$—$R^8$, —$S(O)_2$NH—$(CR^{16}R^{16})_n$—$R^8$, —$CR^{15}R^{15}$—NHC(=O)—$(CR^{16}R^{16})_n$—$R^8$, —$CR^{15}R^{15}$—$NHS(=O)_2$—$(CR^{16}R^{16})_n$—$R^8$, or —$CR^{16}R^{16}$—NH—$R^8$;

n is 0, 1, or 2;

$R^1$ is H, $C_1$–$C_6$ alkyl substituted with 0–3 $R^{2b}$, $C_2$–$C_6$ alkenyl substituted with 0–3 $R^{2b}$, $C_2$–$C_6$ alkynyl substituted with 0–3 $R^{2b}$, $C_3$–$C_{10}$ carbocycle substituted with 0–3 $R^{2c}$, aryl substituted with 0–3 $R^{2c}$, or 5–10 membered heterocycle consisting of carbon atoms and 1–4 heteroatoms selected from the group: O, S, and N, and substituted with 0–3 $R^{2c}$;

$R^2$ is H, —C(=O)$R^{2a}$, —C(=O)O$R^{2a}$, —C(=O)N$R^{2a}R^{2a}$, —S(=O)$R^{2a}$, —S(=O)$_2R^{2a}$, —S(=O)$_2$N$R^{2a}R^{2a}$, $C_1$–$C_6$ alkyl substituted with 0–3 $R^{2b}$, $C_2$–$C_6$ alkenyl substituted with 0–3 $R^{2b}$, $C_2$–$C_6$ alkynyl substituted with 0–3 $R^{2b}$, $C_3$–$C_{10}$ carbocycle substituted with 0–3 $R^{2c}$, aryl substituted with 0–3 $R^{2c}$, or 5–10 membered heterocycle consisting of carbon atoms and 1–4 heteroatoms selected from the group: O, S, and N, and substituted with 0–3 $R^{2c}$;

each $R^{2a}$ is, independently at each occurrence, H, $C_1$–$C_6$ alkyl substituted with 0–3 $R^{2b}$, $C_2$–$C_6$ alkenyl substituted with 0–3 $R^{2b}$, $C_2$–$C_6$ alkynyl substituted with 0–3 $R^{2b}$, $C_3$–$C_{10}$ carbocycle substituted with 0–3 $R^{2c}$, aryl substituted with 0–3 $R^{2c}$, or 5–10 membered heterocycle consisting of carbon atoms and 1–4 heteroatoms selected from the group: O, S, and N, and substituted with 0–3 $R^{2c}$;

provided when $R^2$ is —S(=O)$R^{2a}$ or —S(=O)$_2R^{2a}$, then $R^{2a}$ is not H;

each $R^{2b}$ is, independently at each occurrence, H, F, Cl, Br, I, $NO_2$, CN, —NCS, —$CF_3$, —$OCF_3$, —$CH_3$, —$CH_2CH_3$, —CH($CH_3$)$_2$, —$OCH_3$, =O, OH, $CO_2$H, $NH_2$, NH($CH_3$), N($CH_3$)$_2$, $CO_2R^{21}$, —C(=O)N$R^{21}R^{21}$, —NHC(=O)$R^{21}$, —$NR^{21}R^{21}$, —$NHSO_2R^{21}$, —$SO_2R^{21}$, —$SO_2NR^{21}R^{21}$, —$OR^{21a}$, —$SR^{21a}$, C(=O)$R^{21a}$, —S(=O)$R^{21a}$, $C_1$–$C_4$ haloalkyl, $C_1$–$C_4$ haloalkoxy, $C_3$–$C_{10}$ carbocycle substituted with 0–3 $R^{2c}$, aryl substituted with 0–3 $R^{2c}$, or 5–10 membered heterocycle consisting of carbon atoms and 1–4 heteroatoms selected from the group: O, S, and N, and substituted with 0–3 $R^{2c}$;

each $R^{2c}$ is, independently at each occurrence, H, F, Cl, Br, I, $NO_2$, CN, —NCS, —$CF_3$, —$OCF_3$, —$CH_3$, —$OCH_3$, =O, OH, $CO_2$H, $NH_2$, NH($CH_3$), N($CH_3$)$_2$, $CO_2R^{21}$, —C(=O)N$R^{21}R^{21}$, —NHC(=O)$R^{21}$, —$NR^{21}R^{21}$, —$NHSO_2R^{21}$, —$SO_2R^{21}$, —$SO_2NR^{21}R^{21}$, —$OR^{21a}$, —$SR^{21a}$, —C(=O)$R^{21a}$, —S(=O)$R^{21a}$, $C_1$–$C_4$ haloalkyl, $C_1$–$C_4$ haloalkoxy, $C_1$–$C_4$ alkyl substituted with 0–3 $R^{2d}$, $C_2$–$C_4$ alkenyl substituted with 0–3 $R^{2d}$, $C_2$–$C_4$ alkynyl substituted with 0–3 $R^{2d}$, $C_3$–$C_6$ carbocycle substituted with 0–3 $R^{2d}$, ($C_3$–$C_6$ carbocycle)$C_1$–$C_4$ alkyl- substituted with 0–3 $R^{2d}$, (aryl)$C_1$–$C_4$ alkyl- substituted with 0–5 $R^{2d}$, or 5–6 membered heterocycle consisting of carbon atoms and 1–4 heteroatoms selected from the group: O, S, and N, and substituted with 0–4 $R^{2d}$;

each $R^{2d}$ is, independently at each occurrence, H, F, Cl, Br, I, $NO_2$, CN, —NCS, —$CF_3$, —$OCF_3$, —$CH_3$, —$OCH_3$, =O, OH, $CO_2$H, $NH_2$, NH($CH_3$), N($CH_3$)$_2$, $CO_2R^{21}$, —C(=O)N$R^{21}R^{21}$, —NHC(=O)$R^{21}$, —$NR^{21}R^{21}$, —$NHSO_2R^{21}$, —$SO_2R^{21}$, —$SO_2NR^{21}R^{21}$, —$OR^{21a}$, —$SR^{21a}$, —C(=O)$R^{21a}$, —S(=O)$R^{21a}$, $C_1$–$C_4$ alkyl, $C_1$–$C_4$ alkoxy, $C_1$–$C_4$ haloalkyl, or $C_1$–$C_4$ haloalkoxy;

$R^3$ is H, F, Cl, Br, I, $C_1$–$C_6$ alkyl substituted with 0–3 $R^{3a}$, $C_2$–$C_6$ alkenyl substituted with 0–3 $R^{3a}$, $C_2$–$C_6$ alkynyl substituted with 0–3 $R^{3a}$, $C_3$–$C_{10}$ carbocycle substituted with 0–3 $R^{3b}$, aryl substituted with 0–3 $R^{3b}$, or 5–10 membered heterocycle consisting of carbon atoms and 1–4 heteroatoms selected from the group: O, S, and N, and substituted with 0–3 $R^{3b}$;

each $R^{3a}$ is, independently at each occurrence, H, F, Cl, Br, I, $NO_2$, CN, —NCS, —$CF_3$, —$OCF_3$, —$CH_3$, —$OCH_3$, =O, OH, $CO_2$H, $NH_2$, NH($CH_3$), N($CH_3$)$_2$, $CO_2R^{21}$, —C(=O)N$R^{21}R^{21}$, —NHC(=O)$R^{21}$, —$NR^{21}R^{21}$, —$NHSO_2R^{21}$, —$SO_2R^{21}$, —$SO_2NR^{21}R^{21}$, —$OR^{21a}$, —$SR^{21a}$, —C(=O)$R^{21a}$, —S(=O)$R^{21a}$, $C_1$–$C_4$ haloalkyl, $C_1$–$C_4$ haloalkoxy, $C_3$–$C_{10}$ carbocycle substituted with 0–3 $R^{3b}$, aryl substituted with 0–3 $R^{3b}$, or 5–10 membered heterocycle consisting of carbon atoms and 1–4 heteroatoms selected from the group: O, S, and N, and substituted with 0–3 $R^{3b}$;

each $R^{3b}$ is, independently at each occurrence, H, F, Cl, Br, I, $NO_2$, CN, —NCS, —$CF_3$, —$OCF_3$, —$CH_3$, —$OCH_3$, =O, OH, $CO_2$H, $NH_2$, NH($CH_3$), N($CH_3$)$_2$, $CO_2R^{21}$, —C(=O)N$R^{21}R^{21}$, —NHC(=O)$R^{21}$, —$NR^{21}R^{21}$, —$NHSO_2R^{21}$, —$SO_2R^{21}$, —$SO_2NR^{21}R^{21}$, —$OR^{21a}$, —$SR^{21a}$, —C(=O)$R^{21a}$, —S(=O)$R^{21a}$, $C_1$–$C_6$ alkyl, $C_2$–$C_6$ alkenyl, $C_2$–$C_6$ alkynyl, $C_1$–$C_4$ haloalkyl, $C_1$–$C_4$ haloalkoxy, $C_3$–$C_{10}$ carbocycle substituted with 0–3 $R^{3c}$, aryl substituted with 0–3 $R^{3c}$, or 5–10 membered heterocycle consisting of carbon atoms and 1–4 heteroatoms selected from the group: O, S, and N, and substituted with 0–3 $R^{3c}$;

each $R^{3c}$ is, independently at each occurrence, H, F, Cl, Br, I, $NO_2$, CN, —NCS, —$CF_3$, —$OCF_3$, —$CH_3$, —$OCH_3$, =O, OH, $CO_2$H, $NH_2$, NH($CH_3$), N($CH_3$)$_2$, $CO_2R^{21}$, —C(=O)N$R^{21}R^{21}$, —NHC(=O)$R^{21}$, —$NR^{21}R^{21}$, —$NHSO_2R^{21}$, —$SO_2R^{21}$, —$SO_2NR^{21}R^{21}$, —$OR^{21a}$, —$SR^{21a}$, —C(=O)$R^{21a}$, —S(=O)$R^{21a}$, $C_1$–$C_4$ alkyl, $C_1$–$C_4$ alkoxy, $C_1$–$C_4$ haloalkyl, or $C_1$–$C_4$ haloalkoxy;

$R^4$ is H, halo, —$CF_3$, —$OCF_3$, OH, CN, $NO_2$, —$OR^{22}$, —$SR^{22}$, —$NR^{22}R^{23}$, —C(=O)$R^{22}$, —C(=O)N$R^{22}R^{23}$, —$NR^{24}$C(=O)$R^{22}$, —$NR^{24}$C(=O)N$R^{22}R^{23}$, —$NR^{24}$C(=O)N$R^{24}$C(=O)$R^{22}$, —C(=O)O$R^{22}$, —OC(=O)$R^{22}$, —OC(=O)O$R^{22}$, —$NR^{24}$C(=O)O$R^{22}$, —OC(=O)N$R^{22}R^{23}$, —S(=O)$R^{22}$, —S(=O)$_2R^{22}$, —S(=O)N$R^{22}R^{23}$, —S(=O)$_2NR^{22}R^{23}$, —$NR^{24}$S(=O)$_2NR^{22}R^{23}$, —$NR^{24}$S(=O)$R^{22}$, —$NR^{24}$S(=O)$_2R^{22}$, $C_1$–$C_4$ haloalkyl, $C_1$–$C_8$ alkoxy, ($C_1$–$C_4$ haloalkyl)oxy, $C_1$–$C_8$ alkyl substituted with 0–3 $R^{4a}$, $C_2$–$C_8$ alkenyl substituted with 0–3 $R^{4a}$, $C_2$–$C_8$ alkynyl substituted with 0–3 $R^{4a}$, $C_3$–$C_{10}$ carbocycle substituted with 0–3 $R^{26}$, aryl substituted with 0–5 $R^{26}$, or 5–10 membered heterocycle containing from 1–4 heteroatoms selected from the group consisting of N, O, and S, and substituted with 0–3 $R^{27}$;

each $R^{4a}$ is, independently at each occurrence, H, halo, —$CF_3$, —$OCF_3$, OH, CN, $NO_2$, —$OR^{22}$, —$SR^{22}$, —$NR^{22}R^{23}$, —C(=O)$R^{22}$, —C(=O)$NR^{22}R^{23}$, —$NR^{24}$C(=O)$R^{22}$, —$NR^{24}$C(=O)$NR^{22}R^{23}$, —$NR^{24}$C(=O)$NR^{24}$C(=O)$R^{22}$, —C(=O)$OR^{22}$, —OC(=O)$R^{22}$, —OC(=O)$OR^{22}$, —$NR^{24}$C(=O)$OR^{22}$, —OC(=O)$NR^{22}R^{23}$, —S(=O)$R^{22}$, —S(=O)$_2$$R^{22}$, —S(=O)$NR^{22}R^{23}$, —S(=O)$_2$$NR^{22}R^{23}$, —$NR^{24}$S(=O)$_2$$NR^{22}R^{23}$, —$NR^{24}$S(=O)$R^{22}$, —$NR^{24}$S(=O)$_2$$R^{22}$, $C_1$–$C_4$ haloalkyl, $C_1$–$C_8$ alkoxy, $C_1$–$C_4$ haloalkyl)oxy, $C_3$–$C_{10}$ carbocycle substituted with 0–3 $R^{26}$, aryl substituted with 0–5 $R^{26}$, or 5–10 membered heterocycle containing from 1–4 heteroatoms selected from the group consisting of N, O, and S, and substituted with 0–3 $R^{27}$;

$R^5$ is H, halo, $C_{1-4}$ haloalkyl, $C_1$–$C_8$ alkyl substituted with 0–3 $R^{4a}$, $C_2$–$C_8$ alkenyl substituted with 0–3 $R^{4a}$, $C_2$–$C_8$ alkynyl substituted with 0–3 $R^{4a}$, $C_3$–$C_{10}$ carbocycle substituted with 0–3 $R^{26}$, aryl substituted with 0–5 $R^{26}$, or 5–10 membered heterocycle containing from 1–4 heteroatoms selected from the group consisting of N, O, and S, and substituted with 0–3 $R^{27}$;

alternatively, $R^4$ and $R^5$ may be joined together with the carbon atom to which they are attached to form: $C_3$–$C_{10}$ carbocycle substituted with 0–3 $R^{26}$, or 5–10 membered heterocycle containing from 1–4 heteroatoms selected from the group consisting of N, O, and S, and substituted with 0–3 $R^{27}$;

$R^6$ is H, $C_1$–$C_4$ alkyl, $C_2$–$C_4$ alkenyl, aryl($C_1$–$C_3$ alkyl)-, or $C_1$–$C_4$ alkoxyalkyl;

$R^8$ is phenyl substituted with one $R^{8a}$ and 0–2 $R^{8b}$, 5–6 membered heteroaryl group comprising carbon atoms and 1, 2, or 3 heteroatoms selected from N, O, S, SO, and $SO_2$, wherein said 5–6 membered heteroaryl is substituted with one $R^{8a}$ and 0–2 $R^{8b}$, 9–10 membered bicyclic carbocycle, wherein said 9–10 membered bicyclic carbocycle contains at least one aromatic ring, and is substituted with one $R^{8a}$ and 0–2 $R^{8b}$, or 9–10 membered bicyclic heterocycle comprising carbon atoms and 1, 2, or 3 heteroatoms selected from N, O, S, SO, and $SO_2$, wherein said 9–10 membered bicyclic heterocycle contains at least one aromatic ring, and substituted with one $R^{8a}$ and 0–2 $R^{8b}$;

each $R^{8a}$ is, independently at each occurrence, $C_1$–$C_6$ alkyl, F, Cl, Br, I, OH, —$CF_3$, —$OCF_3$, —$OCH_3$, —$OCH_2CH_3$, —$OCH(CH_3)_2$, —$OCH_2CH_2CH_3$, CN, $NO_2$, $NH_2$, NH($C_1$–$C_3$ alkyl), N($C_1$–$C_3$ alkyl)$_2$, —C(=NH)$NH_2$, —C(=O)$NH_2$, —$CH_2NH_2$, —$CH_2$NH($C_1$–$C_3$ alkyl), —$CH_2$N($C_1$–$C_3$ alkyl)$_2$, —$CH_2CH_2NH_2$, —$CH_2CH_2$NH($C_1$–$C_3$ alkyl), —$CH_2CH_2$N($C_{1-3}$ alkyl)$_2$, —(CR$^{18}$R$^{19}$)$_t$C(=NR$^{18}$)NR$^{17}$R$^{19}$, —(CR$^{18}$R$^{19}$)$_t$C(=NR$^{17}$)NR$^{18}$R$^{19}$, —(CR$^{18}$R$^{19}$)$_t$NHC(=NR$^{18}$)NR$^{17}$R$^{19}$, —(CR$^{18}$R$^{19}$)$_t$NHC(=NR$^{17}$)NR$^{18}$R$^{19}$, —(CR$^{18}$R$^{19}$)$_t$NR$^{17}$C(=NR$^{18}$)NR$^{18}$R$^{19}$, —(CR$^{18}$R$^{19}$)$_t$NR$^{18}$CH(=NR$^{17}$), —(CR$^{18}$R$^{19}$)$_t$NR$^{17}$CH(=NR$^{18}$), —(CR$^{18}$R$^{19}$)$_t$C(=O)H, —(CR$^{18}$R$^{19}$)$_t$C(=O)R$^{20}$, —(CR$^{18}$R$^{19}$)$_t$NR$^{18}$R$^{19}$, —(CR$^{18}$R$^{19}$)$_t$C(=O)NR$^{18}$R$^{19}$, —(CR$^{18}$R$^{19}$)$_t$NR$^{19}$C(=O)R$^{20}$, —(CR$^{18}$R$^{19}$)$_t$OR$^{20}$, —(CR$^{18}$R$^{19}$)$_t$S(=O)NR$^{18}$R$^{19}$, —(CR$^{18}$R$^{19}$)$_t$S(=O)$_2$NR$^{18}$R$^{19}$, —(CR$^{18}$R$^{19}$)$_t$NR$^{19}$S(=O)R$^{20}$, —(CR$^{18}$R$^{19}$)$_t$NR$^{19}$S(=O)$_2$R$^{20}$, —(CR$^{18}$R$^{19}$)$_t$SR$^{20}$, —(CR$^{18}$R$^{19}$)$_t$S(=O)R$^{20}$, or —(CR$^{18}$R$^{19}$)$_t$S(=O)$_2$R$^{20}$;

provided that the moiety S(=O)$R^{20}$ forms other than S(=O)H, and the moiety S(=O)$_2$$R^{20}$ forms other than S(=O)$_2$H;

each $R^{8b}$ is, independently at each occurrence, H, halogen, $C_1$–$C_4$ alkyl, $C_1$–$C_4$ alkoxy, OH, —$CF_3$, —$OCF_3$, CN, $NO_2$, —C(=O)$NH_2$, $NH_2$, NH($C_1$–$C_3$ alkyl), or —N($C_1$–$C_3$ alkyl)$_2$;

each $R^{14}$ is, independently at each occurrence, H, $C_1$–$C_6$ alkyl, $C_2$–$C_6$ alkenyl, $C_2$–$C_6$ alkynyl, OH, $C_1$–$C_6$ alkoxy, $NH_2$, NH($C_1$–$C_3$ alkyl), N($C_1$–$C_3$ alkyl)$_2$, $C_2$–$C_6$ alkoxyalkyl-, $C_2$–$C_6$ alkylaminoalkyl-, or $C_3$–$C_6$ dialkylaminoalkyl-;

each $R^{15}$ is, independently at each occurrence, H, F, methyl, ethyl, or propyl;

alternatively, —CR$^{15}$R$^{15}$— forms a gem disubstituted cyclopropyl, cyclobutyl, cyclopentyl, or cyclohexyl group;

each $R^{16}$ is, independently at each occurrence, H, methyl, ethyl, propyl, butyl, phenyl, or benzyl;

each $R^{17}$ is, independently at each occurrence, H, OH, $C_1$–$C_6$ alkyl, —OR$^{17a}$, —C(=O)OR$^{17a}$, —OC(=O)R$^{17a}$, —OC(=O)OR$^{17a}$, —C(=O)R$^{17a}$, —CH$_2$OC(=O)R$^{17a}$, —C(=O)SR$^{17a}$, —C(=S)OR$^{17a}$, —C(=S)SR$^{17a}$, phenyl, phenyl-($C_1$–$C_3$ alkyl)-, $C_1$–$C_4$ alkyl-C(=O)O—($C_1$–$C_4$ alkyl)-OC(=O)—, aryl-C(=O)O—($C_1$–$C_4$ alkyl)-OC(=O)—, $C_1$–$C_6$ alkyl-$NH_2$—C(=O)—, or phenyl-$NH_2$—C(=O)—;

each $R^{17a}$ is, independently at each occurrence, $C_1$–$C_6$ alkyl substituted with 0–3 $R^{17b}$, $C_2$–$C_6$ alkenyl substituted with 0–3 $R^{17b}$, $C_3$–$C_6$ alkynyl substituted with 0–3 $R^{17b}$, $C_3$–$C_8$ carbocycle substituted with 0–3 $R^{17b}$, $C_3$–$C_8$ carbocycle($C_1$–$C_3$ alkyl)- substituted with 0–3 $R^{17b}$, aryl substituted with 0–3 $R^{17b}$, aryl($C_1$–$C_3$ alkyl)- substituted with 0–3 $R^{17b}$, 5–6 membered heterocycle consisting of carbon atoms and 1–4 heteroatoms selected from the group: O, S, and N, and substituted with 0–3 $R^{17b}$; or 5–6 membered heterocycle-($C_1$–$C_3$ alkyl)- group consisting of carbon atoms and 1–4 heteroatoms selected from the group: O, S, and N, and substituted with 0–3 $R^{17b}$;

each $R^{17b}$ is, independently at each occurrence, H, halogen, —$CF_3$, —$OCF_3$, $C_1$–$C_6$ alkyl, OH, $C_1$–$C_6$ alkoxy, CN, $NO_2$, $NH_2$, N($CH_3$)$_2$, $CO_2$H, —C(=O)O($C_1$–$C_6$ alkyl), or —OC(=O)aryl;

each $R^{18}$ is, independently at each occurrence, H or $C_1$–$C_4$ alkyl;

alternatively, $R^{17}$ and $R^{18}$ combine to form —C(=O)OC(=O)—, —C(=O)O—, —C(=O)S—, or —C(=S)O—;

each $R^{19}$ is, independently at each occurrence, H or $C_1$–$C_4$ alkyl;

alternatively, $R^{18}$ and $R^{19}$, when attached to the same nitrogen, combine to form a 5–10 membered heterocycle consisting of one nitrogen atom, carbon atoms and 0–2 additional heteroatoms selected from the group consisting of N, O, and S;

each $R^{20}$ is, independently at each occurrence, H or $C_1$–$C_6$ alkyl;

each $R^{21}$ is, independently at each occurrence, H, $C_1$–$C_4$ alkyl, aryl, or aryl($C_1$–$C_3$ alkyl)-;

each $R^{21a}$ is, independently at each occurrence, H, $C_1$–$C_4$ alkyl, aryl, aryl($C_1$–$C_3$ alkyl)-, or $C_1$–$C_4$ haloalkyl;

each $R^{22}$ is, independently at each occurrence, H, $C_1$–$C_8$ alkyl substituted with 0–3 $R^{25}$, $C_2$–$C_8$ alkenyl substituted with 0–3 $R^{25}$, $C_2$–$C_8$ alkynyl substituted with 0–3

$R^{25}$, $C_3$–$C_{10}$ carbocycle substituted with 0–3 $R^{26}$, aryl substituted with 0–5 $R^{26}$, or 5–10 membered heterocycle containing from 1–4 heteroatoms selected from the group consisting of N, O, and S, and substituted with 0–3 $R^{27}$;

provided when $R^4$ or $R^{4a}$ are —OC(=O)O$R^{22}$, —S(=O)$R^{22}$, —S(=O)$_2R^{22}$, —N$R^{24}$S(=O)$R^{22}$, or —N$R^{24}$S(=O)$_2R^{22}$, then $R^{22}$ is not H;

each $R^{23}$ is, independently at each occurrence, H, $C_1$–$C_4$ alkyl, $C_2$–$C_4$ alkenyl, or $C_2$–$C_4$ alkynyl;

alternatively, $R^{22}$ and $R^{23}$, when attached to the same nitrogen, combine to form a 5–6 membered heterocycle consisting of one nitrogen atom, carbon atoms and 0–1 additional heteroatoms selected from the group consisting of —N($R^{24}$)—, O, and S;

each $R^{24}$ is, independently at each occurrence, H or $C_1$–$C_4$ alkyl;

each $R^{25}$ is, independently at each occurrence, H, halo, —$CF_3$, —$OCF_3$, OH, CN, $NO_2$, $C_1$–$C_4$ haloalkyl, $C_{1-8}$ alkoxy, ($C_{1-4}$ haloalkyl)oxy, $C_3$–$C_{10}$ carbocycle substituted with 0–3 $R^{26}$, aryl substituted with 0–5 $R^{26}$, or 5–10 membered heterocycle containing from 1–4 heteroatoms selected from the group consisting of N, O, and S, and substituted with 0–3 $R^{27}$;

each $R^{26}$ is, independently at each occurrence, H, OH, halo, CN, $NO_2$, —$CF_3$, —$SO_2R^{28}$, $NR^{29}R^{30}$, $C_1$–$C_6$ alkyl, $C_2$–$C_6$ alkenyl, $C_2$–$C_6$ alkynyl, $C_3$–$C_6$ cycloalkyl, $C_1$–$C_4$ haloalkyl, $C_1$–$C_4$ haloalkyl-oxy-, $C_1$–$C_4$ alkyloxy-, $C_1$–$C_4$ alkylthio-, $C_1$–$C_4$ alkyl-C(=O)—, or $C_1$–$C_4$ alkyl-C(=O)NH—;

each $R^{27}$ is, independently at each occurrence, H, OH, halo, —$CF_3$, —$SO_2R^{28}$, $NR^{29}R^{30}$, or $C_1$–$C_4$ alkyl;

each $R^{28}$ is, independently at each occurrence, $C_1$–$C_4$ alkyl, phenyl, or benzyl;

each $R^{29}$ is, independently at each occurrence, H, —$SO_2R^{28}$, —C(=O)$R^{28}$, $C_1$–$C_4$ alkyl, phenyl, or benzyl;

each $R^{30}$ is, independently at each occurrence, H or $C_1$–$C_4$ alkyl; and t, at each occurrence, is selected from 0, 1, 2, and 3.

2. A compound according to claim 1, wherein:

$A^1$ is —$CH_2$—; wherein $A^1$ is optionally substituted with 0–2 $R^{14}$;

$R^1$ is H or $C_1$–$C_6$ alkyl;

$R^3$ is H, F, Cl, Br, or $C_1$–$C_6$ alkyl;

$R^5$ is H, halo, $C_1$–$C_4$ haloalkyl, $C_1$–$C_4$ alkyl, $C_2$–$C_4$ alkenyl, or $C_2$–$C_4$ alkynyl;

each $R^{17}$ is, independently at each occurrence, H, OH, $C_1$–$C_6$ alkyl, $C_1$–$C_6$ alkyl-O—, $C_1$–$C_6$ alkyl-C(=O)—, $C_1$–$C_4$ alkyl-OC(=O)—, aryl-O—, aryl-OC(=O)—, aryl-$CH_2$—C(=O)—, phenyl, phenyl-($C_1$–$C_3$ alkyl)-, $C_1$–$C_4$ alkyl-C(=O)O—($C_1$–$C_4$ alkyl)—OC(=O)—, aryl-C(=O)O—($C_1$–$C_4$ alkyl)—OC(=O)—, $C_1$–$C_6$ alkyl-$NH_2$—C(=O)—, or phenyl-$NH_2$—C(=O)—;

each $R^{18}$ is, independently at each occurrence, H or $C_1$–$C_4$ alkyl;

each $R^{19}$ is, independently at each occurrence, H or $C_1$–$C_4$ alkyl; and alternatively, $R^{18}$ and $R^{19}$, when attached to the same nitrogen, combine to form a 5–10 membered heterocyclic ring consisting of one nitrogen atom, carbon atoms and 0–2 additional heteroatoms selected from the group consisting of N, O, and S.

3. A compound according to claim 2 of Formula (Ia):

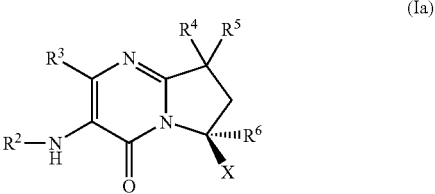

(Ia)

or a stereoisomer or pharmaceutically acceptable salt form thereof, wherein:

X is —C(=O)NH—$CH_2$—$R^8$, —S(=O)$_2$NH—$CH_2$—$R^8$, —$CR^{15}R^{15}$—NHC(=O)—$CH_2$—$R^8$, or —$CR^{15}R^5$—NHS(=O)$_2$—$CH_2$—$R^8$;

$R^2$ is H, —C(=O)$R^{2a}$, —C(=O)O$R^{2a}$, —C(=O)NH$R^{2a}$, —S(=O)$R^{2a}$, —S(=O)$_2R^{2a}$, —S(=O)$_2$NH$R^{2a}$, $C_1$–$C_6$ alkyl substituted with 0–3 $R^{2b}$, $C_2$–$C_6$ alkenyl substituted with 0–3 $R^{2b}$, $C_2$–$C_6$ alkynyl substituted with 0–3 $R^{2b}$, $C_3$–$C_6$ carbocycle substituted with 0–3 $R^{2c}$, aryl substituted with 0–3 $R^{2c}$, or 5–6 membered heterocycle consisting of carbon atoms and 1–4 heteroatoms selected from the group: O, S, and N, and substituted with 0–3 $R^{2c}$;

each $R^{2b}$ is, independently at each occurrence, H, F, Cl, Br, I, $NO_2$, CN, —NCS, —$CF_3$, —$OCF_3$, —$CH_3$, —$CH_2CH_3$, —CH($CH_3$)$_2$, —$OCH_3$, =O, OH, $CO_2H$, $NH_2$, —NH($CH_3$), N($CH_3$)$_2$, $CO_2R^{21}$, —C(=O)$NR^{21}R^{21}$, —NHC(=O)$R^{21}$, —$NR^{21}R^{21}$, —$NHSO_2R^{21}$, —$SO_2R^{21}$, —$SO_2NR^{21}R^{21}$, $OR^{21a}$, $SR^{21a}$, C(=O)$R^{21a}$, —S(=O)$R^{21a}$, $C_1$–$C_4$ haloalkyl, $C_1$–$C_4$ haloalkoxy, $C_3$–$C_6$ carbocycle substituted with 0–3 $R^2c$, aryl substituted with 0–3 $R^{2c}$, or 5–6 membered heterocycle consisting of carbon atoms and 1–4 heteroatoms selected from the group: O, S, and N, and substituted with 0–3 $R^{2c}$;

each $R^{2c}$ is, independently at each occurrence, H, F, Cl, Br, I, $NO_2$, CN, —NCS, —$CF_3$, —$OCF_3$, —$CH_3$, —$OCH_3$, =O, OH, $CO_2H$, $NH_2$, NH($CH_3$), N($CH_3$)$_2$, $CO_2R^{21}$, —C(=O)$NR^{21}$ $R^{21}$, —NHC(=O)$R^{21}$, —$NR^{21}R^{21}$, —$NHSO_2R^{21}$, —$SO_2R^{21}$, —$SO_2NR^{21}R^{21}$, —$OR^{21a}$, —$SR^{21a}$, —C(=O)$R^{21a}$, —S(=O)$R^{21a}$, $C_1$–$C_4$ haloalkyl, $C_1$–$C_4$ haloalkoxy, or $C_1$–$C_4$ alkyl;

$R^3$ is H, F, Cl, Br, methyl, ethyl, propyl, or butyl;

$R^4$ is H, halo, —$CF_3$, —$OCF_3$, OH, CN, $NO_2$, —$OR^{22}$, —$SR^{22}$, —$NR^{22}R^{23}$, —C(=O)$R^{22}$, —C(=O)$NR^{22}R^{23}$, —$NR^{24}$C(=O)$R^{22}$, —$NR^{24}$C(=O)$NR^{22}R^{23}$, —$NR^{24}$C(=O)$NR^{24}$C(=O)$R^{22}$, —C(=O)$OR^{22}$, —OC(=O)$R^{22}$, —OC(=O)$OR^{22}$, —$NR^{24}$C(=O)$OR^{22}$, —OC(=O)$NR^{22}R^{23}$, —S(=O)$R^{22}$, —S(=O)$_2R^{22}$, —S(=O)$NR^{22}R^{23}$, —S(=O)$_2NR^{22}R^{23}$, —$NR^{24}$S(=O)$_2NR^{22}R^{23}$, —$NR^{24}$S(=O)$R^{22}$, —$NR^{24}$S(=O)$_2R^{22}$, $C_1$–$C_4$ haloalkyl, $C_1$–$C_6$ alkoxy, ($C_1$–$C_4$ haloalkyl)oxy, $C_1$–$C_6$ alkyl, $C_2$–$C_6$ alkenyl, $C_2$–$C_6$ alkynyl, or $C_1$–$C_3$ alkyl substituted with $R^{4a}$;

$R^{4a}$ is —$NR^{22}R^{23}$, —C(=O)$NR^{22}R^{23}$, —$NR^{24}$C(=O)$R^{22}$, —$NR^{24}$C(=O)$NR^{22}R^{23}$, —$NR^{24}$C(=O)$NR^{24}$C(=O)$R^{22}$, —C(=O)$OR^{22}$, —$NR^{24}$C(=O)$OR^{22}$, —$NR^{24}$S(=O)$_2NR^{22}R^{23}$, or —$NR^{24}$S(=O)$_2R^{22}$;

$R^8$ is phenyl substituted with one $R^{8a}$ and 0–1 $R^{8b}$, pyridyl substituted with one $R^{8a}$ and 0–1 $R^{8b}$, naphthyl substituted with one $R^{8a}$ and 0–1 $R^{8b}$, quinolinyl substituted with one $R^{8a}$ and 0–1 $R^{8b}$, isoquinolinyl substituted with one R8a and 0–1 R8b, phthalazinyl substituted with one R8a and 0–1 R8b, quinazolinyl substituted with one R8a and 0–1 R8b, indolyl substituted with one R8a and 0–1 R8b, isoindolyl substituted with one R8a and 0–1 R8b, indolinyl substituted with one R8a and 0–1 R8b, 1H-indazolyl substituted with one R8a and 0–1 R8b, or benzimidazolyl substituted with one R8a and 0–1 R8b;

each $R^{8a}$ is, independently at each occurrence, —C(=NH)NH$_2$, —C(=O)NH$_2$, —NHC(=NH)NH$_2$, —NHCH(=NH), —NH$_2$, —CH$_2$C(=NH)NH$_2$, —CH$_2$NHC(=NH)NH$_2$, —CH$_2$NHCH(=NH), —CH$_2$NH$_2$, or —CH$_2$C(=O)NH$_2$;

each $R^{15}$ is, independently at each occurrence, H, F, or methyl;

alternatively, —CR$^{15}$R$^{15}$— forms a gem disubstituted cyclopropyl group;

each $R^{17}$ is, independently at each occurrence, H, OH, or $C_1$–$C_4$ alkyl;

each $R^{18}$ is, independently at each occurrence, H or $C_1$–$C_4$ alkyl;

each $R^{19}$ is, independently at each occurrence, H or $C_1$–$C_4$ alkyl;

each $R^{22}$ is, independently at each occurrence, H, $C_1$–$C_4$ alkyl, $C_2$–$C_4$ alkenyl, $C_3$–$C_6$ cycloalkyl, phenyl substituted with 0–5 $R^{26}$, or 5–6 membered heterocycle containing from 1–4 heteroatoms selected from the group consisting of N, O, and S, and substituted with 0–3 $R^{27}$;

provided when $R^4$ or $R^{4a}$ are —OC(=O)OR$^{22}$, —S(=O)R$^{22}$, —S(=O)$_2$R$^{22}$, —NR$^{24}$S(=O)R$^{22}$, or —NR$^{24}$S(=O)$_2$R$^{22}$, then $R^{22}$ is not H;

each $R^{23}$ is, independently at each occurrence, H or $C_1$–$C_4$ alkyl;

alternatively, $R^{22}$ and $R^{23}$, when attached to the same nitrogen, combine to form a 5–6 membered heterocycle consisting of one nitrogen atom, carbon atoms and 0–1 additional heteroatoms selected from the group consisting of —N(R$^{24}$)— and O;

each $R^{26}$ is, independently at each occurrence, H, OH, F, Cl, CN, NO$_2$, CF$_3$, —SO$_2$CH$_3$, —SO$_2$CH$_2$CH$_3$, NH$_2$, NH(CH$_3$), N(CH$_3$)$_2$, methyl, ethyl, propyl, allyl, —OCF$_3$, methoxy, ethoxy, —SCH$_3$, —SCH$_2$CH$_3$, —C(=O)CH$_3$, —C(=O)CH$_2$CH$_3$, —NHC(=O)CH$_3$, or —NHC(=O)CH$_2$CH$_3$; and t is 0 or 1.

4. A compound according to claim 3 of Formula (Ib):

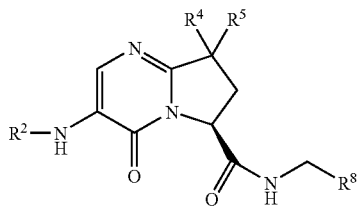

(Ib)

or a stereoisomer or pharmaceutically acceptable salt form thereof, wherein:

$R^2$ is H, —C(=O)R$^{2a}$, —C(=O)OR$^{2a}$, —S(=O)$_2$R$^{2a}$, $C_1$–$C_6$ alkyl substituted with 0–3 $R^{2b}$, $C_2$–$C_6$ alkenyl substituted with 0–3 $R^{2b}$, $C_2$–$C_6$ alkynyl substituted with 0–3 $R^{2b}$, $C_3$–$C_6$ carbocycle substituted with 0–3 $R^{2c}$, aryl substituted with 0–3 $R^{2c}$, or 5–6 membered heterocycle consisting of carbon atoms and 1–4 heteroatoms selected from the group: O, S, and N, and substituted with 0–3 $R^{2c}$;

each $R^{2a}$ is, independently at each occurrence, H, $C_1$–$C_6$ alkyl substituted with 0–3 $R^{2b}$, $C_2$–$C_6$ alkenyl substituted with 0–3 $R^{2b}$, $C_2$–$C_6$ alkynyl substituted with 0–3 $R^{2b}$, $C_3$–$C_6$ carbocycle substituted with 0–3 $R^{2c}$, aryl substituted with 0–3 $R^{2c}$, or 5–6 membered heterocycle consisting of carbon atoms and 1–4 heteroatoms selected from the group: O, S, and N, and substituted with 0–3 $R^{2c}$;

provided when $R^2$ is —S(=O)R$^{2a}$ or —S(=O)$_2$R$^{2a}$, then $R^{2a}$ is not H;

each $R^{2b}$ is, independently at each occurrence, H, F, Cl, Br, I, NO$_2$, CN, —NCS, —CF$_3$, —OCF$_3$, —CH$_3$, —CH$_2$CH$_3$, —CH(CH$_3$)$_2$, —OCH$_3$, =O, OH, CO$_2$H, NH$_2$, NH(CH$_3$), N(CH$_3$)$_2$, CO$_2$R$^{21}$, —C(=O)NR$^{21}$R$^{21}$, —NHC(=O)R$^{21}$, —NR$^{21}$R$^{21}$, —NHSO$_2$R$^{21}$, —SO$_2$R$^{21}$, —SO$_2$NR$^{21}$R$^{21}$, —OR$^{21a}$, —SR$^{21a}$, —C(=O)R$^{21a}$, —S(=O)R$^{21a}$, $C_1$–$C_4$ haloalkyl, $C_1$–$C_4$ haloalkoxy, $C_3$–$C_6$ carbocycle substituted with 0–3 $R^{2c}$, aryl substituted with 0–3 $R^{2c}$, or 5–6 membered heterocycle consisting of carbon atoms and 1–4 heteroatoms selected from the group: O, S, and N, and is substituted with 0–3 $R^{2c}$;

each $R^{2c}$ is, independently at each occurrence, H, F, Cl, Br, I, NO$_2$, CN, —NCS, —CF$_3$, —OCF$_3$, —CH$_3$, —OCH$_3$, =O, OH, CO$_2$H, NH$_2$, NH(CH$_3$), N(CH$_3$)$_2$, CO$_2$R$^{21}$, —C(=O)NR$^{21}$R$^{21}$, —NHC(=O)R$^{21}$, —NR$^{21}$R$^{21}$, —NHSO$_2$R$^{21}$, —SO$_2$R$^{21}$, —SO$_2$NR$^{21}$R$^{21}$, —OR$^{21a}$, —SR$^{21a}$, C(=O)R$^{21a}$, —S(=O)R$^{21a}$, $C_1$–$C_4$ haloalkyl, $C_1$–$C_4$ haloalkoxy, or $C_1$–$C_4$ alkyl;

$R^4$ is H, F, Cl, Br, —CF$_3$, $C_2$–$C_4$ haloalkyl, $C_1$–$C_6$ alkyl, $C_2$–$C_6$ alkenyl, $C_2$–$C_6$ alkynyl, —NR$^{22}$R$^{23}$, —NR$^{24}$C(=O)R$^{22}$, —CH$_2$NR$^{22}$R$^{23}$, —CH$_2$C(=O)NR$^{22}$R$^{23}$, —CH$_2$NR$^{24}$C(=O)R$^{22}$, —CH$_2$NR$^{24}$C(=O)NR$^{22}$R$^{23}$, —CH$_2$C(=O)OR$^{22}$, —CH$_2$NR$^{24}$C(=O)OR$^{22}$, —CH$_2$NR$^{24}$S(=O)$_2$NR$^{22}$R$^{23}$, or —CH$_2$NR$^{24}$S(=O)$_2$R$^{22}$;

$R^5$ is H, methyl, ethyl, propyl, butyl, or allyl;

$R^8$ is phenyl substituted with —C(=NH)NH$_2$ and 0–1 $R^{8b}$;

$R^{8b}$ is H, F, Cl, Br, —CH$_3$, —OCH$_3$, —OH, —CF$_3$, —OCF$_3$, —CN, —NO$_2$, —C(=O)NH$_2$, —NH$_2$, —NH(CH$_3$), or —N(CH$_3$)$_2$;

each $R^{21}$ is, independently at each occurrence, H, methyl, ethyl, propyl, butyl, aryl, (aryl)methyl-, (aryl)ethyl-, or (aryl)propyl-;

each $R^{21a}$ is, independently at each occurrence, H, methyl, ethyl, propyl, butyl, aryl, (aryl)methyl-, (aryl)ethyl-, (aryl)propyl-, or $C_1$–$C_4$ haloalkyl;

each $R^{22}$ is, independently at each occurrence, H, methyl, ethyl, propyl, butyl, allyl, cyclopropyl, cyclobutyl, cyclopentyl, cyclohexyl, phenyl, pyridinyl, furanyl, thienyl, pyrrolyl, pyrazolyl, pyrazinyl, piperazinyl, piperidinyl, imidazolyl, imidazolidinyl, isoxazolyl, morpholinyl, oxazolyl, oxazolidinyl, or tetrahydrofuranyl;

provided when $R^4$ is —CH$_2$NR$^{24}$S(=O)$_2$R$^{22}$, then $R^{22}$ is not H;

each $R^{23}$ is, independently at each occurrence, H, methyl, ethyl, propyl, and butyl;

alternatively, $R^{22}$ and $R^{23}$, when attached to the same nitrogen, combine to form pyrrolidinyl, piperidinyl, morpholinyl, piperazinyl, or N-methylpiperazinyl; and each $R^{24}$ is, independently at each occurrence, H, methyl, ethyl, propyl, or butyl.

5. A compound according to claim 4 of Formula (Ic):

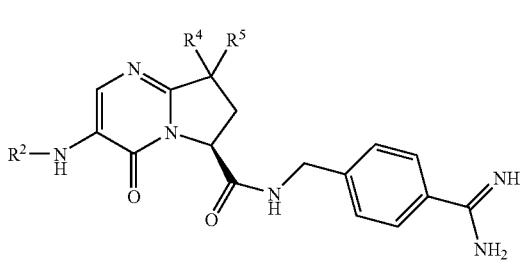

(Ic)

or a stereoisomer or pharmaceutically acceptable salt form thereof, wherein:
R$^2$ is H, —C(=O)R$^2$a, —C(=O)OR$^{2a}$, —S(=O)$_2$R$^{2a}$, methyl, ethyl, propyl, butyl, pentyl, hexyl, propenyl, butenyl, pentenyl, cyclopropyl, cyclobutyl, cyclopentyl, cyclohexyl, methyl substituted with R$^{2b}$, ethyl substituted with R$^{2b}$, propyl substituted with R$^{2b}$, butyl substituted with R$^{2b}$, pentyl substituted with R$^{2b}$, or phenyl substituted with 0–3 R$^{2c}$;
each R$^{2a}$ is, independently at each occurrence, methyl, ethyl, propyl, butyl, pentyl, hexyl, propenyl, butenyl, pentenyl, cyclopropyl, cyclobutyl, cyclopentyl, cyclohexyl, methyl substituted with R$^{2b}$, ethyl substituted with R$^{2b}$, propyl substituted with R$^{2b}$, butyl substituted with R$^{2b}$, pentyl substituted with R$^{2b}$, phenyl substituted with 0–3 R$^{2c}$, or naphthyl substituted with 0–3 R$^{2c}$;
each R$^{2b}$ is, independently at each occurrence, H, F, Cl, Br, I, NO$_2$, CN, —NCS, —CF$_3$, —OCF$_3$, —CH$_3$, —CH$_2$CH$_3$, —CH(CH$_3$)$_2$, —OCH$_3$, =O, OH, CO$_2$H, NH$_2$, NH(CH$_3$), N(CH$_3$)$_2$, CO$_2$R$^{21}$, —C(=O)NHR$^{21}$, —NHC(=O)R$^{21}$, —NHR$^{21}$, —NHSO$_2$R$^{21}$, —SO$_2$R$^{21}$, —SO$_2$NHR$^{21}$, —OR$^{21a}$, —SR$^{21a}$, —C(=O)R$^{21a}$, —S(=O)R$^{21a}$, or phenyl substituted with 0–3 R$^{2c}$;
each R$^{2c}$ is, independently at each occurrence, H, F, Cl, Br, I, NO$_2$, CN, —NCS, —CF$_3$, —OCF$_3$, —CH$_3$, —OCH$_3$, =O, OH, CO$_2$H, NH$_2$, NH(CH$_3$), N(CH$_3$)$_2$, CO$_2$R$^{21}$, —C(=O)NHR$^{21}$, —NHC(=O)R$^{21}$, —NHR$^{21}$, —NHSO$_2$R$^{21}$, —SO$_2$R$^{21}$, —SO$_2$NHR$^{21}$, —OR$^{21a}$, SR$^{21a}$, C(=O)R$^{21a}$, S(=O)R$^{21a}$, methyl, ethyl, propyl, or butyl;
R$^4$ is H, F, methyl, ethyl, propyl, allyl, piperidinyl, —NR$^{22}$R$^{23}$, —NHC(=O)R$^{22}$, —CH$_2$NR$^{22}$R$^{23}$, —CH$_2$C(=O)NR$^{22}$R$^{23}$, —CH$_2$NHC(=O)R$^{22}$, —CH$_2$NHC(=O)NR$^{22}$R$^{23}$, —CH$_2$C(=O)OR$^{22}$, or —CH$_2$NHS(=O)$_2$R$^{22}$;
R$^5$ is H, methyl, ethyl, propyl, or allyl;
each R$^{21}$ is, independently at each occurrence, H, methyl, ethyl, propyl, butyl, phenyl, benzyl, or phenethyl;
each R$^{21a}$ is, independently at each occurrence, H, methyl, ethyl, propyl, butyl, phenyl, benzyl, phenethyl, or —CF$_3$;
each R$^{22}$ is, independently at each occurrence, H, methyl, ethyl, propyl, allyl, cyclopropyl, cyclobutyl, cyclopentyl, cyclohexyl, or phenyl;
provided when R$^4$ is —CH$_2$NHS(=O)$_2$R$^{22}$, then R$^{22}$ is not H; and
R$^{23}$ is H, methyl, ethyl, propyl, or butyl.

6. A compound according to claim 1, wherein the compound is selected from the group:

(S)-3-benzylamino-4-oxo-4,6,7,8-tetrahydro-pyrrolo[1,2-a]pyrimidine-6-carboxylic acid 4-carbamimidoyl-benzylamide;

(S)-4-oxo-3-phenethylamino-4,6,7,8-tetrahydro-pyrrolo[1,2-a]pyrimidine-6-carboxylic acid 4-carbamimidoyl-benzylamide;

(S)-3-diethylamino-4-oxo-4,6,7,8-tetrahydro-pyrrolo[1,2-a]pyrimidine-6-carboxylic acid 4-carbamimidoyl-benzylamide;

(S)-3-isopropylamino-4-oxo-4,6,7,8-tetrahydro-pyrrolo[1,2-a]pyrimidine-6-carboxylic acid 4-carbamimidoyl-benzylamide;

(S)-3-ethylamino-4-oxo-4,6,7,8-tetrahydro-pyrrolo[1,2-a]pyrimidine-6-carboxylic acid 4-carbamimidoyl-benzylamide;

(S)-3-cyclopentylamino-4-oxo-4,6,7,8-tetrahydro-pyrrolo[1,2-a]pyrimidine-6-carboxylic acid 4-carbamimidoyl-benzylamide;

(S)-3-isobutylamino-4-oxo-4,6,7,8-tetrahydro-pyrrolo[1,2-a]pyrimidine-6-carboxylic acid 4-carbamimidoyl-benzylamide;

(S)-3-propylamino-4-oxo-4,6,7,8-tetrahydro-pyrrolo[1,2-a]pyrimidine-6-carboxylic acid 4-carbamimidoyl-benzylamide;

(S)-3-diisobutylamino-4-oxo-4,6,7,8-tetrahydro-pyrrolo[1,2-a]pyrimidine-6-carboxylic acid 4-carbamimidoyl-benzylamide;

(S)-3-sec-butylamino-4-oxo-4,6,7,8-tetrahydro-pyrrolo[1,2-a]pyrimidine-6-carboxylic acid 4-carbamimidoyl-benzylamide;

(S)-3-(1-ethyl-propylamino)-4-oxo-4,6,7,8-tetrahydro-pyrrolo[1,2-a]pyrimidine-6-carboxylic acid 4-carbamimidoyl-benzylamide;

(S)-4-[6-(4-carbamimidoyl-benzylcarbamoyl)-4-oxo-4,6,7,8-tetrahydro-pyrrolo[1,2-a]pyrimidin-3-ylamino]-pentanoic acid benzyl ester;

(S)-4-[6-(4-carbamimidoyl-benzylcarbamoyl)-4-oxo-4,6,7,8-tetrahydro-pyrrolo[1,2-a]pyrimidin-3-ylamino]-pentanoic acid;

(S)-[6-(4-carbamimidoyl-benzylcarbamoyl)-4-oxo-4,6,7,8-tetrahydro-pyrrolo[1,2-a]pyrimidin-3-yl]-carbamic acid benzyl ester;

(S)-3-amino-4-oxo-4,6,7,8-tetrahydro-pyrrolo[1,2-a]pyrimidine-6-carboxylic acid 4-carbamimidoyl-benzylamide;

(S)-3-methanesulfonylamino-4-oxo-4,6,7,8-tetrahydro-pyrrolo[1,2-a]pyrimidine-6-carboxylic acid 4-carbamimidoyl-benzylamide;

(S)-3-benzenesulfonylamino-4-oxo-4,6,7,8-tetrahydro-pyrrolo[1,2-a]pyrimidine-6-carboxylic acid 4-carbamimidoyl-benzylamide;

(6S, 8R)-8-acetylamino-8-methyl-4-oxo-3-propylamino-4,6,7,8-tetrahydro-pyrrolo[1,2-a]pyrimidine-6-carboxylic acid 4-carbamimidoyl-benzylamide

[6-(4-carbamimidoyl-benzylcarbamoyl)-6-methyl-4-oxo-4,6,7,8-tetrahydro-pyrrolo[1,2-a]pyrimidin-3-yl]-carbamic acid benzyl ester;

[6-allyl-6-(4-carbamimidoyl-benzylcarbamoyl)-4-oxo-4,6,7,8-tetrahydro-pyrrolo[1,2-a]pyrimidin-3-yl]-carbamic acid benzyl ester;

[6-benzyl-6-(4-carbamimidoyl-benzylcarbamoyl)-4-oxo-4,6,7,8-tetrahydro-pyrrolo[1,2-a]pyrimidin-3-yl]-carbamic acid benzyl ester;

[6-(4-carbamimidoyl-benzylcarbamoyl)-6-ethyl-4-oxo-4,6,7,8-tetrahydro-pyrrolo 1,2-a]pyrimidin-3-yl]-carbamic acid benzyl ester;

[6-(4-carbamimidoyl-benzylcarbamoyl)-6-methoxymethyl-4-oxo-4,6,7,8-tetrahydro-pyrrolo[1,2-a]pyrimidin-3-yl]-carbamic acid benzyl ester;

(S)-[6-(3-carbamoyl-benzylcarbamoyl)-4-oxo-4,6,7,8-tetrahydro-pyrrolo[1,2-a]pyrimidin-3-yl]-carbamic acid benzyl ester;

(S)-4-oxo-3-(3-trifluoromethyl-benzylamino)-4,6,7,8-tetrahydro-pyrrolo[1,2-a]pyrimidine-6-carboxylic acid 4-carbamimidoyl-benzylamide;

(6S,8R)-8-ethylamino-8-methyl-4-oxo-3-propylamino-4,6,7,8-tetrahydro-pyrrolo 1,2-a]pyrimidine-6-carboxylic acid 4-carbamimidoyl-benzylamide;

(6S,8R)-8-isopropylamino-8-methyl-4-oxo-3-propylamino-4,6,7,8-tetrahydro-pyrrolo[1,2-a]pyrimidine-6-carboxylic acid 4-carbamimidoyl-benzylamide;

(6S,8R)-4-oxo-8-propyl-3-propylamino-4,6,7,8-tetrahydro-pyrrolo[1,2-a]pyrimidine-6-carboxylic acid 4-carbamimidoyl-benzylamide;

(S)-4-oxo-8,8-dipropyl-3-propylamino-4,6,7,8-tetrahydro-pyrrolo[1,2-a]pyrimidine-6-carboxylic acid 4-carbamimidoyl-benzylamide;

(S)-3-(naphthalene-1-sulfonylamino)-4-oxo-4,6,7,8-tetrahydro-pyrrolo[1,2-a]pyrimidine-6-carboxylic acid 4-carbamimidoyl-benzylamide;

(S)-3-(4-methoxy-benzenesulfonylamino)-4-oxo-4,6,7,8-tetrahydro-pyrrolo[1,2-a]pyrimidine-6-carboxylic acid 4-carbamimidoyl-benzylamide;

(S)-3-(4-fluoro-benzenesulfonylamino)-4-oxo-4,6,7,8-tetrahydro-pyrrolo[1,2-a]pyrimidine-6-carboxylic acid 4-carbamimidoyl-benzylamide;

(S)-4-oxo-3-(4-trifluoromethoxy-benzenesulfonylamino)-4,6,7,8-tetrahydro-pyrrolo[1,2-a]pyrimidine-6-carboxylic acid 4-carbamimidoyl-benzylamide;

(S)-4-oxo-3-(4-phenoxy-benzenesulfonylamino)-4,6,7,8-tetrahydro-pyrrolo[1,2-a]pyrimidine-6-carboxylic acid 4-carbamimidoyl-benzylamide;

(S)-3-(4-acetyl-benzenesulfonylamino)-4-oxo-4,6,7,8-tetrahydro-pyrrolo[1,2-a]pyrimidine-6-carboxylic acid 4-carbamimidoyl-benzylamide;

(S)-4-oxo-3-phenylmethanesulfonylamino-4,6,7,8-tetrahydro-pyrrolo[1,2-a]pyrimidine-6-carboxylic acid 4-carbamimidoyl-benzylamide;

(S)-8,8-diethyl-4-oxo-3-propylamino-4,6,7,8-tetrahydro-pyrrolo[1,2-a]pyrimidine-6-carboxylic acid 4-carbamimidoyl-benzylamide;

(6R,8S)-[6-(4-carbamimidoyl-benzylcarbamoyl)-8-methyl-4-oxo-3-propylamino-4,6,7,8-tetrahydro-pyrrolo[1,2-a]pyrimidin-8-yl]-acetic acid tert-butyl ester;

(6R,8S)-[6-(4-carbamimidoyl-benzylcarbamoyl)-8-methyl-4-oxo-3-propylamino-4,6,7,8-tetrahydro-pyrrolo[1,2-a]pyrimidin-8-yl]-acetic acid;

(6R,8S)-8-methyl-4-oxo-8-phenylcarbamoylmethyl-3-propylamino-4,6,7,8-tetrahydro-pyrrolo[1,2-a]pyrimidine-6-carboxylic acid 4-carbamimidoyl-benzylamide;

(6R,8S)-8-methyl-4-oxo-8-(2-oxo-2-piperidin-1-yl-ethyl)-3-propylamino-4,6,7,8-tetrahydro-pyrrolo[1,2-a]pyrimidine-6-carboxylic acid 4-carbamimidoyl-benzylamide;

(6R,8S)-8-formylamino-8-methyl-4-oxo-3-propylamino-4,6,7,8-tetrahydro-pyrrolo[1,2-a]pyrimidine-6-carboxylic acid 4-carbamimidoyl-benzylamide; and (6R,8S)-8-methyl-4-oxo-3-propylamino-8-ureido-4,6,7,8-tetrahydro-pyrrolo[1,2-a]pyrimidine-6-carboxylic acid 4-carbamimidoyl-benzylamide;

or a stereoisomer or a pharmaceutically acceptable salt form thereof.

7. A pharmaceutical composition comprising a pharmaceutically acceptable carrier and a therapeutically effective amount of a compound of claim 1 or a pharmaceutically acceptable salt form thereof.

8. A pharmaceutical composition comprising a pharmaceutically acceptable carrier and a therapeutically effective amount of a compound of claim 2 or a pharmaceutically acceptable salt form thereof.

9. A pharmaceutical composition comprising a pharmaceutically acceptable carrier and a therapeutically effective amount of a compound of claim 3 or a pharmaceutically acceptable salt form thereof.

10. A pharmaceutical composition comprising a pharmaceutically acceptable carrier and a therapeutically effective amount of a compound of claim 4 or a pharmaceutically acceptable salt form thereof.

11. A pharmaceutical composition comprising a pharmaceutically acceptable carrier and a therapeutically effective amount of a compound of claim 5 or a pharmaceutically acceptable salt form thereof.

12. A pharmaceutical composition comprising a pharmaceutically acceptable carrier and a therapeutically effective amount of a compound of claim 6 or a pharmaceutically acceptable salt form thereof.

\* \* \* \* \*